United States Patent
Meloni

(10) Patent No.: US 12,303,550 B2
(45) Date of Patent: May 20, 2025

(54) NEUROPROTECTIVE PEPTIDES

(71) Applicant: ARGENICA THERAPEUTICS PTY LTD, Nedlands (AU)

(72) Inventor: Bruno Meloni, Mount Hawthorn (AU)

(73) Assignee: ARGENICA THERAPEUTICS PTY LTD, Nedlands (AU)

( * ) Notice: Subject to any disclaimer, the term of this patent is extended or adjusted under 35 U.S.C. 154(b) by 0 days.

(21) Appl. No.: 17/556,730

(22) Filed: Dec. 20, 2021

(65) Prior Publication Data

US 2022/0111003 A1     Apr. 14, 2022

Related U.S. Application Data

(62) Division of application No. 16/041,483, filed on Jul. 20, 2018, now Pat. No. 11,229,678, which is a division of application No. 14/392,392, filed as application No. PCT/AU2014/050326 on Oct. 30, 2014, now abandoned.

(30) Foreign Application Priority Data

Oct. 30, 2013  (AU) ................. 2013904197
Jun. 17, 2014  (AU) ................. 2014902319

(51) Int. Cl.
| | | |
|---|---|---|
| A61K 38/17 | (2006.01) |
| A61K 9/00 | (2006.01) |
| C07K 7/06 | (2006.01) |
| C07K 7/08 | (2006.01) |
| C07K 14/00 | (2006.01) |
| A61K 38/00 | (2006.01) |
| A61P 9/10 | (2006.01) |
| A61P 21/00 | (2006.01) |
| A61P 25/02 | (2006.01) |
| A61P 25/16 | (2006.01) |

(52) U.S. Cl.
CPC ........ *A61K 38/1709* (2013.01); *A61K 9/0053* (2013.01); *C07K 7/06* (2013.01); *C07K 7/08* (2013.01); *C07K 14/001* (2013.01); *A61K 38/00* (2013.01); *A61P 9/10* (2018.01); *A61P 21/00* (2018.01); *A61P 25/02* (2018.01); *A61P 25/16* (2018.01)

(58) Field of Classification Search
CPC .............. A61K 38/1709; A61K 9/0053; A61K 38/00; C07K 7/06; C07K 7/08; C07K 14/001; A61P 9/10
See application file for complete search history.

(56) References Cited

U.S. PATENT DOCUMENTS

| | | |
|---|---|---|
| 3,773,919 A | 11/1973 | Boswell et al. |
| 4,684,624 A | 8/1987 | Hosobuchi et al. |
| 5,004,602 A | 4/1991 | Hutchinson |
| 5,559,095 A | 9/1996 | Miljanich et al. |
| 6,251,854 B1 | 6/2001 | Montal et al. |
| 7,544,483 B2 | 6/2009 | Tadros |
| 8,507,439 B2 | 8/2013 | Shashoua |
| 9,127,082 B2 | 9/2015 | Saarma et al. |
| 9,220,744 B2 | 12/2015 | Rothbard et al. |
| 9,345,744 B2 | 5/2016 | Gourdie et al. |
| 9,585,907 B2 | 3/2017 | Gan |
| 9,592,270 B2 | 3/2017 | Saarma et al. |
| 2005/0192210 A1 | 9/2005 | Rothbard et al. |
| 2007/0269892 A1 | 11/2007 | Adami et al. |
| 2009/0281036 A1 | 11/2009 | Meyer |
| 2010/0233084 A1 | 9/2010 | Narasimhaswamy et al. |
| 2012/0122790 A1 | 5/2012 | Drezner et al. |
| 2012/0301446 A1 | 11/2012 | Zhu et al. |
| 2013/0018000 A1 | 1/2013 | Stout |
| 2014/0314663 A1 | 10/2014 | Sarkar et al. |
| 2014/0315789 A1 | 10/2014 | Willcox et al. |
| 2015/0126457 A1 | 5/2015 | Goebel et al. |
| 2016/0002300 A1 | 1/2016 | Shih et al. |
| 2016/0272689 A1 | 9/2016 | Rauvala et al. |

FOREIGN PATENT DOCUMENTS

| | | | |
|---|---|---|---|
| JP | 2013-518587 A | 5/2013 | |
| WO | WO-0074701 A2 * | 12/2000 | ............. A61K 38/03 |
| WO | WO-2003/106485 A1 | 12/2003 | |
| WO | WO-2005/084301 A2 | 9/2005 | |
| WO | WO-2008/093059 A1 | 8/2008 | |
| WO | WO-2008/093060 A2 | 8/2008 | |
| WO | WO-2008/133929 A2 | 11/2008 | |
| WO | WO-2009/045062 A1 | 4/2009 | |
| WO | WO-2011/056300 A1 | 5/2011 | |
| WO | WO-2011/063320 A2 | 5/2011 | |
| WO | WO-2011/097181 A2 | 8/2011 | |

(Continued)

OTHER PUBLICATIONS

Murray H. Kown, L-Arginine Polymers Inhibit the Development of Vein Graft Neointimal Hyperplasia,, The Journal of Thoracic and Cardiovascular Surgery May 2001.*
Sotiris C. Stamou, Stroke After Coronary Artery Bypass Incidence, Predictors, and Clinical Outcome, Stroke. 2001;32:1508-1513.*
Declaration of Bruno Meloni, dated Aug. 15, 2019, filed during the prosecution of U.S. Appl. No. 16/041,483.
"A Ramis" (2011) Project No. 8909.1 http://www.aramis.admtn.ch. "Poly-arginine peptides: neuroprotection against excitotoxic neural injury" p. 1-6.
Aarts et al., Treatment of ischemic brain damage by perturbing NMDA receptor-PSD-95 protein interactions, *Science*. 298:846-50 (2002).
Ambrosi et al., A further update on the role of excitotoxicity in the pathogenesis of Parkinson's disease, *J. Neural. Transm. (Vienna)*. 121:849-59 (2014).

(Continued)

*Primary Examiner* — Julie Ha
*Assistant Examiner* — Erinne R Dabkowski
(74) *Attorney, Agent, or Firm* — MARSHALL, GERSTEIN & BORUN LLP

(57) ABSTRACT

The invention relates to the use of an isolated peptide of 10 to 32 amino acid residues in length for the treatment of neural injury, wherein the isolated peptide comprises at least 10 to 22 arginine residues. The peptide may be a poly-arg sequence or an arginine-rich peptide.

12 Claims, 23 Drawing Sheets

Specification includes a Sequence Listing.

(56) References Cited

FOREIGN PATENT DOCUMENTS

| | | |
|---|---|---|
| WO | WO-2013/076666 A1 | 5/2013 |
| WO | WO-2013/082286 A1 | 6/2013 |
| WO | WO-2013/158739 A1 | 10/2013 |
| WO | WO-2013/163423 A1 | 10/2013 |
| WO | WO-2014/124047 A1 | 8/2014 |
| WO | WO-2014/202834 A1 | 12/2014 |
| WO | WO-2015/061856 A1 | 5/2015 |

OTHER PUBLICATIONS

Arthur et al., Necrotic death of neurons following an excitotoxic insult is prevented by a peptide inhibitor of c-jun N-terminal kinase, *J. Neurochem.* 102:65-76 (2007).

Bano et al., Ca2+ signals and neuronal death in brain ischemia, *Stroke.* 38:674-676 (2007).

Barker-Haliski et al., Glutamatergic Mechanisms Associated with Seizures and Epilepsy, *Cold Spring Harb. Perspect. Med.* 5:1-15 (2015).

Bessero et al., Neuroprotection for optic nerve disorders, *Curr. Opin. Neurol.* 23:10-15 (2010).

Borsello et al., A peptide inhibitor of c-Jun N-terminal kinase protects against excitotoxicity and cerebral ischemia, *Nat. Med.* 9:1180-1186 (2003).

Brugidou et al., The retro-inverso form of a homeobox-derived short peptide is rapidly internalised by cultured neurones: a new basis for an efficient intracellular delivery system, *Biochem. Biophys. Res. Commun.* 214:685-93 (1995).

Brugnano et al., Cell penetrating peptides can exert biological activity: a review, *Biomol. Concepts.* 1:109-16 (2010).

Byun et al., Low molecular weight protamine: A potential nontoxic heparin antagonist, *Thrombosis Research.* 94:53-61 (1999).

Cardozo et al., Cell-permeable peptides induce dose- and length-dependent cytotoxic effects, *Biochim. Biophys. Acta.* 1769:2222-34 (2007).

Chiu et al., Assessment of neuroprotective peptides poly-arginine R18, COG1410, and APP96-110 experimental traumatic brain injury and in vitro neuronal excitotoxicity, *Translational Neuroscience.* 8:147-57 (2017).

Chiu et al., Poly-arginine peptide R18D reduces neuroinflammation and functional deficits following traumatic brain injury in the Long Evans Rat, International Journal of Peptide Research and Therapeutics (2019).

Colombo et al., The TAT-JNK inhibitor peptide interferes with beta amyloid protein stability, *Cell Death Differ.* 14:1845-8 (2007).

Corrigan et al., The neuroprotective activity of the amyloid precursor protein against traumatic brain injury is mediated via the heparin binding site in residues 96-110, *J. Neurochem.* 128:196-204 (2014).

Costa et al., Diagnosis, pathogenesis and therapeutic targets in amyotrophic lateral sclerosis, *CNS Neurol Disord Drug Targets.* 9:764-78 (2010).

Craig et al., Attenuation of neuronal death by peptide inhibitors of AP-1 activation in acute and delayed in vitro ischemia (Oxygen/Glucose Deprivation) models, *Int. J. Res. Ther.* 1-6 (2011).

Cruz-Haces et al., Pathological correlations between traumatic brain injury and chronic neurodegenerative diseases, *Transl. Neurodegener.* 6:1-20 (2017).

Deng et al., Presynaptic NMDA receptors control nociceptive transmission at the spinal cord level in neuropathic pain, *Cell Mol. Life Sci.* 76:1889-1899 (2019).

Doeppner et al., TAT-Hsp70-mediated neuroprotection and increased survival of neuronal precursor cells after focal cerebral ischemia in mice, *J. Cereb. Blood Flow Metab.* 29:1187-96 (2009).

Dolgin, To Serve and Neuroprotect Nature Medicine, pp. 1003-1006 (2012).

Edwards et al., Assessment of therapeutic window for poly-arginine-18D (R18D) in a P7 rat model of perinatal hypoxic-ischaemic encephalopathy, *J. Neurosci. Res.* 96:1816-26 (2018).

Edwards et al., Characterisation of neuroprotective efficacy of modified poly-arginine-9 (R9) peptides using a neuronal glutamic acid excitotoxicity model, *Mol. Cell. Biochem.* 426:75-85 (2017).

Edwards et al., Poly-arginine R18 and R18D (D-enantiomer) peptides reduce infarct volume and improve behavioural outcomes following perinatal hypoxic-ischaemic encephalopathy in the P7 rat, *Mol. Brain.* 11:1-12 (2018).

Endres et al., Ischemia and stroke, *Adv. Exp. Med. Biol.* 513:455-73 (2002).

Esposito et al., Amyloid β, glutamate, excitotoxicity in Alzheimer's disease: are we on the right track? *CNS Neurosci. Ther.* 19:549-55 (2013).

Ezza et al, Glutamate Excitotoxicity and Neurodegeneration, *J. Mol. Genet. Med.* 8:1-4 (2014).

Fernandes et al., NMDA Receptors and Huntington's Disease, Boca Raton, FL, CRC Press/Taylor & Francis, Chapter 2 (2009).

Frankel et al., Cellular uptake of the tat protein from human immunodeficiency virus, *Cell.* 55:1189-93 (1988).

Fujikawa, Prolonged seizures and cellular injury: understanding the connection, *Epilepsy Behav.* 3:S3-S11 (2005).

Gonzalez et al., NMDARs in neurological diseases: a potential therapeutic target, *Int. J. Neurosci.* 125:315-27 (2014).

Gopagondanahalli et al., Preterm Hypoxic-Ischemic Encephalopathy, *Front. Pediatr.* 4:1-10 (2016).

Green et al., Autonomous functional domains of chemically synthesized human immunodeficiency virus tat trans-activator protein, *Cell.* 55:1179-88 (1988).

Gromiha et al., Relationship between amino acid properties and functional parameters in olfactory receptors and discrimination of mutants with enhanced specificity, 2-9 (2011).

Gu et al., Apelin-36, a potent peptide, protects against ischemic brain injury by activating the PI3K/Akt pathway, *Neurochem. Int.* 63:535-40 (2013).

Hirose et al., Transient focal membrane deformation induced by arginine-rich peptides leads to their direct penetration into cells, *Mol. Ther.* 20:984-93 (2012).

Ho et al., Synthetic protein transduction domains: enhanced transduction potential in vitro and in vivo, *Cancer Res.* 61:474-477 (2001).

Hoque et al., A beacon of hope in stroke therapy—Blockade of pathologically activated cellular events in excitotoxic neuronal death as potential neuroprotective strategies, *Pharmacol. Ther.* 160:159-79 (2016).

Hu et al., Glutamate receptors in preclinical research on Alzheimer's disease: update on recent advances, *Pharmacol. Biochem. Behav.* 100:855-62 (2012).

Inquimbert et al., NMDA Receptor Activation Underlies the Loss of Spinal Dorsal Horn Neurons and the Transition to Persistent Pain after Peripheral Nerve Injury, *Cell Rep.* 23:2678-89 (2018).

Jaggi et al., Mechanisms in cancer-chemotherapeutic drugs-induced peripheral neuropathy, *Toxicology.* 291:1-9 (2012).

Jaiswal, Therapeutic opportunities and challenges of induced pluripotent stem cells-derived motor neurons for treatment of amyotrophic lateral sclerosis and motor neuron disease, *Neural. Regen. Res.* 12:723-736 (2017).

Kacprzak et al., Inhibition of furin by polyarginine-containing peptides: nanomolar inhibition by nona-D-arginine, *J. Biol. Chem.* 279:36788-94 (2004).

Kao et al., Opioids modulate post-ischemic progression in a rat model of stroke, *Neurochem. Int.* 52:1256-65 (2008).

Khalilpour et al., Ischemic optic neuropathy as a model of neurodegenerative disorder: A review of pathogenic mechanism of axonal degeneration and the role of neuroprotection, *J. Neurol. Sci.* 375:430-441 (2017).

Khangura et al., An integrated review on new targets in the treatment of neuropathic pain, *Korean J. Physiol. Pharmacol.* 23:1-20 (2019).

Kilic et al., Intravenous TAT-GDNF is protective after focal cerebral ischemia in mice, *Stroke.* 34:1304-10 (2003).

King et al., Excitotoxicity in ALS: Overstimulation, or overreaction? *Exp. Neurol.* 1:162-71 (2016).

Kocaeli et al., MK-801 improves neurological and histological outcomes after spinal cord ischemia induced by transient aortic cross-clipping in rats, *Surg. Neurol.* 2:S22-6 (2005).

(56) References Cited

OTHER PUBLICATIONS

Kocahan et al., Mechanisms of Alzheimer's Disease Pathogenesis and Prevention: The Brain, Neural Pathology, N-methyl-D-aspartate Receptors, Tau Protein and Other Risk Factors, *Clin. Psychopharmacol. Neurosci.* 15:1-8 (2017).
Kochanek et al., Emerging therapies in traumatic brain injury, *Semin. Neurol.* 35:83-100 (2015).
Kostandy, The role of glutamate in neuronal ischemic injury: the role of spark in fire, *Neurol Sci.* 33:223-37 (2012).
Lai et al., Selectively increasing inducible heat shock protein 70 via TAT-protein transduction protects neurons from nitrosative stress and excitotoxicity, *J. Neurochem.* 94:360-366 (2005).
Laskowitz et al., COG1410, a novel apolipoprotein E-based peptide, improves functional recovery in a murine model of traumatic brain injury, *J. Neurotrauma.* 24:1093-1107 (2007).
Leaw et al., Mitochondria, Bioenergetics and Excitotoxicity: New Therapeutic Targets in Perinatal Brain Injury, *Front Cell Neurosci.* 11:1-18 (2017).
Levite, Glutamate, T cells and multiple sclerosis, *J. Neural. Transm. (Vienna).* 124:775-798 (2017).
Lewerenz et al., Chronic Glutamate Toxicity in Neurodegenerative Diseases—What is the Evidence? *Front. Neurosci.* 9:1-20 (2015).
Li et al., New synthetic peptide with efficacy for heparin reversal and low toxicity and immunogenicity in comparison to protamine sulfate, *Biochemical and Biophysical Research Communications.* 467:497-502 (2015).
Liu et al., Neuroprotection of Tat-GluR6-9c against neuronal death induced by kainate in rat hippocampus via nuclear and non-nuclear pathways, *J. Biol. Chem.* 281:17432-45 (2006).
MacDougall et al., The Neuroprotective Peptide Poly-Arginine-12 (R12) Reduces Cell Surface Levels of NMDA NR2B Receptor Subunit in Cortical Neurons; Investigation into the Involvement of Endocytic Mechanisms, *J. Mol. Neurosci.* 61:235-46 (2017).
Mandolesi et al., Synaptopathy connects inflammation and neurodegeneration in multiple sclerosis, *Nat. Rev. Neurol.* 11:711-24 (2015).
Mathis et al., Current view and perspectives in amyotrophic lateral sclerosis, *Neural. Regen. Res.* 12:181-184 (2017).
Matsunaga et al., Nucleoprotamine diet derived from salmon soft roe protects mouse hippocampal neurons from delayed cell death after transient forebrain ischemia, *Neurosci. Res.* 47:269-76 (2003).
Mattson, Excitotoxic and excitoprotective mechanisms: abundant targets for the prevention and treatment of neurodegenerative disorders, *Neuromolecular Med.* 3:65-94 (2003).
McAdoo et al., Intrathecal administration of a novel apoE-derived therapeutic peptide improves outcome following perinatal hypoxic-ischemic injury, *Neurosci. Lett.* 381:305-8 (2005).
Meade et al., AP-1 inhibitory peptides are neuroprotective following acute glutamate excitotoxicity in primary cortical neuronal cultures, *J. Neurochem.* 112:258-70 (2010).
Meade et al., AP-1 inhibitory peptides attenuate in vitro cortical neuronal cell death induced by kainic acid, *Brain Res.* 1360:8-16 (2010).
Meade et al., The application of cell penetrating peptides for the delivery of neuroprotective peptides/proteins in experimental cerebral ischaemia studies, *J. Experimental Stroke Transl.* 22-40 (2009).
Mehta et al., Excitotoxicity: Bridge to various triggers in neurodegenerative disorders, *European Journal of Pharmacology.* 698:6-18 (2012).
Meloni et al., Assessment of the Neuroprotective effects of arginine-rich protamine peptides, poly-arginine peptides (R12-cyclic, R22) and arginine-tryptophan-containing peptides following in vitro excitotoxicity and/or permanent middle cerebral artery occlusion in rats, *Neuromol. Med.* 19:271-285 (2017).
Meloni et al., Characterisation of neuronal cell death in acute and delayed in vitro ischemia (oxygen-glucose deprivation) models, *J. Neurosci. Methods.* 195:67-74 (2011).
Meloni et al., Establishment of neuronal in vitro models of ischemia in 96-well microtiter strip-plates that result in acute, progressive and delayed neuronal death, *Neuroscience.* 108:17-26 (2001).
Meloni et al., Poly-arginine and arginine-rich peptides are neuroprotective in stroke models, *Journal of Cerebral Blood Flow & Metabolism.* 1-12 (2015).
Meloni et al., Poly-Arginine peptides R18 and R18D improve functional outcomes after endothelin-1-induced stroke in the sprague dawley rat, *J. Neuropathol. Exp. Neurol.* 78:426-35 (2019).
Meloni et al., The neuroprotective efficacy of cell-penetrating peptides TAT, penetratin, Arg-9, and Pep-1 in glutamic acid, kainic acid, and in vitro ischemia injury models using primary cortical neuronal cultures, *Cell Mol. Neurobiol.* 34:173-81 (2014).
Milani et al., Neuroprotective efficacy of poly-arginine R18 and NA-1 (TAT-NR2B9c) peptides following transient middle cerebral artery occlusion in the rat, *Neurosci. Res.* 114:9-15 (2017).
Milani et al., Poly-arginine peptides reduce infarct volume in a permanent middle cerebral artery rat stroke model, *BMC Neurosci.* 17:19 (2016).
Milani et al., The R18 poly-arginine peptide is more effective than the TAT-NR2B9c (NA-1) peptide when administered 60 minutes after permanent middle cerebral artery occlusion in the rat, *BMC Neuroscience.* 17:1-9 (2016).
Miller, Multiple sclerosis, *Adv. Exp. Med. Biol.* 724:222-38 (2012).
Milletti, Cell-penetrating peptides: classes, origin, and current landscape, *Drug Discov. Today.* 17:850-60 (2012).
Mitchell et al., Polyarginine enters cells more efficiently than other polycationic homopolymers, *J. Peptide Res.* 56:318-325 (2000).
Moschos et al., Lung delivery studies using siRNA conjugated to TAT(48-60) and penetratin reveal peptide induced reduction in gene expression and induction of innate immunity, *Bioconjug. Chem.* 18:1450-9 (2007).
Nagel et al., Tat-Hsp70 protects dopaminergic neurons in midbrain cultures and in the substantia nigra in models of Parkinson's disease, *J. Neurochem.* 105:853-64 (2008).
Nath et al., Identification of a human immunodeficiency virus type 1 Tat epitope that is neuroexcitatory and neurotoxic, *J. Virol.* 70:1475-80 (1996).
Ogawa et al., Protein therapy using heme-oxygenase-1 fused to a polyarginine transduction domain attenuates cerebral vasospasm after experimental subarachnoid hemorrhage, *J. Cereb. Blood Flow Metab.* 31:2231-42 (2011).
Ong et al., Slow excitotoxicity in Alzheimer's disease, *J. Alzheimers Dis.* 35:643-68 (2013).
Osikowicz et al., The glutamatergic system as a target for neuropathic pain relief, *Exp. Physiol.* 98:372-84 (2013).
Palm-Apergi et al., Do cell-penetrating peptides actually "penetrate" cellular membranes? *Mol. Ther.* 20:695-7 (2012).
Prabhakar et al., References related to excitotoxicity in acute and chronic Neurodegenerative disorders, p. 1-5 (2012).
Protamine II-1, Uniprot Q7LzB5, accessed on Jan. 4, 2017, Uniprot Protein Database.
Quillinan et al., Neuropathophysiology of Brain Injury, *Anesthesiol. Clin.* 34:453-64 (2016).
Righy et al., Molecular, Cellular and Clinical Aspects of Intracerebral Hemorrhage: Are the Enemies Within? *Curr. Neuropharmacol.* 14:392-402 (2016).
Rowland et al., Current status of acute spinal cord injury pathophysiology and emerging therapies: promise on the horizon, *Neurosurg. Focus.* 25:E2 (2008).
Ruan et al., Current status of auditory aging and anti-aging research, *Geriatr. Gerontol. Int.* 14:40-53 (2014).
Salinska et al., The role of excitotoxicity in neurodegeneration, *Folia Neuropathol.* 43:322-39 (2005).
Schmidt et al., Neurodegenerative diseases of the retina and potential for protection and recovery, *Curr. Neuropharmacol.* 6:164-78 (2008).
Schultz, Update on the pathogenesis of Parkinson's disease, *J. Neurol.* 255 Suppl 5:3-7 (2008).
Sebe et al., Ca2+-Permeable AMPARs Mediate Glutamatergic Transmission and Excitotoxic Damage at the Hair Cell Ribbon Synapse, *J. Neurosci.* 37:6162-6175 (2017).
Sepers et al., Mechanisms of synaptic dysfunction and excitotoxicity in Huntington's disease, *Drug Discov. Today.* 19:990-6 (2014).
Shahinian et al., Proteomic identification of protease cleavage sites: cell-biological and biomedical applications, 420-433 (2017).

(56) References Cited

OTHER PUBLICATIONS

Sheets, Excessive activation of ionotropic glutamate receptors induces apoptotic hair-cell death independent of afferent and efferent innervation, *Scientific Reports.* 1-14 (2016).

Siddiqui et al., Translating mechanisms of neuroprotection, regeneration, and repair to treatment of spinal cord injury, *Prog. Brain Res.* 218:15-54 (2015).

Sriram et al., Experimental allergic encephalomyelitis: a misleading model of multiple sclerosis, *Ann. Neurol.* 58:939-45 (2005).

Steinman et al., How to successfully apply animal studies in experimental allergic encephalomyelitis to research on multiple sclerosis, *Ann. Neurol.* 60:12-21 (2006).

Sun et al., Proteolytic characteristics of Cathespin D related to the recognition and cleavage of its target proteins, 1-10.

Taoufik et al., Ischemic neuronal damage, *Curr. Pharm. Des.* 14:3565-73 (2008).

The On-Line Medical Dictionary, pp. 1-2, Definition of analog, acessed on Jul. 7, 2005.

Towfighi et al., Treatment and prevention of primary intracerebral hemorrhage, *Semin. Neurol.* 25:445-52 (2005).

Tunnemann et al., Live-Cell analysis of cell penetration ability and toxicity of oligo-arginines, *J. Pept. Sci.* 14:469-476 (2008).

Uncini et al., Nodopathies of the peripheral nerve: an emerging concept, *J. Neurol. Neurosurg. Psychiatry.* 86:1186-95 (2015).

Uniprot Protein Database, Protein Accession L7MDK2, accessed on Jun. 7, 2017.

Vaslin et al., Unconjugated TAT carrier peptide protects against excitotoxicity, *Neurotox. Res.* 15:123-126 (2009).

Vile et al., Chronic Traumatic Encephalopathy: The cellular sequela to repetitive brain injury, *J. Clin. Neurosci.* 41:24-29 (2017).

Willmot et al., A systematic review of nitric oxide donors and L-arginine in experimental stroke; effects on infarct size and cerebral blood flow, *Nitric Oxide.* 12:141-9 (2005).

Wing et al., Proteins containing peptide sequences related to Lys-Phe-Glu-Arg-Gln are selectively depleted in liver and heart, but not skeletal muscle, of fasted rats, *Biochem. J.* 275:165-169 (1991).

Witiw et al., Acute Spinal Cord Injury, *J. Spinal Disord. Tech.* 28:202-10 (2015).

Xu et al., Neuroprotection by cell permeable TAT-mGluR1 peptide in ischemia: synergy between carrier and cargo sequences, *Neuroscientist.* 14:409-14 (2008).

Yi et al., Excitotoxic mechanisms and the role of astrocytic glutamate transporters in traumatic brain injury, *Neurochem. Int.* 48:394-403 (2006).

Yildiz et al., Neonatal hypoxic ischemic encephalopathy: an update on disease pathogenesis and treatment, *Expert Rev. Neurother.* 17:449-459 (2017).

Zhang et al., Critical role of increased PTEN nuclear translocation in excitotoxic and ischemic neuronal injuries, *J. Neurosci.* 33:7997-8008 (2013).

Milani et al., Comparison of neuroprotective efficacy of poly-arginine R18 and R18D (D-enantiomer) peptides following permanent middle cerebral artery occlusion in the Wistar rat and in vitro toxicity studies, *PLoS One.* 13:e019884 (2018).

Milani et al., Comparative Assessment of the Proteolytic Stability and Impact of Poly-Arginine Peptides R18 and R18D on Infarct Growth and Penumbral Tissue Preservation Following Middle Cerebral Artery Occlusion in the Sprague Dawley Rat, *Neurochem. Res.* 46:1166-76 (2021).

* cited by examiner

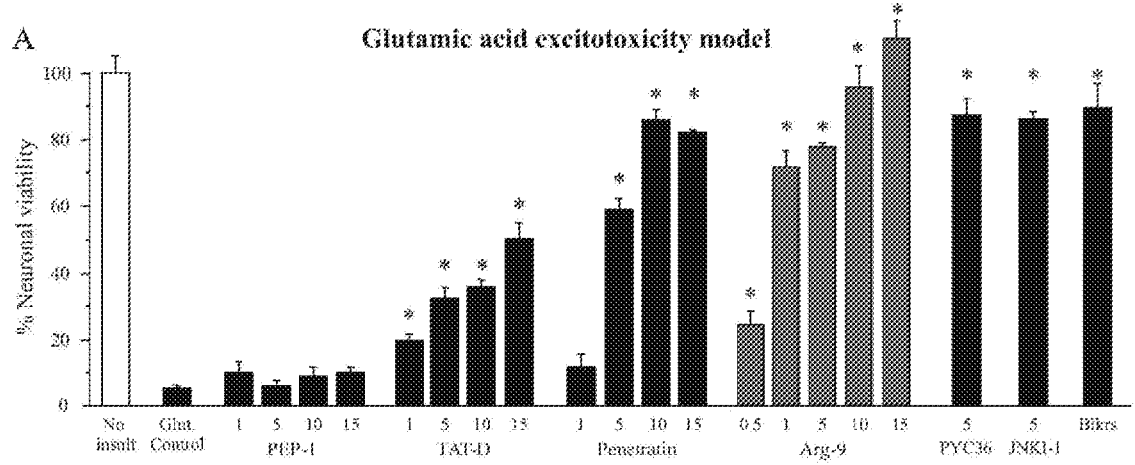
Fig.1.a
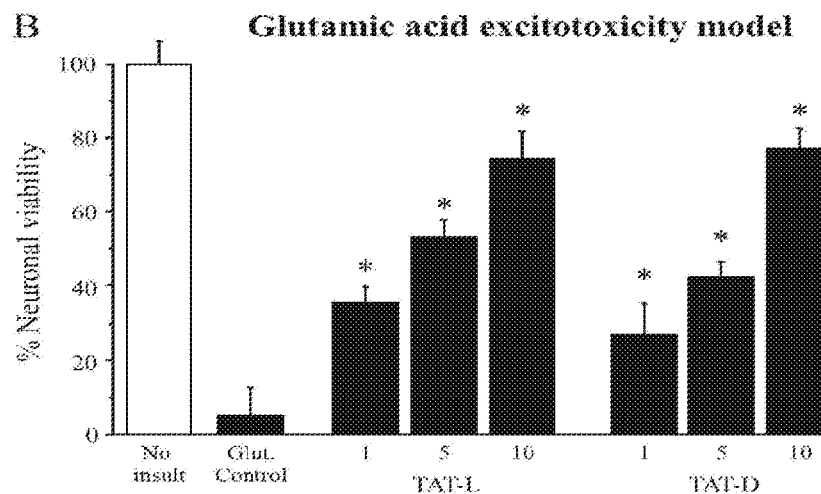
Fig. 1.b
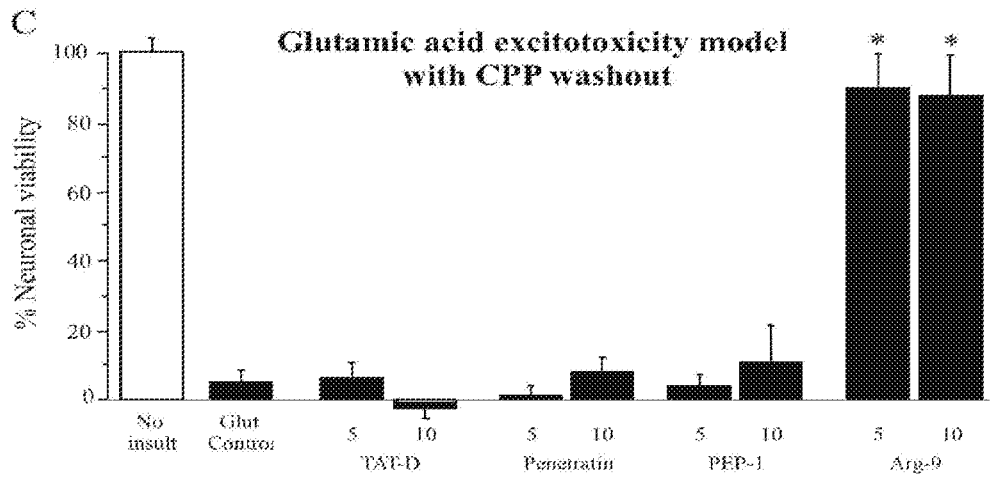
Fig. 1.c

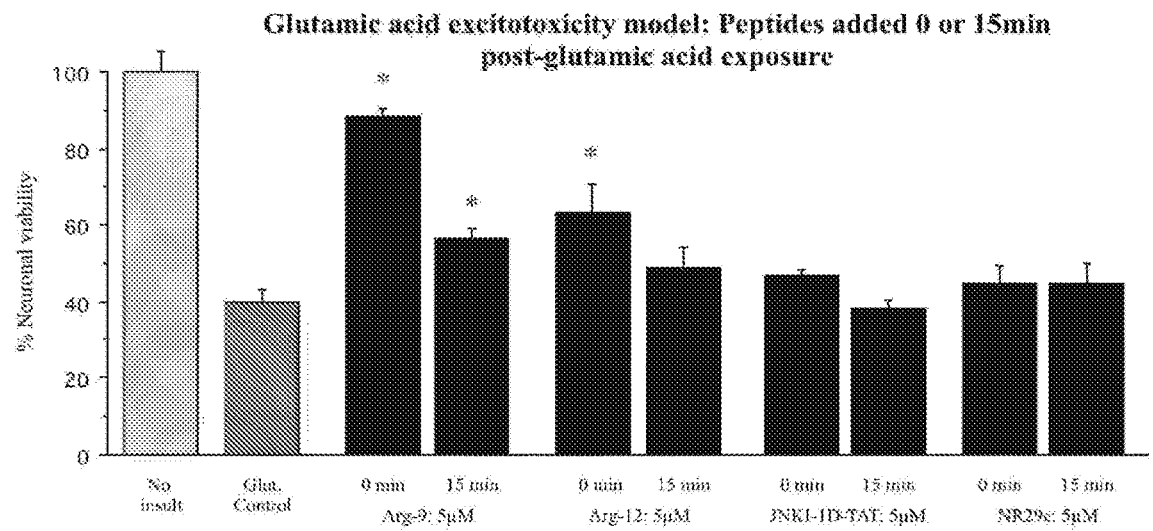
Fig. 1.d
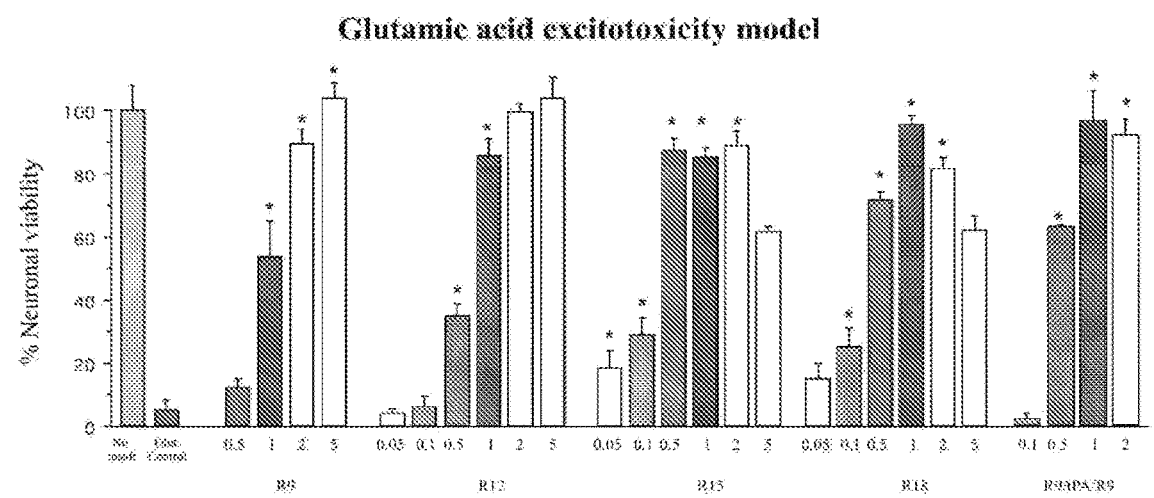
Fig. 1.e
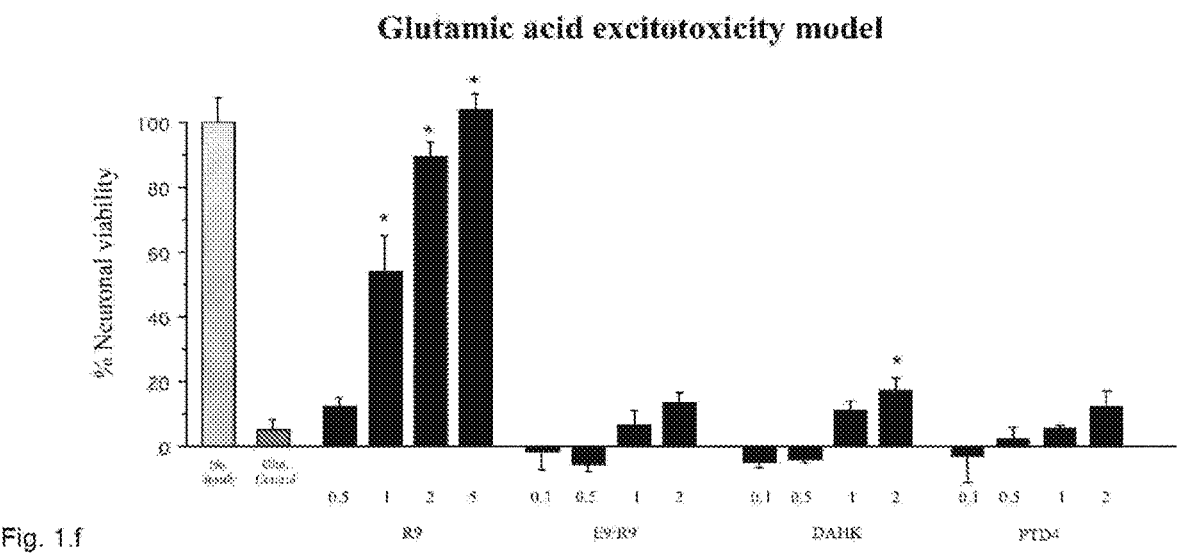
Fig. 1.f

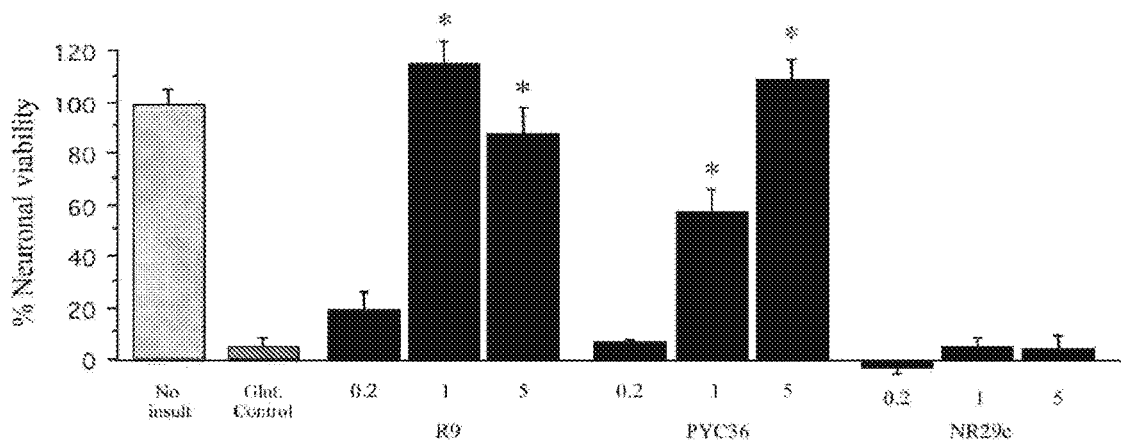
Fig. 1.g
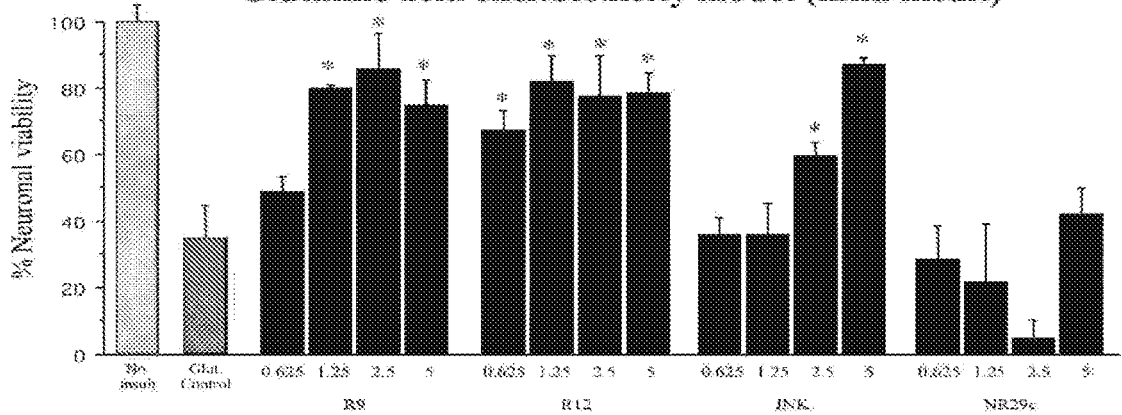
Fig. 1.h
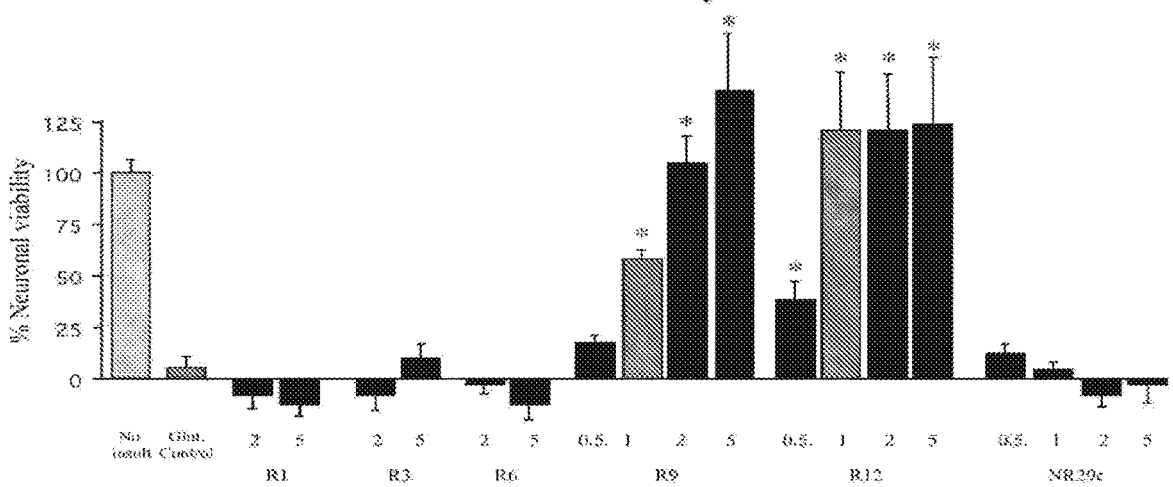
Fig. 1.i

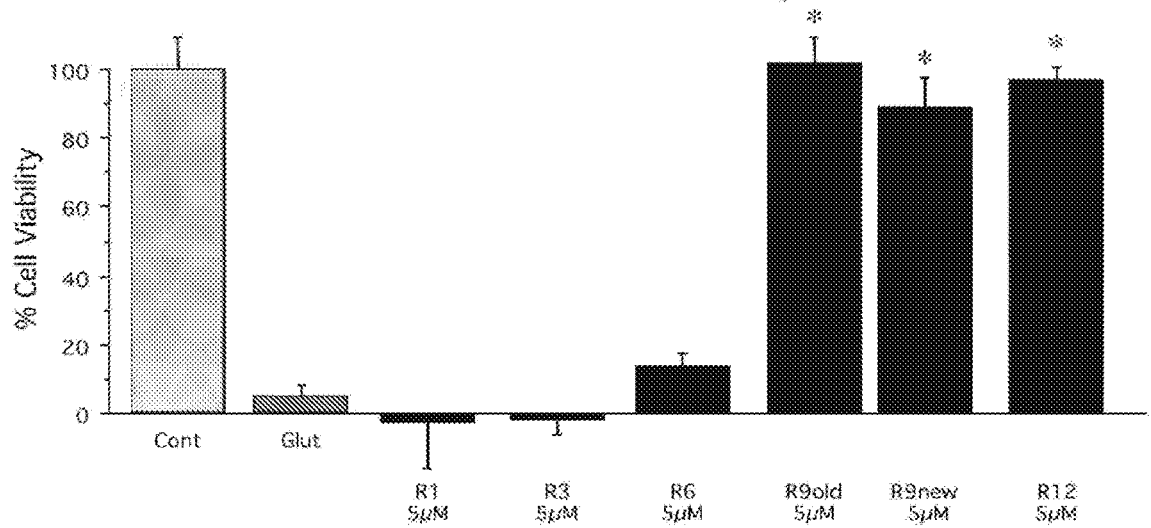
Fig. 1.j
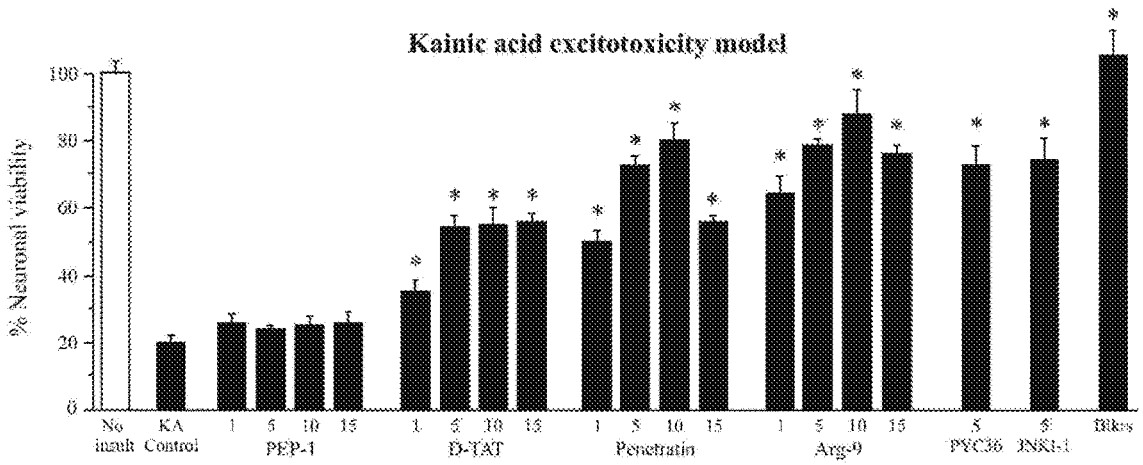
Fig. 2
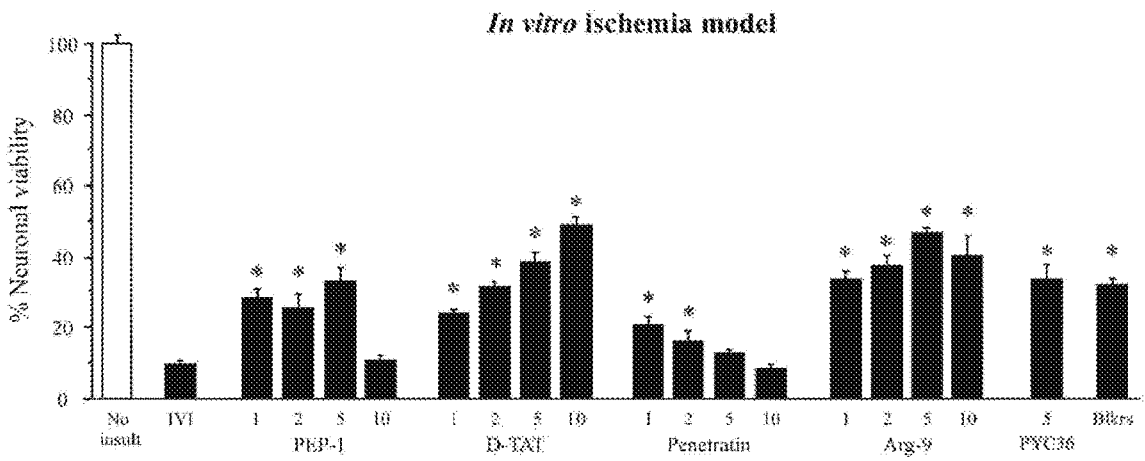
Fig. 3a

| Peptide | SEQ ID NO. | Sequence | No. amino acids/No. arginine residues; molecular weight (Da) | Net charge at pH 7 | Physical-chemical properties |
|---|---|---|---|---|---|
| R1: Arg-1 | 1 | H-R-OH | 1/1: 174 | 1 | Cationic |
| R3: Arg-3 | 2 | H-RRR-OH | 3/3: 487 | 3 | Cationic |
| R6: Arg-6 | 3 | H-RRRRRR-OH | 6/6: 955 | 6 | Cationic |
| R7: Arg-7 | 4 | H-RRRRRRR-OH | 7/7: 1,111 | 7 | Cationic |
| R8: Arg-8 | 5 | H-RRRRRRRR-OH | 8/8: 1,267 | 8 | Cationic |
| R9: Arg-9 | 6 | H-RRRRRRRRR-OH | 9/9: 1,424 | 9 | Cationic |
| R10: Arg-10 | 7 | H-RRRRRRRRRR-OH | 10/10: 1,580 | 10 | Cationic |
| R11: Arg-11 | 8 | H-RRRRRRRRRRR-OH | 11/11: 1,736 | 11 | Cationic |
| R12: Arg-12 | 9 | H-RRRRRRRRRRRR-OH | 12/12: 1,892 | 12 | Cationic |
| R13: Arg-13 | 10 | H-RRRRRRRRRRRRR-OH | 13/13: 2,048 | 13 | Cationic |
| R14: Arg-14 | 11 | H-RRRRRRRRRRRRRR-OH | 14/14: 2,204 | 14 | Cationic |
| R15: Arg-15 | 12 | H-RRRRRRRRRRRRRRR-OH | 15/15: 2,360 | 15 | Cationic |
| R18: Arg-18 | 13 | H-RRRRRRRRRRRRRRRRRR-OH | 18/18: 2,829 | 18 | Cationic |
| PTD-4[a] | 14 | H-YARAAARQARA-OH | 11/3: 1,204 | 3 | Cationic |
| E9/R9 (R9/E9) | 15 | H-EEEEEEEEE-RRRRRRRRR-OH | 18/9: 2,586 | 0 | Neutral |
| R9/tPA/R9 or R9/X7/R9 | 16 | H-RRRRRRRRR-PGRVVGG-RRRRRRRRR-OH | 25/19: 3,452 | 19 | Cationic |
| DAHK | 17 | H-DAHK-OH | 4/0: 469.5 | 0.1 | N/A |
| NR2B9c-TAT[b] | 18 | H-GRKKRRQRRR-KLSSIESDV-NH2 | 19/6: 2,355 | | Cationic |
| D-R9 | 19 | H-rrrrrrrrr-NH2 | 9/9: 1423.73 | 10 | Cationic |
| TAT-D | 20 | H-Grrrqrrkkrg-NH2 | 10/6: 1,453 | 9 | Cationic |
| TAT-L | 21 | Ac-GRKKRRQRRRG-NH2 | 10/6: 1,494 | 8 | Cationic |
| Penetratin | 22 | H-RQIKIWFQNRRMKWKK-NH2 | 16/3: 2,246 | 7 | Cationic |
| Pep-1 | 23 | H-KETWWETWWTEWSQPKKKRKV-NH2 | 21/1: 2,847 | 4 | Amphiphilic |
| PYC36L-TAT[c] | 24 | H-GRKKRRQRRR-GGLQGRRRQGYQSIKP-NH2 | 26/10: 3,180 | 13 | Cationic |
| JNKI-1D-TAT[d] | 25 | H-tdqsrpvqpflnlttprkprpp-rrrqrrkkrG-NH2 | 32/: 3,925 | 12 | Cationic |
| TAT-JNKI-1[d] | 26 | H-GRKKRRQRRR-PPRPKRPTTLNLFPQVPRSQDT-OH | 32/9: 3,924.6 | 11 | Cationic |
| kFGF-JNKI-1 | 27 | H-AAVALLPAVLLALLAP-PPRPKRPTTLNLFPQVPRSQDT-OH | 38/3: 4,043.9 | 3 | Hydrophobic |
| kFGF | 28 | H-AAVALLPAVLLALLAP-OH | 16/0: 1515.96 | 0 | Hydrophobic |
| XIP[e] | 29 | H-RRLLFYKYVYKRYRAGKQRG-OH | 20/5: 2621.14 | 8 | Cationic |
| NCXBP3[f] | 30 | H-RRERRRRSCAGCSRARGSCRSCRR-NH2 | 24/11: 2881.34 | 10.8 | Cationic |
| Cal/R9 | 31 | Ac-PLFAE-RRRRRRRRR-NH2 | 15/9: 2022.41 | 8 | Cationic |

Fig. 46

Summary of different protamine (salmon) peptides (and nucleic acid)

| SEQ ID NO.: | Name of Sequence | Type | Other information | Sequence | aa's/arg residues | MW (da) |
|---|---|---|---|---|---|---|
| - | Protamine sulphate mixture; Ptm | Poly-peptide mixture | Injectable/IV form | Protamine 1 - Protamine 4[1] | 32/21 | ≈4,500 |
| 32 | Protamine 1; Ptm1 | Poly-peptide | Peak 1 HPLC | PRRRRRSSSRPIRRRRR PRASRRRRRGGRRRR | 32/21 | 4,236 |
| 33 | Protamine 2; Ptm2 | Poly-peptide | Peak 2 HPLC | PRRRRSSRRPVRRRRR PRVSRRRRRGGRRRR | 31/21 | 4,163 |
| 34 | Protamine 3; Ptm3 | Poly-peptide | Peak 3 HPLC | PRRRRSSSRPVRRRRR PRVSRRRRRGGRRRR | 31/20 | 4,094 |
| 35 | Protamine 4; Ptm4 | Poly-peptide | Peak 4 HPLC | PRRRRASRRIRRRRRPR VSRRRRRGGRRRR | 30/21 | 4,064 |
| 36 | Protamine 5; Ptm5 | Poly-peptide | SwissProt | PRRRRSSSRPVRRRRR PRVSRRRRRGGRRRR | 32/21 | 4,250 |
| 37 | Low molecular weight protamine (LMWP) | Poly-peptide | Derived from protamine | VSRRRRRGGRRRR | 14/10 | 1,880 |
| 38 | Protamine 5 nucleotide sequence | Ptm 5, DNA coding sequence | SwissProt | 5'ATGCCCAGAAGACGC AGATCCTCCAGCCGAC CTGTCCGCAGGCGCCG CCGCCCTAGGGTGTCC CGACGTCGTCGCAGGA GAGGAGGCCGCAGGA GGCGT-3' | N/A | N/A |

Fig. 47

SEQUENCE LISTING

```
<160> NUMBER OF SEQ ID NOS: 46

<210> SEQ ID NO 1
<211> LENGTH: 1
<212> TYPE: PRT
<213> ORGANISM: ARTIFICIAL
<220> FEATURE:
<223> OTHER INFORMATION: ARG-1

<400> SEQUENCE: 1

Arg
1

<210> SEQ ID NO 2
<211> LENGTH: 3
<212> TYPE: PRT
<213> ORGANISM: ARTIFICIAL
<220> FEATURE:
<223> OTHER INFORMATION: ARG-3

<400> SEQUENCE: 2

Arg Arg Arg
1

<210> SEQ ID NO 3
<211> LENGTH: 6
<212> TYPE: PRT
<213> ORGANISM: ARTIFICIAL
<220> FEATURE:
<223> OTHER INFORMATION: ARG-6

<400> SEQUENCE: 3

Arg Arg Arg Arg Arg Arg
1               5

<210> SEQ ID NO 4
<211> LENGTH: 7
<212> TYPE: PRT
```

```
<213> ORGANISM: ARTIFICIAL
<220> FEATURE:
<223> OTHER INFORMATION: ARG-7

<400> SEQUENCE: 4

Arg Arg Arg Arg Arg Arg Arg
1               5

<210> SEQ ID NO 5
<211> LENGTH: 8
<212> TYPE: PRT
<213> ORGANISM: ARTIFICIAL
<220> FEATURE:
<223> OTHER INFORMATION: ARG-8

<400> SEQUENCE: 5

Arg Arg Arg Arg Arg Arg Arg Arg
1               5

<210> SEQ ID NO 6
<211> LENGTH: 9
<212> TYPE: PRT
<213> ORGANISM: ARTIFICIAL
<220> FEATURE:
<223> OTHER INFORMATION: ARG-9

<400> SEQUENCE: 6

Arg Arg Arg Arg Arg Arg Arg Arg Arg
1               5

<210> SEQ ID NO 7
<211> LENGTH: 10
<212> TYPE: PRT
<213> ORGANISM: ARTIFICIAL
<220> FEATURE:
<223> OTHER INFORMATION: ARG-10

<400> SEQUENCE: 7

Arg Arg Arg Arg Arg Arg Arg Arg Arg Arg
1               5                   10

<210> SEQ ID NO 8
<211> LENGTH: 11
<212> TYPE: PRT
<213> ORGANISM: ARTIFICIAL
<220> FEATURE:
<223> OTHER INFORMATION: ARG-11

<400> SEQUENCE: 8

Arg Arg Arg Arg Arg Arg Arg Arg Arg Arg
1               5                   10

<210> SEQ ID NO 9
<211> LENGTH: 12
<212> TYPE: PRT
<213> ORGANISM: ARTIFICIAL
<220> FEATURE:
<223> OTHER INFORMATION: ARG-12

<400> SEQUENCE: 9

Arg Arg Arg Arg Arg Arg Arg Arg Arg Arg Arg
1               5                   10

<210> SEQ ID NO 10
<211> LENGTH: 13
<212> TYPE: PRT
<213> ORGANISM: ARTIFICIAL
```

```
<220> FEATURE:
<223> OTHER INFORMATION: ARG-13

<400> SEQUENCE: 10

Arg Arg Arg Arg Arg Arg Arg Arg Arg Arg Arg Arg
1               5                   10

<210> SEQ ID NO 11
<211> LENGTH: 14
<212> TYPE: PRT
<213> ORGANISM: ARTIFICIAL
<220> FEATURE:
<223> OTHER INFORMATION: ARG-14

<400> SEQUENCE: 11

Arg Arg Arg Arg Arg Arg Arg Arg Arg Arg Arg Arg Arg Arg
1               5                   10

<210> SEQ ID NO 12
<211> LENGTH: 15
<212> TYPE: PRT
<213> ORGANISM: ARTIFICIAL
<220> FEATURE:
<223> OTHER INFORMATION: ARG-15

<400> SEQUENCE: 12

Arg Arg Arg Arg Arg Arg Arg Arg Arg Arg Arg Arg Arg Arg Arg
1               5                   10                  15

<210> SEQ ID NO 13
<211> LENGTH: 18
<212> TYPE: PRT
<213> ORGANISM: ARTIFICIAL
<220> FEATURE:
<223> OTHER INFORMATION: ARG-18

<400> SEQUENCE: 13

Arg Arg Arg Arg Arg Arg Arg Arg Arg Arg Arg Arg Arg Arg Arg Arg
1               5                   10                  15

Arg Arg

<210> SEQ ID NO 14
<211> LENGTH: 11
<212> TYPE: PRT
<213> ORGANISM: ARTIFICIAL
<220> FEATURE:
<223> OTHER INFORMATION: PTD-4

<400> SEQUENCE: 14

Tyr Ala Arg Ala Ala Ala Arg Gln Ala Arg Ala
1               5                   10

<210> SEQ ID NO 15
<211> LENGTH: 18
<212> TYPE: PRT
<213> ORGANISM: ARTIFICIAL
<220> FEATURE:
<223> OTHER INFORMATION: E9/R9

<400> SEQUENCE: 15

Glu Glu Glu Glu Glu Glu Glu Glu Glu Arg Arg Arg Arg Arg Arg
1               5                   10                  15

Arg Arg

<210> SEQ ID NO 16
```

```
<211> LENGTH: 25
<212> TYPE: PRT
<213> ORGANISM: ARTIFICIAL
<220> FEATURE:
<223> OTHER INFORMATION: R9/tPA/R9

<400> SEQUENCE: 16

Arg Arg Arg Arg Arg Arg Arg Arg Arg Pro Gly Arg Val Val Gly Gly
1               5                   10                  15

Arg Arg Arg Arg Arg Arg Arg Arg Arg
            20                  25

<210> SEQ ID NO 17
<211> LENGTH: 4
<212> TYPE: PRT
<213> ORGANISM: ARTIFICIAL
<220> FEATURE:
<223> OTHER INFORMATION: DAHK

<400> SEQUENCE: 17

Asp Ala His Lys
1

<210> SEQ ID NO 18
<211> LENGTH: 19
<212> TYPE: PRT
<213> ORGANISM: ARTIFICIAL
<220> FEATURE:
<223> OTHER INFORMATION: NR2B9c-TAT

<400> SEQUENCE: 18

Gly Arg Lys Lys Arg Arg Gln Arg Arg Lys Leu Ser Ser Ile Glu
1               5                   10                  15

Ser Asp Val

<210> SEQ ID NO 19
<211> LENGTH: 9
<212> TYPE: PRT
<213> ORGANISM: ARTIFICIAL
<220> FEATURE:
<223> OTHER INFORMATION: D-R9

<400> SEQUENCE: 19

Arg Arg Arg Arg Arg Arg Arg Arg Arg
1               5

<210> SEQ ID NO 20
<211> LENGTH: 11
<212> TYPE: PRT
<213> ORGANISM: Human immunodeficiency virus

<400> SEQUENCE: 20

Gly Arg Arg Arg Gln Arg Arg Lys Lys Arg Gly
1               5                   10

<210> SEQ ID NO 21
<211> LENGTH: 11
<212> TYPE: PRT
<213> ORGANISM: Human immunodeficiency virus

<400> SEQUENCE: 21

Gly Arg Lys Lys Arg Arg Gln Arg Arg Arg Gly
1               5                   10

<210> SEQ ID NO 22
```

```
<211> LENGTH: 16
<212> TYPE: PRT
<213> ORGANISM: Drosophila melanogaster

<400> SEQUENCE: 22

Arg Gln Ile Lys Ile Trp Phe Gln Asn Arg Arg Met Lys Trp Lys Lys
1               5                   10                  15

<210> SEQ ID NO 23
<211> LENGTH: 21
<212> TYPE: PRT
<213> ORGANISM: ARTIFICIAL
<220> FEATURE:
<223> OTHER INFORMATION: PEP-1

<400> SEQUENCE: 23

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 24
<211> LENGTH: 26
<212> TYPE: PRT
<213> ORGANISM: ARTIFICIAL
<220> FEATURE:
<223> OTHER INFORMATION: PYC36L-TAT

<400> SEQUENCE: 24

Gly Arg Lys Lys Arg Arg Gln Arg Arg Gly Gly Leu Gln Gly Arg
1               5                   10                  15

Arg Arg Gln Gly Tyr Gln Ser Ile Lys Pro
            20                  25

<210> SEQ ID NO 25
<211> LENGTH: 32
<212> TYPE: PRT
<213> ORGANISM: ARTIFICIAL
<220> FEATURE:
<223> OTHER INFORMATION: JNKI-1D-TAT

<400> SEQUENCE: 25

Thr Asp Gln Ser Arg Pro Val Gln Pro Phe Leu Asn Leu Thr Thr Pro
1               5                   10                  15

Arg Lys Pro Arg Pro Pro Arg Arg Arg Gln Arg Arg Lys Lys Arg Gly
            20                  25                  30

<210> SEQ ID NO 26
<211> LENGTH: 32
<212> TYPE: PRT
<213> ORGANISM: ARTIFICIAL
<220> FEATURE:
<223> OTHER INFORMATION: TAT-JNKI-1

<400> SEQUENCE: 26

Gly Arg Lys Lys Arg Arg Gln Arg Arg Arg Pro Pro Arg Pro Lys Arg
1               5                   10                  15

Pro Thr Thr Leu Asn Leu Phe Pro Gln Val Pro Arg Ser Gln Asp Thr
            20                  25                  30

<210> SEQ ID NO 27
<211> LENGTH: 38
<212> TYPE: PRT
<213> ORGANISM: ARTIFICIAL
<220> FEATURE:
```

<223> OTHER INFORMATION: kFGF-JNKI

<400> SEQUENCE: 27

Ala Ala Val Ala Leu Leu Pro Ala Val Leu Ala Leu Leu Ala Pro
1               5                   10                  15

Pro Pro Arg Pro Lys Arg Pro Thr Thr Leu Asn Leu Phe Pro Gln Val
            20                  25                  30

Pro Arg Ser Gln Asp Thr
        35

<210> SEQ ID NO 28
<211> LENGTH: 16
<212> TYPE: PRT
<213> ORGANISM: ARTIFICIAL
<220> FEATURE:
<223> OTHER INFORMATION: kFGF

<400> SEQUENCE: 28

Ala Ala Val Ala Leu Leu Pro Ala Val Leu Ala Leu Leu Ala Pro
1               5                   10                  15

<210> SEQ ID NO 29
<211> LENGTH: 20
<212> TYPE: PRT
<213> ORGANISM: ARTIFICIAL
<220> FEATURE:
<223> OTHER INFORMATION: XIP

<400> SEQUENCE: 29

Arg Arg Leu Leu Phe Tyr Lys Tyr Val Tyr Lys Arg Tyr Arg Ala Gly
1               5                   10                  15

Lys Gln Arg Gly
        20

<210> SEQ ID NO 30
<211> LENGTH: 24
<212> TYPE: PRT
<213> ORGANISM: ARTIFICIAL
<220> FEATURE:
<223> OTHER INFORMATION: NCXBP3

<400> SEQUENCE: 30

Arg Arg Glu Arg Arg Arg Ser Cys Ala Gly Cys Ser Arg Ala Arg
1               5                   10                  15

Gly Ser Cys Arg Ser Cys Arg Arg
        20

<210> SEQ ID NO 31
<211> LENGTH: 14
<212> TYPE: PRT
<213> ORGANISM: ARTIFICIAL
<220> FEATURE:
<223> OTHER INFORMATION: Cal/R9

<400> SEQUENCE: 31

Pro Leu Phe Ala Glu Arg Arg Arg Arg Arg Arg Arg Arg
1               5                   10

<210> SEQ ID NO 32
<211> LENGTH: 32
<212> TYPE: PRT
<213> ORGANISM: Oncorhynchus keta

```
<400> SEQUENCE: 32

Pro Arg Arg Arg Arg Ser Ser Ser Arg Pro Ile Arg Arg Arg
1               5                   10                  15

Arg Pro Arg Ala Ser Arg Arg Arg Arg Gly Gly Arg Arg Arg
            20                  25              30

<210> SEQ ID NO 33
<211> LENGTH: 31
<212> TYPE: PRT
<213> ORGANISM: Oncorhynchus keta

<400> SEQUENCE: 33

Pro Arg Arg Arg Arg Ser Ser Arg Arg Pro Val Arg Arg Arg
1               5                   10                  15

Pro Arg Val Ser Arg Arg Arg Arg Gly Gly Arg Arg Arg
            20                  25              30

<210> SEQ ID NO 34
<211> LENGTH: 31
<212> TYPE: PRT
<213> ORGANISM: Oncorhynchus keta

<400> SEQUENCE: 34

Pro Arg Arg Arg Arg Ser Ser Ser Arg Pro Val Arg Arg Arg
1               5                   10                  15

Pro Arg Val Ser Arg Arg Arg Arg Gly Gly Arg Arg Arg
            20                  25              30

<210> SEQ ID NO 35
<211> LENGTH: 30
<212> TYPE: PRT
<213> ORGANISM: Oncorhynchus keta

<400> SEQUENCE: 35

Pro Arg Arg Arg Arg Ala Ser Arg Arg Ile Arg Arg Arg Arg Pro
1               5                   10                  15

Arg Val Ser Arg Arg Arg Arg Gly Gly Arg Arg Arg Arg
            20                  25              30

<210> SEQ ID NO 36
<211> LENGTH: 32
<212> TYPE: PRT
<213> ORGANISM: Oncorhynchus keta

<400> SEQUENCE: 36

Pro Arg Arg Arg Arg Ser Ser Ser Arg Pro Val Arg Arg Arg
1               5                   10                  15

Pro Arg Val Ser Arg Arg Arg Arg Arg Gly Gly Arg Arg Arg
            20                  25              30

<210> SEQ ID NO 37
<211> LENGTH: 14
<212> TYPE: PRT
<213> ORGANISM: Oncorhynchus keta

<400> SEQUENCE: 37

Val Ser Arg Arg Arg Arg Arg Arg Gly Gly Arg Arg Arg Arg
1               5                   10

<210> SEQ ID NO 38
<211> LENGTH: 99
```

<212> TYPE: DNA
<213> ORGANISM: Oncorhynchus keta

<400> SEQUENCE: 38
atgcccagaa gacgcagatc ctccagccga cctgtccgca ggcgccgccg ccctagggtg    60
tcccgacgtc gtcgcaggag aggaggccgc aggaggcgt    99

<210> SEQ ID NO 39
<211> LENGTH: 16
<212> TYPE: PRT
<213> ORGANISM: ARTIFICIAL
<220> FEATURE:
<223> OTHER INFORMATION: Arg-16

<400> SEQUENCE: 39

Arg Arg Arg Arg Arg Arg Arg Arg Arg Arg Arg Arg Arg Arg Arg Arg
1               5                   10                  15

<210> SEQ ID NO 40
<211> LENGTH: 17
<212> TYPE: PRT
<213> ORGANISM: ARTIFICIAL
<220> FEATURE:
<223> OTHER INFORMATION: Arg-17

<400> SEQUENCE: 40

Arg Arg Arg Arg Arg Arg Arg Arg Arg Arg Arg Arg Arg Arg Arg Arg
1               5                   10                  15

Arg

<210> SEQ ID NO 41
<211> LENGTH: 22
<212> TYPE: PRT
<213> ORGANISM: ARTIFICIAL
<220> FEATURE:
<223> OTHER INFORMATION: Arg-22

<400> SEQUENCE: 41

Arg Arg Arg Arg Arg Arg Arg Arg Arg Arg Arg Arg Arg Arg Arg Arg
1               5                   10                  15

Arg Arg Arg Arg Arg Arg
            20

<210> SEQ ID NO 42
<211> LENGTH: 10
<212> TYPE: PRT
<213> ORGANISM: ARTIFICIAL
<220> FEATURE:
<223> OTHER INFORMATION: Lys-10

<400> SEQUENCE: 42

Lys Lys Lys Lys Lys Lys Lys Lys Lys Lys
1               5                   10

<210> SEQ ID NO 43
<211> LENGTH: 14
<212> TYPE: PRT
<213> ORGANISM: ARTIFICIAL
<220> FEATURE:
<223> OTHER INFORMATION: AM8D-TAT

<400> SEQUENCE: 43

Pro Lys Ile Gly Arg Lys Lys Arg Arg Gln Arg Arg Arg Gly
1               5                   10

```
<210> SEQ ID NO 44
<211> LENGTH: 24
<212> TYPE: PRT
<213> ORGANISM: ARTIFICIAL
<220> FEATURE:
<223> OTHER INFORMATION: R9-CBD3

<400> SEQUENCE: 44

Arg Arg Arg Arg Arg Arg Arg Arg Arg Ala Arg Ser Arg Leu Ala Glu
1               5                   10                  15

Leu Arg Gly Val Pro Arg Gly Leu
            20

<210> SEQ ID NO 45
<211> LENGTH: 26
<212> TYPE: PRT
<213> ORGANISM: ARTIFICIAL
<220> FEATURE:
<223> OTHER INFORMATION: TAT-CBD3

<400> SEQUENCE: 45

Tyr Gly Arg Lys Lys Arg Arg Gln Arg Arg Ala Arg Ser Arg Leu
1               5                   10                  15

Ala Glu Leu Arg Gly Val Pro Arg Gly Leu
            20                  25

<210> SEQ ID NO 46
<211> LENGTH: 4
<212> TYPE: PRT
<213> ORGANISM: ARTIFICIAL
<220> FEATURE:
<223> OTHER INFORMATION: Arg-4

<400> SEQUENCE: 46

Arg Arg Arg Arg
1
```

NEUROPROTECTIVE PEPTIDES

CROSS-REFERENCE TO RELATED APPLICATIONS

This application is a divisional of U.S. patent application Ser. No. 16/041,483, filed on Jul. 20, 2018; which is a divisional of U.S. patent application Ser. No. 14/392,392, national stage entry on Apr. 25, 2016; which is a U.S. National Phase of International Patent Application No. PCT/AU2014/050326, filed on 30 Oct. 2014; which claims priority to Application No. 2014902319, filed on Jun. 17, 2014, in Australia; and Application No. 2013904197, filed on Oct. 30, 2013, in Australia.

INCORPORATION BY REFERENCE OF MATERIALS SUBMITTED ELECTRONICALLY

This application contains, as a separate part of the disclosure, a Sequence Listing in computer readable form (Filename: 53102C_Seqlisting.txt; Size: 11,387 bytes; Created: Dec. 13, 2021), which is incorporated herein by reference in its entirety.

FIELD OF THE INVENTION

This invention relates to peptides having neuroprotective activity, the peptides being useful in treating stroke and other neural injuries or disorders. The invention relates further to a method of treating a neural injury or disorder using the peptides of the invention.

BACKGROUND OF THE INVENTION

Cell penetrating peptides (CPPs) are small peptides that are used to facilitate the delivery of normally non-permeable cargos such as other peptides, proteins, nucleic acids or drugs into cells.

The development of cell penetrating peptides (CPPs), also referred to as peptide transduction domains (PTDs), as facilitators of therapeutic drug delivery has progressed significantly since the initial discovery of a PTD within the human immunodeficiency virus-type 1 trans-activating transcriptional activator (Frankel and Pabo, 1988; Green and Loewenstein, 1988), commonly referred to as TAT. Since then, the active transporting portion of this sequence has been isolated [(TAT$_{48-58}$: referred to as the TAT (SEQ ID NO: 21) peptide] as well as the discovery and synthesis of over 100 novel CPPs (Milletti, 2012).

Potential therapeutics fused to CPPs have been assessed in neuronal culture systems and animal models that mimic neural injury mechanisms in a variety of disorders, including cerebral ischemia, epilepsy, Parkinson's disease and Alzheimer's diseases (Lai et al., 2005; Liu et al., 2006; Arthur et al., 2007; Colombo et al., 2007; Nagel et al., 2008; Meade et al., 2009). The use of CPPs for neurological disorders is especially attractive due to their ability to transport cargo across the blood brain barrier and then enter into neural cells within the brain parenchyma (Aarts et al., 2002; Zhang et al., 2013). Two examples of CPP-fused neuroprotective peptides that have entered clinical trials are the JNK inhibitor peptide (SEQ ID NO: 25) (JNKI-1 D-TAT or XG-102; ARAMIS, 2012) and the NMDA receptor/postsynaptic density-95 inhibitory peptide (SEQ ID NO: 18) (TAT-NR2B9c or NA-1; Dolgin, 2012). Both peptides are fused to TAT (SEQ ID NO: 21).

An important feature of any CPP is limited toxicity at clinically relevant doses, and there is a great need for CPPs of limited toxicity. Similarly, there is a great need when treating neural injuries for peptides that are neuroprotective. The structures and amino acid content of CPPs vary wildly and it has recently been shown that the TAT (SEQ ID NO: 21) peptide, the most widely used CPP used in neuroprotection experiments, appears to also possess intrinsic neuroprotective properties. Recent studies (Xu et al., 2008; Vaslin et al., 2009; Meade et al., 2010a,b; Craig et al., 2011) have reported that the TAT (SEQ ID NO: 21) peptide displays neuroprotective actions in vitro following excitotoxicity and oxygen-glucose deprivation, and in vivo following cerebral ischemia in P12 rats after intraventricular injection. While the exact mechanisms of TAT's (SEQ ID NO: 21) neuroprotective action are not fully understood, there is speculation that it interferes with NMDA receptor activation (Xu et al., 2008; Vaslin et al., 2009), although one study failed to detect a binding interaction (Li et al., 2008). Additionally, in an RNAi study using CPPs to deliver constructs, both the TAT (SEQ ID NO: 21) and penetratin (SEQ ID NO: 22) peptides alone were shown to down-regulate MAP kinase mRNA in the lung following intratracheal administration (Moschos et al., 2007).

Neuronal or neural injuries or disorders such as migraine, stroke, traumatic brain injury, spinal cord injury, epilepsy and neurodegenerative disorders including Huntington's Disease (HD), Parkinson's Disease (PD), Alzheimer's Disease (AD) and Amyotrophic Lateral Sclerosis (ALS) are major causes of morbidity and disability arising from long term brain or spinal cord injury. The brain injuries generally involve a range of cell death processes including apoptosis, autophagy, necroptosis and necrosis, and affect neurons astrocytes, oligodentrocytes, microglia and vascular endothelial cells (collectively referred to as the neurovascular unit; NVU). The damaging triggers involved in neural injury involve diverse pathways involving glutamate excitotoxicity calcium overload, oxidative stress, proteolytic enzymes and mitochondrial disturbances.

As used herein, the term "stroke" includes any ischemic disorder affecting the brain or spinal cord, e.g. thromboembolic occlusion in a brain or spinal cord artery, severe hypotension, perinatal hypoxia-ischaemia, a myocardial infarction, hypoxia, cerebral haemorrhage, vasospasm, a peripheral vascular disorder, a venous thrombosis, a pulmonary embolus, a transient ischemic attack, lung ischemia, unstable angina, a reversible ischemic neurological deficit, adjunct thrombolytic activity, excessive clotting conditions, cerebral reperfusion injury, sickle cell anemia, a stroke disorder or an iatrogenically induced ischemic period such as angioplasty, or cerebral ischemia.

Increased extracellular levels of the neurotransmitter glutamate can cause neuronal cell death via acute and delayed damaging processed caused by excitotoxicity. An accumulation of extracellular glutamate over-stimulates NMDA and AMPA receptors resulting in an influx of extracellular calcium and sodium ions and the release of bound calcium from intracellular stores. Over-activation of NMDA receptors can also trigger the production of damaging molecules (eg. nitric oxide, CLCA1; calcium-activated chloride channel regulator 1, calpain, SREBP1: sterol regulatory element binding protein-1) and signaling pathways (e.g.

DAPK; death-associated protein kinase, CamKII: calcium-calmodulin-dependent protein kinase II). In addition, glutamate-induced neuronal depolarization and excitotoxicity can trigger further intracellular calcium influx via voltage-gated calcium channels (VGCC, e.g. CaV2.2, CaV3.3), the sodium calcium exchanger (NCX), acid-sensing ion channels (ASIC), transient receptor potential cation channels 2 and 7 (TRPM2/7) and: metabotropic glutamate receptors (mGluR).

The increase in intracellular calcium initiates a range of cell damaging events involving phospholipases, proteases, phosphatases, kinases, NADPH oxidase and nitric oxide synthase, as well as the activation of pathways triggering cell death (i.e. apoptosis, autophagy, necroptosis and necrosis).

Examples of compounds used to treat the neurodegenerative effects of cerebral ischemia include U.S. Pat. No. 5,559,095, which describes a method of treating ischemia-related neuronal damage using omega-conotoxin peptides and related peptides which bind to and block voltage-gated calcium channels, and U.S. Pat. No. 4,684,624, which describes treatment using certain opioid peptides. Further examples include US 2009/0281036 that discloses the use of fusion peptides linked to other peptides for reducing damaging effects of injuries to mammalian cells by inhibiting the interaction of NMDA receptor and NMDAR interacting proteins. Similarly, US2012/0027781 discloses the use of linked targeting peptides and other peptides to provide neuroprotective functioning. U.S. Pat. No. 6,251,854 discloses compounds that provide protection against excitotoxic neuronal damage which are selected from short arginine-rich oligopeptides combined with compounds of formula 1:

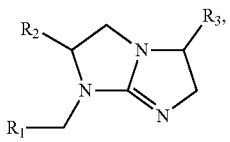

Many potential neuroprotective agents also exhibit toxicity at low to moderate doses. Many CPPs also exhibit toxicity at low to moderate doses. There is a need thus for neuroprotective peptides which are effective at low doses, which exhibit low cellular toxicity, and which provide protection against more than one type of neural injury.

This discussion of the background art is intended to facilitate an understanding of the present invention only. No acknowledgement or admission is intended that any of the material referred to is, or was, part of the common general knowledge as at the priority date of the application is intended.

SUMMARY OF THE INVENTION

According to one aspect of the invention, there is provided the use of an isolated, basic (i.e. cationic) amino acid-rich peptide as a neuroprotective agent. The isolated peptide may be a CPP.

As such, the invention extends to an isolated, cationic amino acid-rich peptide having neuroprotective activity. The invention extends to functional fragments of the peptide that exhibit neuroprotective activity.

The peptide may have a net charge of 8 or higher at pH 7, preferably 10 or higher at pH 7, most preferably 11 or higher at pH 7.

The peptide may be a non-naturally occurring peptide. As such, the peptide of the invention may be a man-made peptide.

The cationic (i.e. basic) amino acid residues forming part of the peptide may be arginine or lysine. Thus, the peptide may be arginine-rich. Alternatively, or additionally, the peptide may be lysine-rich, and/or tryptophan-rich.

The peptide may be between 10 amino acids and 100 amino acids in length, preferably between 10 amino acids and 32 amino acids.

The peptide may have the sequence:

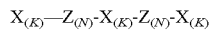

wherein X may be any naturally occurring or synthetic amino acid, including a cationic (i.e. basic) amino acid residue;

K is an integer between 1 and 5;

Z is a basic (i.e. cationic) amino acid residue; and

N is an integer between 1 and 30.

Substitution at "X" positions with amino acids which do not decrease the neuroprotective effects of the neuroprotective peptides are preferred. In one embodiment, Z may be arginine. In another embodiment, Z may be lysine. The peptide may include at least one contiguous arginine-rich segment. In other embodiments, the peptide may include a non-contiguous arginine-rich segment.

The basic (i.e. cationic) amino acid residues may be included at a ratio of at least 30% of the peptide or segment, preferably at least 40%, preferably at least 50%, more preferably at least 60%, in some cases as high as 100% of the peptide or segment. The peptide may have an arginine content of more than 20% of the amino acid content of the peptide, preferably more than 30%, more than 40%, more than 50%, more than 60%, more than 70% more than 80%, more than 90, more than 95%, more than 99%, or most preferably 100%. In certain embodiments of the invention, the peptide may have a combined arginine and lysine content of more than 40%, more than 50%, more than 60%, more than 70% more than 80%, more than 90, more than 95%, more than 99%, or most preferably 100%.

The peptide may include a plurality of single cationic amino acid residues, such as arginine residues, interspersed by other amino acid residues, in particular, it may be interspersed with basic (i.e. cationic) amino acid residues, such as lysine, and/or tryptophan. The peptide may include repeats of arginine residues in adjacent positions, such as RR, or RRR, or RRRR (SEQ ID NO: 46), or higher order repeats, and may be interspersed between other amino acids, or between stretches of amino acids.

As such, the peptide may be comprised completely of cationic amino acids. In one embodiment, the peptide is comprised completely of arginine residues.

According to an aspect of the invention, there is provided use of an isolated peptide of 10 to 32 amino acid residues in length for the treatment of neural injury, wherein the isolated peptide comprises at least 10 to 22 residues.

In a preferred embodiment of the invention, the peptide may be an isolated peptide of 10 to 32 amino acid residues in length for the treatment of neural injury, wherein the isolated peptide comprises at least 10 to 22 arginine residues.

The isolated peptide may have an arginine residue content of at least 30%, at least 40%, at least 50%, at least 60%, at least 70%, at least 80%, at least 90%, or at least 99%.

The isolated peptide may be a poly-arginine peptide comprising 10 to 22 arginine residues. In a preferred embodiment, the isolated peptide is R12 (SEQ ID NO: 9), R15 (SEQ ID NO: 12), or R18 (SEQ ID NO: 13), most preferably R18 (SEQ ID NO: 13).

Specifically, the isolated peptide may comprise any one or more of the peptides selected from the group consisting of SEQ ID NOs: 7, 8, 9, 10, 11, 12, 13, 16, 30, 31, 32, 33, 34, 35, 36, 37, 39, 40, 41, and functional fragments and analogues thereof having neuroprotective activity.

The isolated peptide may include at least one poly-arginine segment comprising at least 4 contiguous arginine residues, preferably at least two poly-arginine segments, more preferably three poly-arginine segments.

The isolated peptide may be penetratin (SEQ ID NO: 22).

The isolated peptide may comprise a mix of protamine derivatives (SEQ ID NOs: 32 to 37). The mix of protamine derivatives may comprise protamine sulphate (Ptm1-4 mixture; SEQ ID NOs: 32 to 35).

The isolated peptide may affect the endocytotic processes of the cell; affect the function of cell surface receptors to result in reduced cellular calcium influx; interact with and/or stabilises the outer mitochondrial membrane to preserve mitochondrial function; or inhibit, downregulate, or affect the calcium-dependent pro-protein convertase enzyme furin.

The isolated peptide may be a synthetic peptide or a man-made peptide. The isolated peptide may be included within, or fused to, other polypeptides. The isolated peptides may be fused to one another with at least one linker sequence The isolated peptide may exhibit neuroprotective activity at IC50 levels of less than 50 µM, preferably less than 20 µM, most preferably less than 10 µM.

The invention extends to the use of an isolated peptide comprising any one or more SEQ ID NOs: 7, 8, 9, 10, 11, 12, 13, 16, 30, 31, 32, 33, 34, 35, 36, 37, 39, 40, 41 and functional fragments or analogues thereof having neuroprotective activity, in the manufacture of a pharmaceutical composition or medicament for treating or preventing neural injury.

The pharmaceutical composition or medicament may be used for the treatment or prevention of a neural injury, the pharmaceutical composition or medicament including the isolated peptide of the invention or the polynucleotide sequence of the invention.

The pharmaceutical composition or medicament may be used in the treatment or prevention of ischemia, perinatal hypoxia-ischemia, Alzheimer's disease, Huntington's Disease, Multiple Sclerosis, Parkinson's disease, amyotrophic lateral sclerosis, stroke, peripheral neuropathy, neuropathic pain, spinal cord injury, traumatic brain injury or epilepsy.

The pharmaceutical composition or medicament may comprise a pharmaceutically acceptable carrier, adjuvant, or vehicle.

According to another aspect of the invention there is provided a method of treating a neural injury or promoting survival of neurons, the method including the steps of administering to a patient in need thereof a pharmaceutically acceptable and/or pharmaceutically effective amount of the peptide of the invention or the pharmaceutical composition or medicament of the invention.

According to a still further aspect of the invention there is provided a method for inhibiting neuronal cell death in a subject comprising administering to a subject in need of such treatment a pharmaceutically acceptable and/or pharmaceutically effective amount of the peptide of the invention or the pharmaceutical composition or medicament of the invention.

Administration may be from 0.001 mg/kg to 50 mg/kg.

The invention extends to kit comprising the pharmaceutical composition or medicament of the invention in one or more container(s) and an instruction manual or information brochure regarding instructions and/or information with respect to application of the pharmaceutical composition.

More specifically, the peptide may be any one or more of the peptides having the sequences set forth as SEQ ID NOs: 7, 8, 9, 10, 11, 12, 13, 16, 30, 31, 32, 33, 34, 35, 36, 37, 39, 40, 41, or may include sequences having at least 60%, preferably 70%, more preferably 80%, even more preferably 90%, yet more preferably 99% or higher sequence identity to said peptides, such peptides having neuroprotective activity.

The peptide may comprise any length of poly-arginine peptide between R8 (SEQ ID NO: 5) and R22 (SEQ ID NO: 41), or repeats thereof. In one embodiment, the peptide is selected from the group comprising R8 (SEQ ID NO: 5), R9 (SEQ ID NO: 6), R10 (SEQ ID NO: 7), R11 (SEQ ID NO: 8), R12 (SEQ ID NO: 9) R13 (SEQ ID NO: 10), R14 (SEQ ID NO: 11), R15 (SEQ ID NO: 12), R16 (SEQ ID NO: 39), R17 (SEQ ID NO: 40), and R18 (SEQ ID NO: 13). In one preferred embodiment, the peptide is R10 (SEQ ID NO: 7). In another preferred embodiment, the peptide is R12 (SEQ ID NO: 9). In yet another preferred embodiment, the peptide is R15 (SEQ ID NO: 12). In another preferred embodiment, the peptide is R18 (SEQ ID NO: 13).

The use of the peptide may include the use of a mixture of any two or more of the peptides of the invention, particularly SEQ ID NOs: 32 to 36 and 39, in the treatment or prevention of a neural injury.

In another embodiment, the use may include using the peptide of SEQ ID NO: 37 in the treatment or prevention of a neural injury, or the use of SEQ ID NO: 37 with any of the peptides of SEQ ID NOs: 32 to 36 and 39.

In another aspect of the invention, there is provided the isolated peptides of SEQ ID NOs: 32 to 37 and 39, including sequences having at least 60%, 70%, 80%, 90%, even 99% or higher sequence identity to said peptides, such peptides having neuroprotective activity.

The peptides may be a commercially available mixture of protamine peptides (Ptm1-4 mixture; SEQ ID NOs: 32 to 35) isolated from salmon sperm.

As such, the peptides may be in the form of a mixture comprising protamine sulphate (Ptm1-4 mixture; SEQ ID NOs: 32 to 35), as described in the European Medicines Agency "Assessment Report for Protamine containing medicinal products", Procedure no EMEA/H/A-5(3)/1341 published 15 Nov. 2012, the contents of which are incorporated herein by way of reference only.

Table 1 shows a summary of different forms of salmon sperm protamine. The protamine peptide sequences (salmon) are present in protamine sulphate for clinical use or from the SwissProt database. As used in this specification, the term "Protamine" refers to a commercially available injectable form or protamine sulphate, which comprises a mixture of the peptides of SEQ ID NOs: 32 to 35.

The peptides may be present in the following percentage proportions in the mixture of peptides:

| SEQ. ID. NO | Identifier | Percentage |
| --- | --- | --- |
| 32 | Ptm1 | 15-25 |
| 33 | Ptm2 | 27-37 |
| 34 | Ptm3 | 20-30 |
| 35 | Ptm4 | 15-25 |

In a preferred embodiment, the peptides are present in the following percentage proportions in the mixture of peptides:

| SEQ. ID. NO | Identifier | Percentage |
|---|---|---|
| 32 | Ptm1 | 18-22 |
| 33 | Ptm2 | 30-35 |
| 34 | Ptm3 | 21.5-28 |
| 35 | Ptm4 | 19-23 |

In a most preferred embodiment, the peptides are present in the following percentage proportions in the mixture of peptides:

| SEQ. ID. NO | Identifier | Percentage |
|---|---|---|
| 32 | Ptm1 | 20.1 |
| 33 | Ptm2 | 33.5 |
| 34 | Ptm3 | 25.1 |
| 35 | Ptm4 | 21.3 |

More particularly, the mixture of peptides may be a mixture of the peptides of SEQ ID NOs: 32, 33, 34, and 35, commercially available as protamine sulphate (Salmon), manufactured e.g. by Sanofi Aventis.

As such, the mixture of peptides may be admixed with sodium chloride, hydrochloric acid, sodium hydroxide and water.

The mixture of peptides may be in a delivery formulation that is injectable or administrable intravenously.

The peptides may be present in the delivery formulation in a concentration within a range of 0.1 mg/ml to 100 mg/ml, preferably 1 mg/ml to 20 mg/ml, most preferably 10 mg/ml.

In use, the delivery formulation, when in the form of an injectable or intravenous formulation, may be administered by slow intravenous injection over a period of between 1 and 30 minutes, preferably between 5 and 20 minutes, most preferably over a period of 10 minutes.

The peptide may have cell-penetrating activity. As such, the peptide may be a CPP.

The peptide may include repeats of arginine residues in adjacent positions, such as RR, or RRR, or RRRR (SEQ ID NO: 46), or higher order repeats, and may be interspersed between other amino acids, or between stretches of amino acids.

According to a further aspect of the invention, there is provided the use of the peptide of the invention in the manufacture of a pharmaceutical composition or medicament for the treatment of a neural injury. The invention extends to the use of mixtures of peptides of the invention in the manufacture of a medicament for the treatment of neural injury.

According to a still further aspect of the invention, there is provided the use of the peptide or pharmaceutical composition of the invention to affect the function of cell surface receptors associated with calcium influx, more specifically to interact with the NMDA, AMPA, VGCCs, NCX, TRMP2/7, ASIC and mGlu receptors, more specifically still to result in reduced cellular calcium influx. In another embodiment of the invention, there is provided the use of the peptide or pharmaceutical composition of the invention to interact with and/or stabilise the outer mitochondrial membrane and thereby help to preserve mitochondrial function. According to a still further aspect of the invention, there is provided the use of the peptide or pharmaceutical composition of the invention to inhibit, downregulate, or affect the calcium-dependent pro-protein convertase enzymes (e.g. furin).

According to another aspect of the invention, there is provided a pharmaceutical composition or medicament for the treatment of a neural injury, the pharmaceutical composition or medicament including the isolated peptide of the invention, or any one or more of the isolated peptides of the invention.

The pharmaceutical composition or medicament may comprise a pharmaceutically acceptable carrier, adjuvant, or vehicle According to a still further aspect of the invention, there is provided a method of treating a neural injury, the method including the steps of administering to a patient in need thereof a pharmaceutically acceptable and/or pharmaceutically effective amount of the peptide of the invention. The patient may be administered a physiologically acceptable amount of the peptide of the invention.

According to a still further aspect of the invention there is provided a method for inhibiting neuronal cell death in a subject comprising administering to a subject in need of such treatment a neuroprotective peptide in an amount effective to inhibit neuronal cell death in the subject, where the neuroprotective peptide is any one or more of the peptides of the invention.

The patient may be administered a physiologically acceptable amount of a mixture of any two or more of the peptides of the invention.

More particularly, the patient may be administered a mixture of any two or more peptides selected from the group comprising SEQ ID NOs: 32, 33, 34, 35, 36, or 37. In one particular aspect of the invention, the patient may be administered a mixture comprising SEQ ID NOs: 32, 33, 34 and 35. In other combinations, the patient may be administered any combination of peptides selected from the group consisting of SEQ ID NOs: 32, 33, 34 and 35, together with the peptide of SEQ ID NO: 36. In a particular embodiment, the patient may be administered SEQ ID NO: 35.

The peptide of the invention may provide neuroprotective activity against antagonists of neurotransmitter receptors. The neurotransmitter receptors may be receptors that are bound by, interact with, or are affected by NMDA, glutamate, kainic acid, or ischemic processes. The peptide of the invention may be included within other polypeptides or may be fused to other polypeptides. The peptide of the invention may be linked or fused at either the N- or C-termini of such other polypeptides. The peptide of the invention may be linked or fused to such other polypeptides so as to display the peptides of the invention in a conformation suitable for treating a neural injury.

Alternatively, or additionally, one or more of the peptides of the invention may be fused to one another with a linker sequence. The linker sequence may comprise any sequence of amino acids, including, but not limited to basic/cationic amino acid-rich linker sequences. Alternatively, or additionally, the linker sequences may be cleavable linkers. In one embodiment, the linker may be one or more MMP-type linkers, calpain, caspase or tPA linkers. MMP-type linkers are defined as the peptide sequence recognized and cleaved by matrix metalloproteinases (MMPs). Similarly a calpain, caspase or tPA linker is a peptide sequence recognized and cleaved by these protease enzymes (i.e. calpain, caspase or tPA, respectively). The peptides of the invention may also be fused to other peptides that are to be transported to the site of a neural injury or are to be transported intracellularly into or within neural cells.

The peptides of the invention may also be linked to ancillary peptides that can bind to or interact with enzymes detrimental to neural function, so that the ancillary peptides can function as competitive inhibitors of the enzymes following transportation across the cell membrane. The ancillary peptides may be selected from tPA, calpain, and MMP, and may be linked to the peptide of the invention using a cleavable linker such as a caspase sequence, so that the tPA, calpain or MMP may be liberated from the peptide of the invention and may then function as a competitive inhibitor intracellularly for enzymes detrimental to neural function.

As such, the invention extends to a peptide of the invention linked to a caspase cleavage site, itself in turn linked to calpain, tPA or MMP.

The peptides of the invention may exhibit neuroprotective activity at IC50 levels of less than 10 µM, preferably less than 5 µM, preferably less than 1 µM, in some cases as low as, or lower than, 0.2 µM, even as low as 0.1 µM.

As mentioned before, the peptide may include repeats of the peptide sequences of the invention, or functional fragments thereof, i.e. fragments that exhibit neuroprotective activity.

Accordingly, one aspect of the invention provides an isolated polypeptide having included therein a peptide segment exhibiting neuroprotective effects, the peptide segment being between 8 and 100 amino acid residues in length, wherein the neuroprotective peptide is selected from peptide segments having a basic/cationic amino acid content of more than 20% of the length of the peptide segment, preferably more than 30%, more than 40%, more than 50%, more than 60%, more than 70% more than 80%, more than 90, more than 95%, more than 99%, or most preferably 100%.

According to another aspect of the invention, there is provided an isolated polynucleotide sequence that encodes a peptide of the invention, sequences complementary to the isolated polynucleotide sequence, and sequences having at least 60%, 70%, 80%, 90%, 95%, 99%, or 100% homology with the isolated polynucleotide sequences. The polynucleotide sequence may be one or more isolated sequences and may be sequences that hybridize under stringent conditions with the polynucleotide sequences of the invention. The polynucleotide sequences may be non-naturally occurring polynucleotide sequences or DNA. As such, they may include man-made, artificial constructs, such as cDNA. Also included in the invention are vectors, such as expression vectors, which include the isolated foregoing isolated nucleic acids, as well as cells transformed with such vectors or DNA sequences. The polynucleotide sequence may encode protamine. The polynucleotide sequences may be the sequence of SEQ ID NO 38.

In another aspect of the invention, there is provided the isolated peptides selected from the group consisting of SEQ ID NOs: 7, 8, 9, 10, 11, 12, 13, 16, 30, 31, 32, 33, 34, 35, 36, and 37, including sequences having at least 60%, preferably 70%, more preferably 80%, even more preferably 90%, yet more preferably 99% or higher sequence identity to said peptides, such peptides having neuroprotective activity.

The use of the isolated nucleic acids, vectors, or cells in the preparation of a pharmaceutical formulation or medicament also is provided.

The present invention furthermore provides kits comprising the abovementioned pharmaceutical composition (in one or more container(s)) in at least one of the above formulations and an instruction manual or information brochure regarding instructions and/or information with respect to application of the pharmaceutical composition.

In one embodiment, a pharmaceutical composition comprising the peptide of the invention as defined above is for use in the treatment of ischemia, Alzheimer's disease, Parkinson's disease, amyotrophic lateral sclerosis, stroke, peripheral neuropathy, spinal cord injury or epilepsy.

In another embodiment, the present invention provides a method for promoting survival of neurons comprising the step of contacting neurons with the peptides of the invention, or combinations thereof. Preferably, the method is performed in vitro. The invention, in another aspect thereof, provides a method and composition for protecting blood brain barrier endothelial cells from OGD or ischemia.

These findings demonstrate that the peptides of the invention have the ability to, and can be used in methods to, inhibit or ameliorate neurodamaging events/pathways associated with excitotoxic and ischemic injuries. Also, as shown by the effects of protamine (Ptm1-4 mixture; SEQ ID NOs: 32 to 35) and protamine derivatives (SEQ ID NO: 37) in pre-insult exposure trials contained herein, a new key finding was that protamine (Ptm1-4 mixture; SEQ ID NOs: 32 to 35) treatment of neurons 1 to 4 hours before glutamate or OGD exposure can induce a neuroprotective response by reducing cell death. This is significant because there are a number of cerebrovascular (e.g. carotid endarterectomy) and cardiovascular (e.g. coronary artery bypass graft) surgical procedures where there is a risk patients can suffer cerebral ischemia or a stroke resulting in brain injury.

Therefore, the method of the invention extends to the administering of the at least one peptide, medicament, or pharmaceutical composition of the invention in a window of 0.25 hours to 4 hours, preferably 0.5 to 3 hours, most preferably 1 to 2 hours before such a procedure to protect the brain against any such cerebral ischemic event.

The invention extends thus to the use of the at least one peptide of the invention in treating or preventing neural injury, cerebrovascular insults or injury, cardiovascular insults or injury, or surgical procedures where patients may be at risk of suffering cerebral ischemia or a stroke.

Minor modifications of the primary amino acid sequence of the sequences of the invention disclosed herein may result in proteins that have substantially equivalent or enhanced activities. These modifications may be deliberate, as through site-directed mutagenesis, or may be accidental, such as through mutation of hosts that are protamine- or LMWP-producing organisms. All of these modifications are included within the scope of the invention as long as the neuroprotective activity is retained.

BRIEF DESCRIPTION OF THE DRAWINGS

Further features of the present invention are more fully described in the following description of several non-limiting embodiments included solely for the purposes of exemplifying the present invention. The following description is not a restriction on the broad summary, disclosure or description of the invention as set out above and is made with reference to the accompanying drawings in which the term "Protamine" or "Ptm" refers to commercially available protamine sulphate (Ptm1-4 mixture; SEQ ID NOs: 32 to 35) (manufactured commercially by several manufacturers, including Sanofi Aventis, typically as specified in Hoffman, 1990), while "Ptm1" to "Ptm" 5 refer to SEQ ID NOs 32, 33, 34, 35, and 36, respectively.

FIG. 1a shows the results of the glutamic acid excitotoxicity model; concentration of peptide in µM. A: Neuronal viability 24 hours following glutamic acid exposure and treatment with CPPs, positive control peptides (JNKI-1 D-TAT; SEQ ID NO: 25/PYC36L-TAT; SEQ ID NO: 24) and glutamate receptor blockers (Blkrs; 5 µM: MK801/5 µM: CNQX). MTS data were expressed as percentage neuronal viability with no insult control taken as 100% viability (mean±SEM; n=4-6; *P<0.05).

FIG. 1b shows further results of the glutamic acid excitotoxicity model; concentration of peptide in μM. Neuronal viability 24 hours following glutamic acid exposure and treatment with TAT-L (SEQ ID NO: 21) and TAT-D (SEQ ID NO: 20) peptides. MTS data were expressed as percentage neuronal viability with no insult control taken as 100% viability (mean±SEM; n=4-6; *P<0.05).

FIG. 1c shows further results from the glutamic acid excitotoxicity model. Specifically, the efficacy of peptides when washed out prior to glutamic acid insult; concentration of peptide in μM. Neuronal viability 24 hours following glutamic acid exposure when CPPs were washed-out prior to insult. MTS data were expressed as percentage neuronal viability with no insult control taken as 100% viability (mean±SEM; n=4-6; *P<0.05).

FIG. 1d shows further results from the glutamic acid excitotoxicity model. Efficacy of peptides when added after the glutamic acid insult. Neuronal viability 24 hours following glutamic acid exposure when Arg-9 (R9) (SEQ ID NO: 6) and Arg-12 (R12) (SEQ ID NO: 9) peptides and control peptides JNKI-1 D-TAT (SEQ ID NO: 25) and NR2B9c (SEQ ID NO: 18) were added 0 or 15 minutes post-insult; in this experiment glutamic acid exposure resulted in less cell death in controls than in other experiments (60% vs 95%). MTS data were expressed as percentage neuronal viability with no insult control taken as 100% viability (mean±SEM; n=4-6; *P<0.05).

FIG. 1e shows further results from the glutamic acid excitotoxicity model; concentration of peptide in μM. A: Neuronal viability 24 hours following glutamic acid exposure and treatment with R9 (SEQ ID NO: 6), R12 (SEQ ID NO: 9), R15 (SEQ ID NO: 12), R18 (SEQ ID NO: 13) and R9/tPA/R9 (SEQ ID NO: 16). MTS data were expressed as percentage neuronal viability with no insult control taken as 100% viability (mean±SEM; n=4; *P<0.05).

FIG. 1f shows further results from the glutamic acid excitotoxicity model; concentration of peptide in μM. Neuronal viability 24 hours following glutamic acid exposure and treatment with R9 (SEQ ID NO: 6), E9/R9 (SEQ ID NO: 15), DAHK (SEQ ID NO: 17) and PTD-4 (SEQ ID NO: 14) MTS data were expressed as percentage neuronal viability with no insult control taken as 100% viability (mean±SEM; n=4; *P<0.05).

FIG. 1g shows further results from the glutamic acid excitotoxicity model; concentration of peptide μM. Neuronal viability 24 hours following glutamic acid exposure and treatment with R9 (SEQ ID NO: 6) and NR2B9c (SEQ ID NO: 18) and control peptide PCY36 (PYC36L-TAT; SEQ ID NO: 24). MTS data were expressed as percentage neuronal viability with no insult control taken as 100% viability (mean±SEM; n=4; *P<0.05).

FIG. 1h shows further results from the glutamic acid excitotoxicity model: milder insult; concentration of peptide μM. Neuronal viability 24 hours following glutamic acid exposure and treatment with R9 (SEQ ID NO: 6), R12 (SEQ ID NO: 9) and NR2B9c (SEQ ID NO: 18) and control peptide JNK (JNKI-1-TAT; SEQ ID NO: 25). MTS data were expressed as percentage neuronal viability with no insult control taken as 100% viability (mean±SEM; n=4; *P<0.05).

FIG. 1i shows further results from the glutamic acid excitotoxicity model: milder insult; concentration of peptide μM. Neuronal viability 24 hours following glutamic acid exposure and treatment with R1 (SEQ ID NO: 1), R3 (SEQ ID NO: 2), R6 (SEQ ID NO: 3), R9 (SEQ ID NO: 6), R12 (SEQ ID NO: 9) and NR2B9c (SEQ ID NO: 18) control peptide. MTS data were expressed as percentage neuronal viability with no insult control taken as 100% viability (mean±SEM; n=4; *P<0.05).

FIG. 1j shows further results from the glutamic acid excitotoxicity model; concentration of peptide=5 μM. Neuronal viability 24 hours following glutamic acid exposure and treatment with R1 (SEQ ID NO: 1), R3 (SEQ ID NO: 2), R9 (SEQ ID NO: 6) old (Mimotopes), R9 (SEQ ID NO: 6) new (China peptides), R12 (SEQ ID NO: 9). MTS data were expressed as percentage neuronal viability with no insult control taken as 100% viability (mean±SEM; n=4; *P<0.05).

FIG. 2 shows the results of a kainic acid excitotoxicity model; concentration of peptide in μM. Neuronal viability 24 hours following kainic acid exposure and treatment with CPPs, positive control peptides (JNKI-1 D-TAT; SEQ ID NO: 25/PYC36L-TAT; SEQ ID NO: 24) and glutamate receptor blockers (Blkrs; 5 μM: MK801/5 μM: CNQX). MTS data were expressed as percentage neuronal viability with no insult control taken as 100% viability (mean±SEM; n=4; *P<0.05).

FIG. 3a shows the results of an in vitro ischemia model. Peptides present during in vitro ischemia and at 50% dose after ischemia: concentration of peptide in μM. Neuronal viability 24 hours following in vitro ischemia and treatment with CPPs, positive control peptide (PYC36L-TAT; SEQ ID NO: 24) and glutamate receptor blockers (Blkrs; 5 μM: MK801/5 μM: CNQX). MTS data were expressed as percentage neuronal viability with no insult control taken as 100% viability (mean±SEM; n=4; *P<0.05).

FIGS. 46 and 47 are reference tables of the sequences described and used in this specification.

DESCRIPTION OF EMBODIMENTS

Figure 3B:
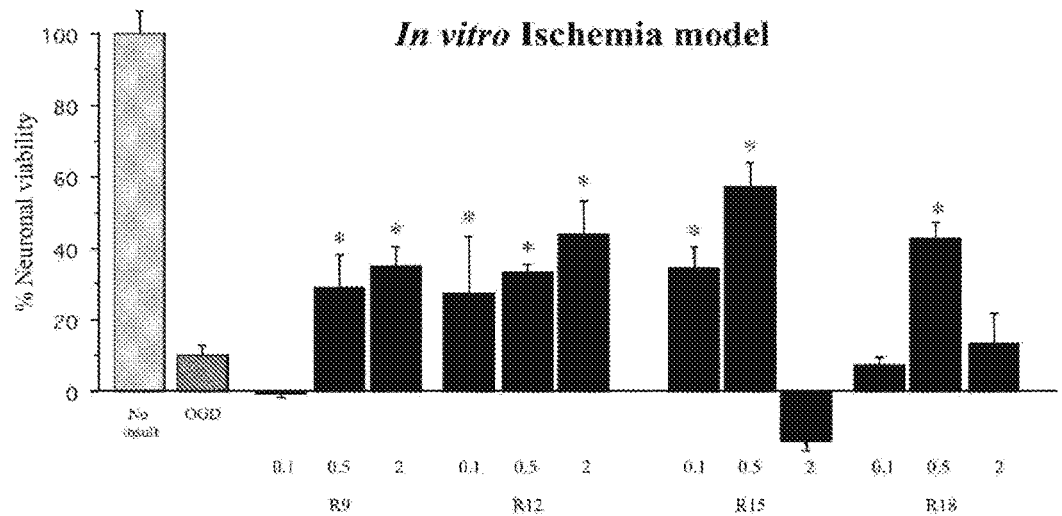
FIG. 3b shows further results of an in vitro ischemia model. Peptides present after in vitro ischemia: concentration of peptide in μM. Neuronal viability 24 hours following in vitro ischemia and treatment with R9 (SEQ ID NO: 6), R12 (SEQ ID NO: 9), R15 (SEQ ID NO: 12) and R18 (SEQ ID NO: 13). MTS data were expressed as percentage neuronal viability with no insult control taken as 100% viability (mean±SEM; n=4; *P<0.05).

Throughout this specification, unless the context requires otherwise, the word "comprise" or variations such as "comprises" or "comprising" or "includes" or "including", will be understood to imply the inclusion of a stated integer or group of integers but not the exclusion of any other integer or group of integers.

The invention relates to isolated peptides and compositions comprising isolated peptides, and uses thereof. The isolated peptides are characterized in that they can reduce the neurodegenerative effects of a neural injury or cerebrovascular ischemic event (e.g., and especially, stroke) when administered before or after the neural injury or ischemic event. Thus, administration of the compositions of the invention reduces the loss of neuronal cells that follows a neural injury or cerebrovascular ischemic event. The Applicant has now found, surprisingly, that certain polypeptides in the form of CPPs and polypeptides having contiguous stretches of basic/cationic amino acids (particularly arginine residues, but also including lysine and tryptophan residues), exhibit neuroactive or neuroprotective activity and can serve as neuroprotective agents (i.e. for treatment of neural injury) by themselves, i.e. without having to be fused to other neuroprotective agents or peptides. As such, the invention pertains to polypeptides of between 10 and 32 amino acids in length wherein between 10 and 22 of the amino acids are cationic amino acid residues (typically arginine residues), with such peptides typically having an arginine content of 30% or higher, such peptides exhibiting neuroprotective activity in established neural injury models. This includes poly-arginine peptides, as well as protamine sulphate (as mixture of protamine peptides obtained from salmon sperm), and various versions, analogues, variants, or fragments of these peptides, including protamine (SEQ ID NOs: 32 to 36) and low molecular weight protamine (LMWP; SEQ ID NO: 37), and mixtures thereof.

The term "amino acid" or "residue" as used herein includes any one of the twenty naturally-occurring amino acids, the D-form of any one of the naturally-occurring amino acids, non-naturally occurring amino acids, and derivatives, analogues and mimetics thereof. Any amino acid, including naturally occurring amino acids, may be purchased commercially or synthesized by methods known in the art. Examples of non-naturally-occurring amino acids include norleucine ("Nle"), norvaline ("Nva"), β-Alanine, L- or D-naphthalanine, ornithine ("Orn"), homoarginine (homoArg) and others well known in the peptide art, including those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference.

Common amino acids may be referred to by their full name, standard single-letter notation (IUPAC), or standard three-letter notation for example: A, Ala, alanine; C, Cys, cysteine; D, Asp, aspartic; E, Glu, glutamic acid; F, Phe, phenylalanine; G, Gly, glycine; H, His, histidine; I, Ile isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; Y, Tyr, tyrosine. Any and all of the amino acids in the compositions herein can be naturally occurring, synthetic, and derivatives or mimetics thereof.

As used herein, "isolated" means a peptide described herein that is not in a natural state (e.g. it is disassociated from a larger protein molecule or cellular debris in which it naturally occurs or is normally associated with), or is a non-naturally occurring fragment of a naturally occurring protein (e.g. the peptide comprises less than 25%, preferably less than 10% and most preferably less than 5% of the naturally occurring protein). Isolated also may mean that the amino acid sequence of the peptide does not occur in nature, for example, because the sequence is modified from a naturally occurring sequence (e.g. by alteration of certain amino acids, including basic (i.e. cationic) amino acids such as arginine, tryptophan, or lysine), or because the sequence does not contain flanking amino acids which are present in nature. The term "isolated" may mean that the peptide or amino acid sequence is a man-made sequence or polypeptide and may be non-naturally occurring.

Likewise, "isolated" as used in connection with nucleic acids which encode peptides embraces all of the foregoing, e.g. the isolated nucleic acids are disassociated from adjacent nucleotides with which they are associated in nature, and can be produced recombinantly, synthetically, by purification from biological extracts, and the like. Isolated nucleic acids can contain a portion that encodes one of the foregoing peptides and another portion that codes for another peptide or protein. The isolated nucleic acids also can be labeled. The nucleic acids include codons that are preferred for animal, bacterial, plant, or fungal usage. In certain embodiments, the isolated nucleic acid is a vector, such as an expression vector, which includes a nucleic acid that encodes one of the foregoing isolated peptides. A general method for the construction of any desired DNA sequence is provided, e.g., in Brown J. et al., (1979), Methods in Enzymology, 68:109; Sambrook J, Maniatis T (1989), supra.

Non-peptide analogues of peptides, e.g., those that provide a stabilized structure or lessened biodegradation, are also contemplated. Peptide mimetic analogues can be prepared based on a selected peptide by replacement of one or more residues by non-peptide moieties. Preferably, the non-peptide moieties permit the peptide to retain its natural conformation, or stabilize a preferred, e.g., bioactive, conformation. One example of methods for preparation of non-peptide mimetic analogues from peptides is described in Nachman et al., *Regul. Pept.* 57:359-370 (1995). The term "peptide" as used herein embraces all of the foregoing.

As mentioned above, the peptide of the present invention may be composed either of naturally occurring amino acids, i.e. L-amino acids, or of D-amino acids, i.e. of an amino acid sequence comprising D-amino acids in retro-inverso order as compared to the native sequence. The term "retro-inverso" refers to an isomer of a linear peptide in which the direction of the sequence is reversed and the chirality of each amino acid residue is inverted. Thus, any sequence herein, being present in L-form is also inherently disclosed herein as a D-enantiomeric (retro-inverso) peptide sequence. D-enantiomeric (retro-inverso) peptide sequences according to the invention can be constructed, e.g. by synthesizing a reverse of the amino acid sequence for the corresponding native L-amino acid sequence. In D-retro-inverso enantiomeric peptides, e.g. a component of the isolated peptide, the positions of carbonyl and amino groups in each single amide bond are exchanged, while the position of the side-chain groups at each alpha carbon is preserved.

Preparation of a component of the isolated peptides of the invention as defined above having D-enantiomeric amino acids can be achieved by chemically synthesizing a reverse amino acid sequence of the corresponding naturally occurring L-form amino acid sequence or by any other suitable method known to a skilled person. Alternatively, the D-retro-inverso-enantiomeric form of an peptide or a component thereof may be prepared using chemical synthesis as disclosed above utilizing an L-form of an peptide or a component thereof as a matrix for chemical synthesis of the D-retro-inverso-enantiomeric form.

A cationic amino acid-rich polypeptide (which can also be referred to as a cationic amino acid polymer or copolymer) can include a polypeptide or oligomer of 10 to 32 amino acids in length. As such, by "cationic-rich" is meant any peptide, oligopeptide, or polypeptide that comprises or includes, typically, more than 30% cationic residues, more than 50%, or even more than 60%. In certain embodiments this may entail peptides comprising 90%, or even 100% cationic residues such as, preferably, arginine residues. Accordingly, by an arginine-rich polypeptide (which can also be referred to as an arginine amino acid polymer or copolymer) can include a polypeptide or oligomer of 10 to 32 amino acids in length. As such, by "arginine-rich" is meant any peptide, oligopeptide, or polypeptide that comprises or includes 10 or more arginine residues, or more than 30% arginine residues, more than 50%, or even more than 60%. As such, certain embodiments comprise peptides in which 100% of the amino acids are arginine residues, with suitable efficacy and low toxicity when used in the range of R10 (SEQ ID NO: 7) to R18 (SEQ ID NO: 13) and at pharmaceutically efficient dosages, while in other cases it refers to other peptides (such as CPPs and including protamine; SEQ ID NOs: 32 to 36 and LMWP; SEQ ID NO: 37) which have intermittent stretches of arginine residues. Usually, the stretches of arginine residues comprise consecutive/contiguous 4 to 5 arginine residues, being interspersed by other amino acid residues. In preferred embodiments, the interspersed amino acids are lysine (K) residues, since these also have a generally cationic charge.

In certain embodiments, an arginine polymer or copolymer includes at least 11 contiguous arginine residues, more preferably at least 12 contiguous arginine residues, more preferably at least 13 contiguous arginine residues, more preferably at least 14 contiguous arginine residues, more preferably at least 15 contiguous arginine residues, more preferably at least 16 contiguous arginine residues, more preferably at least 17 contiguous arginine residues and more preferably at least 18 contiguous arginine residues. However, in certain embodiments, there may be contiguous sequences of 4 to 5 arginine residues interspersed by other, non-arginine residues, such as those exemplified by protamine (SEQ ID NOs: 32 to 36), LMWP (SEQ ID NO: 37), and functional variants thereof having neuroprotective activity or for use in treating neural injury, as shown herein. In a preferred embodiment, use is made of R15 (SEQ ID NO: 12). In a preferred embodiment, use is made of R18 (SEQ ID NO: 13).

The contiguous arginine residues can be at the C-terminus of the polypeptide, N-terminus of the polypeptide, in the centre of the polypeptide (e.g., surrounded by non-arginine amino acid residues), or in any position within a polypeptide. Non-arginine residues are preferably amino acids, amino acid derivatives, or amino acid mimetics that do not significantly reduce the rate of membrane transport of the polymer into cells, including, for example, glycine, alanine, cysteine, valine, leucine, isoleucine, methionine, serine, threonine, α-amino-beta-guanidinopropionic acid, α-amino-γ-guanidinobutyric acid, and α-amino-ε-guanidinocaproic acid.

Various changes may be made including the addition of various side groups that do not affect the manner in which the peptide functions, or which favourably affect the manner in which the peptide functions. Such changes may involve adding or subtracting charge groups, substituting amino acids, adding lipophilic moieties that do not effect binding but that affect the overall charge characteristics of the molecule facilitating delivery across the blood-brain barrier, etc. For each such change, no more than routine experimentation is required to test whether the molecule functions according to the invention. One simply makes the desired change or selects the desired peptide and applies it in a fashion as described in detail in the examples. For example, if the peptide (modified or unmodified) is active in a test of protection against kainic acid, or if such a peptide competes with the parent neurotransmitter in a test of neurotransmitter function, then the peptide is a functional neurotransmitter peptide.

The invention also embraces functional variants of the isolated peptide. As used herein, a "functional variant" or "variant" of an isolated peptide is a peptide which contains one or more modifications to the primary amino acid sequence of the isolated peptide and retains the properties disclosed herein. Modifications which create a functional variant of the isolated peptide can be made, for example, 1) to enhance a property of an isolated peptide, such as peptide stability in an expression system; 2) to provide a novel activity or property to an isolated peptide, such as addition of an antigenic epitope or addition of a detectable moiety; or 3) to provide a different amino acid sequence that produces the same or similar peptide properties. Modifications to an isolated peptide can be made to a nucleic acid that encodes the peptide, and can include deletions, point mutations, truncations, amino acid substitutions and additions of amino acids. Alternatively, modifications can be made directly to the peptide, such as by cleavage, addition of a linker molecule, preferably a cleavable linker such as MMP, calpain, tPA, addition of a detectable moiety such as biotin, addition of a fatty acid, substitution of one amino acid for another and the like. Modifications also embrace fusion proteins comprising all or part of the isolated peptide amino acid sequence. In one embodiment, the linker is selected from one or more MMP-type linkers, calpain, caspase, or tPA linkers. MMP-type linkers are defined as the peptide sequence recognized and cleaved by matrix metalloproteinases (MMPs). Similarly a calpain, caspase or tPA linker is a peptide sequence recognized and cleaved by these protease enzymes. In certain embodiments, the peptides of the invention are also fused to other peptides that are to be transported to the site of a neural injury or are to be transported intracellularly in neural cells. As such, the peptides of the invention may also be linked to ancillary peptides that can bind to or interact with enzymes detrimental to neural function, so that the ancillary peptides can function as competitive inhibitors of the enzymes following transportation across the cell membrane by the peptide of the invention. The ancillary peptides are tPA, calpain, and MMP, and are linked to the peptide of the invention using a cleavable linker such as a caspase sequence, so that the tPA, calpain or MMP is liberated from the peptide of the invention to then function as a competitive inhibitor intracellularly for enzymes detrimental to neural function.

As such, the invention extends to a peptide of the invention, such as R10-R18 (SEQ ID NOs; 7, 8, 9, 10, 11, 12, 13, 39, 40, 41 respectively) or Ptm1-5 (SEQ ID NOs: 32 to 36) or LMWP (SEQ ID NO: 37), or variants thereof, linked to a caspase cleavage site, itself in turn linked to calpain, tPA or MMP.

The term "sequence identity" as defined herein means that the sequences are compared as follows. To determine the percent identity of two amino acid sequences, the sequences can be aligned for optimal comparison purposes (e.g., gaps can be introduced in the sequence of a first amino acid sequence). The amino acids at corresponding amino acid positions can then be compared. When a position in the first sequence is occupied by the same amino acid as the corresponding position in the second sequence, then the molecules are identical at that position. The percent identity between the two sequences is a function of the number of identical positions shared by the sequences. For example, where a particular peptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Such a determination of percent identity of two sequences can be accomplished using a mathematical algorithm. A preferred, non-limiting example of a mathematical algorithm utilized for the comparison of two sequences is the algorithm of Karlin et al., (1993), PNAS USA, 90:5873-5877. Such an algorithm is incorporated into the NBLAST program, which can be used to identify sequences having the desired identity to the amino acid sequence of the invention. To obtain gapped alignments for comparison purposes, Gapped BLAST can be utilized as described in Altschul et al., (1997), Nucleic Acids Res, 25:3389-3402. When utilizing BLAST and Gapped BLAST programs, the default parameters of the respective programs (e.g., NBLAST) can be used. The sequences further may be aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence. The described methods of determination of the percent identity of two amino acid sequences can be applied correspondingly to nucleic acid sequences.

The peptide of the invention may be linked directly or via a linker. A "linker" in the present context is usually a peptide, oligopeptide or polypeptide and may be used to link multiples of the peptides to one another. The peptides of the invention selected to be linked to one another can be identical sequences, or are selected from any of the peptides of the invention. A linker can have a length of 1-10 amino acids, more preferably a length of 1 to 5 amino acids and most preferably a length of 1 to 3 amino acids. In certain embodiments, the linker is not required to have any secondary structure forming properties, i.e. does not require a α-helix or β-sheet structure forming tendency, e.g. if the linker is composed of at least 35% of glycine residues. As mentioned hereinbefore, a linker can be a cleavable peptide such as an MMP peptide which can be cleaved intracellularly by normal cellular processes, effective raising the intracellular dose of the previously linked peptides, while keeping the extracellular dose low enough to not be considered toxic. The use of a(n) intracellularly/endogenously cleavable peptide, oligopeptide, or polypeptide sequence as a linker permits the peptides to separate from one another after delivery into the target cell. Cleavable oligo- or polypeptide sequences in this context also include protease cleavable oligo- or polypeptide sequences, wherein the protease cleavage site is typically selected dependent on the protease endogenously expressed by the treated cell. The linker as defined above, if present as an oligo- or polypeptide sequence, can be composed either of D-amino acids or of naturally occurring amino acids, i.e. L-amino acids. As an alternative to the above, coupling or fusion of the peptides can be accomplished via a coupling or conjugating agent, e.g. a cross-linking reagent. There are several intermolecular cross-linking reagents which can be utilized, see for example, Means and Feeney, Chemical Modification of Proteins, Holden-Day, 1974, pp. 39-43. Among these reagents are, for example, N-succinimidyl 3-(2-pyridyldithio)propionate (SPDP) or N,N'-(1,3-phenylene)bismaleimide; N,N'-ethylene-bis-(iodoacetamide) or other such reagent having 6 to 11 carbon methylene bridges; and 1,5-difluoro-2,4-dinitrobenzene. Other cross-linking reagents useful for this purpose include: p,p'-difluoro-m,m'-dinitrodiphenylsulfone; dimethyl adipimidate; phenol-i1,4-disulfonylchloride; hexamethylenediisocyanate or diisothiocyanate, or azophenyl-p-diisocyanate; glutaraldehyde and disdiazobenzidine. Cross-linking reagents may be homobifunctional, i.e., having two functional groups that undergo the same reaction. A preferred homobifunctional cross-linking reagent is bismaleimidohexane (BMH). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of proteins (or polypeptides) that contain cysteine residues. Cross-linking reagents may also be heterobifunctional. Heterobifunctional cross-linking reagents have two different functional groups, for example an amine-reactive group and a thiol-reactive group, that will cross-link two proteins having free amines and thiols, respectively. Examples of heterobifunctional cross-linking reagents are succinimidyl 4-(N-maleimidomethyl) cyclohexane-1-carboxylate (SMCC), m-maleimidobenzoyl-N-hydroxysuccinimide ester (MBS), and succinimide 4-(p-maleimidophenyl)butyrate (SMPB), an extended chain analogue of MBS. The succinimidyl group of these cross-linking reagents with a primary amine, and the thiol-reactive maleimide forms a covalent bond with the thiol of a cysteine residue. Because cross-linking reagents often have low solubility in water, a hydrophilic moiety, such as a sulfonate group, may be added to the cross-linking reagent to improve its water solubility. Sulfo-MBS and sulfo-SMCC are examples of cross-linking reagents modified for water solubility. Many cross-linking reagents yield a conjugate that is essentially non-cleavable under cellular conditions. Therefore, some cross-linking reagents contain a covalent bond, such as a disulfide, that is cleavable under cellular conditions. For example, Traut's reagent, dithiobis(succinimidylpropionate) (DSP), and N-succinimidyl 3-(2-pyridyldithio) propionate (SPDP) are well-known cleavable cross-linkers. The use of a cleavable cross-linking reagent permits the peptides to be separated after delivery into the target cell, if desired, provided the cell is capable of cleaving a particular sequence of the crosslinker reagent. For this purpose, direct disulfide linkage may also be useful. Chemical cross-linking may also include the use of spacer arms. Spacer arms provide intramolecular flexibility or adjust intramolecular distances between conjugated moieties and thereby may help preserve biological activity. A spacer arm may be in the form of a protein (or polypeptide) moiety that includes spacer amino acids, e.g. proline. Alternatively, a spacer arm may be part of the cross-linking reagent, such as in "long-chain SPDP" (Pierce Chem. Co., Rockford, Ill., cat. No. 21651H). Numerous cross-linking reagents, including the ones discussed above, are commercially available. Detailed instructions for their use are readily available from the commercial suppliers. A general reference on protein cross-linking and conjugate preparation is: Wong, Chemistry of Protein Conjugation and Cross-Linking, CRC Press (1991).

The peptides of the invention may also contain a "derivative", "variant", or "functional fragment", i.e. a sequence of a peptide that is derived from the naturally occurring (L-amino-acid) sequence of a peptide of the invention as defined above by way of substitution(s) of one or more amino acids at one or more of sites of the amino acid sequence, by way of deletion(s) of one or more amino acids at any site of the naturally occurring sequence, and/or by way of insertion(s) of one or more amino acids at one or more sites of the naturally occurring peptide sequence. "Derivatives" shall retain their biological activity if used as peptides of the invention, e.g. a derivative of any of the peptides of the invention shall retain its neuroprotective activity. Derivatives in the context of the present invention may also occur in the form of their L- or D-amino-acid sequences as defined above, or both.

If substitution(s) of amino acid(s) are carried out for the preparation of a derivative of the peptides of the invention, conservative (amino acid) substitutions are preferred. Conservative (amino acid) substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Thus, preferred conservative substitution groups are aspartate-glutamate; asparagine-glutamine; valine-leucine-isoleucine; alanine-valine; and phenylalanine-tyrosine. By such mutations e.g. stability and/or effectiveness of a peptide may be enhanced. If mutations are introduced into the peptide, the peptide remains (functionally) homologous, e.g. in sequence, in function, and in antigenic character or other function. Such mutated components of the peptide can possess altered properties that may be advantageous over the non-altered sequences of the peptides of the invention for certain applications (e.g. increased pH optimum, increased temperature stability etc.).

A derivative of the peptide of the invention is defined as having substantial identity with the non-modified sequences of the peptide of the invention. Particularly preferred are amino acid sequences which have at least 30% sequence identity, preferably at least 50% sequence identity, even preferably at least 60% sequence identity, even preferably at least 75% sequence identity, even more preferably at least 80%, yet more preferably 90% sequence identity and most preferably at least 95% or even 99% sequence identity to the naturally occurring analogue. Appropriate methods for synthesis or isolation of a functional derivative of the peptides of the invention as well as for determination of percent identity of two amino acid sequences are described above. Additionally, methods for production of derivatives of the peptides as disclosed above are well known and can be carried out following standard methods which are well known by a person skilled in the art (see e.g., Sambrook J, Maniatis T (1989)).

As a further embodiment, the invention provides pharmaceutical compositions or medicaments comprising the peptides as defined herein. In certain embodiments, such pharmaceutical compositions or medicaments comprise the peptides as well as an optional linker, as defined herein. Additionally, such a pharmaceutical composition or medicament can comprise a pharmaceutically acceptable carrier, adjuvant, or vehicle. A "pharmaceutically acceptable carrier, adjuvant, or vehicle" according to the invention refers to a non-toxic carrier, adjuvant or vehicle that does not destroy the pharmacological activity or physiological targeting of the peptide with which it is formulated. Pharmaceutically acceptable carriers, adjuvants or vehicles that can be used in the pharmaceutical compositions of this invention include, but are not limited to those that can be applied cranially or intracranially, or that can cross the blood-brain barrier (BBB). Notwithstanding this, the pharmaceutical compositions of the invention can include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, topically, rectally, nasally, buccally, vaginally, cerebrally, or via an implanted reservoir.

The term parenteral as used herein includes subcutaneous, intravenous, intramuscular, intra-articular, intra-synovial, intrasternal, intrathecal, intrahepatic, intralesional and intracranial injection or infusion techniques. The pharmaceutical compositions are administered orally, intraperitoneally or intravenously. Sterile injectable forms of the pharmaceutical compositions of this invention may be aqueous or oleaginous suspension. These suspensions can be formulated according to techniques known in the art using suitable dispersing or wetting agents and suspending agents. The sterile injectable preparation can also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

As such, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions herein may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavouring or colouring agents may also be added.

Alternatively, the pharmaceutical composition as defined herein may be administered in the form of suppository for rectal administration. Such a suppository can be prepared by mixing the agent with a suitable non-irritating excipient that is solid at room temperature but liquid at rectal temperature and, therefore, will melt in the rectum to release the drug. Such materials include cocoa butter, beeswax and polyethylene glycols.

The pharmaceutical composition as defined herein may also be administered topically, especially when the target of treatment includes areas or organs readily accessible by topical application, including diseases of the brain, other intra-cranial tissues, the eye, or the skin. Suitable formulations are readily prepared for each of these areas or organs.

For topical applications, the pharmaceutical composition as defined herein may be formulated in a suitable ointment containing the peptides as identified herein, suspended or dissolved in one or more carriers. Carriers for topical administration of the peptide include, but are not limited to, mineral oil, liquid petrolatum, white petrolatum, propylene glycol, polyoxyethylene, polyoxypropylene compound, emulsifying wax and water. Alternatively, the pharmaceutical composition as defined herein can be formulated in a suitable lotion or cream containing the peptide suspended or dissolved in one or more pharmaceutically acceptable carriers. Suitable carriers include, but are not limited to, mineral oil, sorbitan moNOstearate, polysorbate 60, cetyl esters wax, cetearyl alcohol, 2-octyldodecanol, benzyl alcohol and water.

The pharmaceutical composition as defined herein may also be administered by nasal aerosol or inhalation. Such a composition may be prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. The pharmaceutically acceptable composition or medicament herein is formulated for oral or parenteral administration, e.g. by injection.

For treatment purposes, a non-toxic, damage-reducing, effective amount of the peptide may be used for preparation of a pharmaceutical composition as defined above. Therefore, an amount of the peptide may be combined with the carrier material(s) to produce a composition as defined above. The pharmaceutical composition is typically prepared in a single (or multiple) dosage form, which will vary depending upon the host treated and the particular mode of administration. Usually, the pharmaceutical composition is formulated so that a dosage range per dose of 0.0001 to 100 mg/kg body weight/day of the peptide can be administered to a patient receiving the pharmaceutical composition. Preferred dosage ranges per dose vary from 0.01 mg/kg body weight/day to 50 mg/kg body weight/day, even further preferred dosage ranges per dose range from 0.1 mg/kg body weight/day to 10 mg/kg body weight/day. However, dosage ranges and treatment regimens as mentioned above may be adapted suitably for any particular patient dependent upon a variety of factors, including the activity of the specific peptide employed, the age, body weight, general health, sex, diet, time of administration, rate of excretion, drug combination, the judgment of the treating physician and the severity of the particular disease being treated. In this context, administration may be carried with in an initial dosage range, which may be varied over the time of treatment, e.g. by increasing or decreasing the initial dosage range within the range as set forth above. Alternatively, administration may be carried out in a continuous manner by administering a specific dosage range, thereby maintaining the initial dosage range over the entire time of treatment. Both administration forms may furthermore be combined, e.g. if the dosage range is to be adapted (increased or decreased) between various sessions of the treatment but kept constant within the single session so that dosage ranges of the various sessions differ from each other.

The pharmaceutical composition and/or the peptide of the invention can be used for treatment, amelioration or prevention of diseases related to the damaging effect of an injury to cells, particularly mammalian cells, as disclosed herein, particularly for the treatment of neural injuries, including cerebral stroke or spinal cord injuries, epilepsy, perinatal hypoxia-ischemia, ischemic or traumatic injuries to the brain or spinal cord and damages to central nervous system (CNS) neurons including, without being limited thereto, acute CNS injuries, ischemic cerebral stroke or spinal cord injuries, as well as of anoxia, ischemia, mechanical injury, neuropathic pain, excitotoxicity, and related injuries. Furthermore, the pharmaceutical composition and peptides of the invention can be employed for providing a neuroactive or neuroprotective effect against, or treatment of, excitotoxic and ischemic injury, excitotoxicity, lack of neurotrophic support, disconnection, damage to neurons including e.g. epilepsy, chronic neurodegenerative conditions, and the like. In this context, excitotoxicity may be particularly involved in stroke, traumatic brain injury and neurodegenerative diseases of the central nervous system (CNS) such as Multiple sclerosis (MS), Alzheimer's disease (AD), Amyotrophic lateral sclerosis (ALS), neuropathic pain, Fibromyalgia, Parkinson's disease (PD), perinatal hypoxia-ischemia, and Huntington's disease, that can be treated herein. Other common conditions that cause excessive glutamate concentrations around neurons and which may be treated herein are hypoglycemia, vasospasm, benzodiazepine withdrawal and status epilepticus, glaucoma/deterioration of retinal ganglion cells, and the like.

The treatment, amelioration or prevention of diseases related to the damaging effect of an injury to mammalian cells as defined above as well as to further diseases or disorders as mentioned herein is typically carried out by administering a pharmaceutical composition or peptide or mixture of peptides of the invention in a dosage range as described herein. Administration of the pharmaceutical composition or peptides may be carried out either prior to onset of excitotoxicity and/or (ischemic) brain damage, i.e. the damaging effect of an injury to mammalian cells, or concurrent or subsequent thereto; for example, administration of the pharmaceutical composition or peptides may be carried out within a time of (up to) 1 hour (0-1 hours), up to 2 hours, up to 3-5 hours or up to 24 hours or more subsequent to a cerebral stroke or spinal cord injuries, ischemic or traumatic injuries to the brain or spinal cord and, in general, damages to the central nervous system (CNS) neurons. In chronic neurodegenerative disorders (AD, PD, ALS, MS, etc.) treatment may require life-long daily treatment.

When used therapeutically, the compounds of the invention are administered in therapeutically effective amounts. In general, a therapeutically effective amount means an amount necessary to delay the onset of, inhibit the progression of, or halt altogether the particular condition being treated. Therapeutically effective amounts specifically will be those that desirably influence the survival of neurons following stroke or other cerebral ischemic insult. Generally, a therapeutically effective amount will vary with the subject's age and condition, as well as the nature and extent of the disease in the subject, all of which can be determined by one of ordinary skill in the art. The dosage may be adjusted by the individual physician, particularly in the event of any complications being experienced.

As mentioned above, one aspect of the invention relates to nucleic acid sequences and their derivatives which code for an isolated peptide or variant thereof and other nucleic acid sequences which hybridize to a nucleic acid molecule consisting of the above described nucleotide sequences, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers to hybridization at 65° C. in hybridization buffer (3.5×SSC, 0.02% Ficoll, 0.02% Polyvinyl pyrrolidone, 0.02% Bovine Serum Albumin, 25 mMNaH$_2$PO$_4$ (pH7), 0.5% SDS, 2 mM EDTA). SSC is 0.15 M Sodium Chloride/0.15 M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1×SSC/0.1×SDS at 65° C.

The present invention furthermore provides kits comprising the abovementioned pharmaceutical composition (in one or more containers) in at least one of the above formulations and an instruction manual or information brochure regarding instructions and/or information with respect to application of the pharmaceutical composition.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the field of the invention will appreciate that the invention described herein is susceptible to variations and modifications other than those specifically described. It is to be understood that the invention includes all such functional variations and modifications. The invention also includes all of the steps, features, compositions and compounds referred to or indicated in this specification, individually or collectively, and any and all combinations or any two or more of said steps or features. The present invention is not to be limited in scope by the specific embodiments described herein, which are intended for the purpose of exemplification only. Functionally-equivalent products, compositions and methods are clearly within the scope of the invention, as described herein. Furthermore, the present invention is performed without undue experimentation using, unless otherwise indicated, conventional techniques of molecular biology, microbiology, neurobiology, virology, recombinant DNA technology, peptide synthesis in solution, solid phase peptide synthesis, and immunology, or techniques cited herein.

The Applicant has found, surprisingly, that certain CPPs, especially arginine-rich peptides exhibit neuroprotective efficacy without the traditional requirement for being fused to previously identified neuroprotective peptides. Certain of these CPPs also exhibit low toxicity and are functional at low doses or concentrations. These CPPs include penetratin (SEQ ID NO: 22) and Pep-1 (SEQ ID NO: 23). More surprisingly, however, the Applicant has also found that long stretches of basic (i.e. cationic) amino acids such as poly-arginine peptides of between 10 and 20 residues (inclusive) in length, preferably 10 to 18 residues (inclusive) in length, and certain peptides containing more than 10 arginine residues, such as protamine (SEQ ID NOs: 32 to 36) or LMWP (SEQ ID NO: 37), exhibit greatly enhanced neuroprotective activity when compared to these CPPs, and especially when compared at similar concentrations to shorter arginine-rich sequences such as R1 to R8 (SEQ ID NOs: 1 to 5). In particular, R12 (SEQ ID NO: 9), R15 (SEQ ID NO: 12), R18 (SEQ ID NO: 13), when assayed in glutamic acid and or in vitro ischemia injury models, provided enhanced neuroprotection when compared to the CPPs mentioned above. The two different neuronal injury models are likely to activate different damaging cellular pathways and thereby will provide further insight into the neuroprotective spectrum and possible mode of action of the peptides of the invention.

In this specification, the abbreviation "Arg" followed by an integer indicates the number of arginine repeats in a peptide. Thus, Arg-15 (abbreviated as R15; SEQ ID NO: 12), following the IUPAC single letter abbreviation for arginine) refers to consecutive arginine residues in a peptide formation. As far as practicable, however, this specification will refer to the single letter amino acid code, i.e. R15 (SEQ ID NO: 12), instead of Arg-15 R15 (SEQ ID NO: 12), for example.

Neuronal Disorders Involving Neuronal Cell Death

Neuronal disorders such as migraine, stroke, traumatic brain injury, spinal cord injury epilepsy, perinatal hypoxia-ischemia and neurodegenerative disorders including Huntington's Disease (HD), Parkinson's Disease (PD), Alzheimer's Disease (AD) and amyotrophic lateral sclerosis (ALS) are major causes of morbidity and disability arising from long term brain injury. The brain injuries generally involve a range of cell death processes including apoptosis, autophagy, necroptosis and necrosis, and affect neurons astrocytes, oligodentrocytes, microglia and vascular endothelial cells (collectively referred to as the neurovascular unit; NVU). The damaging triggers involved in neural injury involve diverse pathways involving glutamate excitotoxicity calcium overload, oxidative stress, proteolytic enzymes and mitochondrial disturbances. As used herein, the term "stroke" includes any ischemic disorder affecting the brain or spinal cord, e.g. thrombo-embolic occlusion in a brain or spinal cord artery, severe hypotension, perinatal hypoxia-ischaemia, a myocardial infarction, hypoxia, cerebral haemorrhage, vasospasm, a peripheral vascular disorder, a venous thrombosis, a pulmonary embolus, a transient ischaemic attack, lung ischemia, unstable angina, a reversible ischemic neurological deficit, adjunct thrombolytic activity, excessive clotting conditions, cerebral reperfusion injury, sickle cell anemia, a stroke disorder or an iatrogenically induced ischemic period such as angioplasty, or cerebral ischemia.

Increased extracellular levels of the neurotransmitter glutamate can cause neuronal cell death via acute and delayed damaging processed caused by excitotoxicity. An accumulation of extracellular glutamate over-stimulates NMDA and AMPA receptors and subsequently, VGCCs, NCX, TRMP2/7, ASIC and mGlu receptors resulting in an influx of extracellular calcium and sodium ions and the release of bound calcium from intracellular stores. Over-activation of NMDA receptors can also trigger the production of damaging molecules (e.g. nitric oxide, CLCA1; calcium-activated chloride channel regulator 1, calpain, SREBP1: sterol regulatory element binding protein-1) and signaling pathways (e.g. DAPK; death-associated protein kinase, CamKII: calcium-calmodulin-dependent protein kinase II). The increase in intracellular calcium initiates a range of cell damaging events involving phospholipases, proteases, phosphatases, kinases and nitric oxide synthase, as well as the activation of pathways triggering cell death (i.e. apoptosis, autophagy, necroptosis and necrosis).

Since the peptides of the invention are shown herein to protect neurons from death, the disclosures contained in WO2009133247 and EP 1969003 show that the peptides of the invention also find application in the treatment and/or prevention of Alzheimer's disease, Parkinson's disease, amyotrophic lateral sclerosis, stroke, peripheral neuropathy, or epilepsy and accordingly to other associated pathologies described herein. Accordingly, the present invention is directed to a method for treatment of Alzheimer's disease, Parkinson's disease, amyotrophic lateral sclerosis, stroke, peripheral neuropathy, epilepsy, spinal cord injury, diabetes or drug addiction, wherein a pharmaceutically effective amount of any one or more of the peptides of the invention is administered to a patient. In other words, the peptides according to the present invention are for use in the treatment of injuries associated with ischemia, as well as Alzheimer's disease (AD), Huntington's disease (HD), Parkinson's disease (PD), multiple sclerosis (MS), acute disseminated encephalomyelitis (ADEM), amyotrophic lateral sclerosis (ALS), stroke, peripheral neuropathy, epilepsy, spinal cord injury and other related pathologies described herein.

In pharmaceutical applications, the peptides can also be entrapped in microcapsules prepared, for example, by co-acervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in Remington's Pharmaceutical Sciences. This may also be accomplished using sustained-release preparations. Suitable examples of sustained-release preparations include semipermeable matrices of solid hydrophobic polymers containing the peptide, which matrices are in the form of shaped articles, e.g., films, or microcapsules. Examples of sustained-release matrices include polyesters, hydrogels as described by Langer et al., J. Biomed. Mater. Res., 15: 167-277 (1981) and Langer, Chem. Tech., 12:98-105 (1982) or polyvinylalcohol, polylactides (U.S. Pat. No. 3,773,919, EP 58,481), or non-degradable ethylene-vinyl acetate.

In one embodiment, a pharmaceutical composition comprising the peptide of the invention as defined above is for use in the treatment of ischemic injury, Alzheimer's disease, Parkinson's disease, amyotrophic lateral sclerosis, stroke, peripheral neuropathy, or epilepsy. In another embodiment, the present invention provides a method for promoting survival of neurons comprising the step of contacting neurons with the peptides of the invention, or combinations thereof. The method can be performed in vitro as is shown herein.

The publications and other materials used herein to illuminate the background of the invention, and in particular, to provide additional details with respect to its practice, are incorporated herein by reference. The present invention is further described in the following examples, which are not intended to limit the scope of the invention.

Examples (Poly-Arginine and Arginine-Rich and Arginine-Rich Protamine Peptides of Tables 1, 2 and 5 Below)

Protamine Sulphate, Protamine Peptides and Other Peptides

Peptides listed in Table 5. Protamine sulphate (protamine; Ptm, SEQ ID NOs: 32 to 35) was obtained from Sanofi Aventis. Low molecular weight protamine (LMWP; SEQ ID NO: 37) was synthesised by Mimotopes Pty Ltd (Australia). Protamine peptides 1-5 (Ptm1, Ptm2, Ptm3, Ptm4, Ptm5; SEQ ID NOs: 32, 33, 34, 35 and 36, respectively) were synthesised by Pepmic Co Ltd (China). The peptides were HPLC purified to greater than 90-98%. All peptides were prepared as 100× stocks (500 µM) in normal saline and assessed in a concentration range from 0.1-10 µM, dependent upon injury model.

It should be noted that protamine sulphate (protamine; Ptm) is a mixture of Ptm1-Ptm4[1] (SEQ ID NOs: 32 to 35). The protamine peptides (Ptm, Ptm1-5, LMWP; SEQ ID NOs: 32 to 36) are arginine-rich.

Methods (Poly-Arginine and Arginine-Rich Peptides)

Primary Neuronal Cortical Cultures

Establishment of cortical cultures was as previously described (Meloni et al., 2001). Briefly, cortical tissue from E18-E19 Sprague-Dawley rats was dissociated in Dulbecco's modified Eagle medium (DMEM; Invitrogen, Australia) supplemented with 1.3 mM L-cysteine, 0.9 mM NaHCO$_3$, 10 units/ml papain (Sigma, USA) and 50 units/ml DNase (Sigma) and washed in cold DMEM/10% horse serum. Neurons were resuspended in Neurobasal (Invitrogen) containing 2% B27 supplement (B27; Invitrogen). Before seeding, 96-well sized glass wells (6 mm diameter, ProTech, Australia) or 96-well plastic plates (ProSciTech, Australia) were coated with poly-D-lysine overnight (50 ml/well: 50 mg/mL; 70-150 K, Sigma). Excess poly-D-lysine solution was then removed and replaced with Neurobasal (containing 2% B27; 4% fetal bovine serum; 1% horse serum; 62.5 mM glutamate; 25 mM 2-mercaptoethanol; and 30 mg/mL streptomycin and 30 mg/mL penicillin). Neurons were plated to obtain ≈10,000 viable neurons for each well on day in vitro 11-12. Neuronal cultures were maintained in a CO$_2$ incubator (5% CO$_2$, 95% air balance, 98% humidity) at 37° C. On day in vitro 4 one third of the culture medium was removed and replaced with fresh Neurobasal/2% B27 containing the mitotic inhibitor, cytosine arabinofuraNOside (1 mM final concentration; Sigma). On day in vitro 8 one half of the culture medium was replaced with Neurobasal/2% B27. Cultures were used on day in vitro 11 or 12 after which time they routinely consist of >97% neurons and 1-3% astrocytes (Meloni et al., 2001).

Other Cell Lines Used

A brain endothelial cell line (bEND3) and a neuroblastoma cell line (SH-SY5Y) were also used for some experiments. bEND3 and SH-SY5Y cells were cultured using standard techniques in DMEM plus 5 or 15% foetal calf serum. Rat primary astrocytes were obtained and cultured as described for cortical neurons except DMEM plus 10% foetal calf serum was used instead of Neurobasal/2% B27, and the mitotic inhibitor, cytosine arabinofuranoside was not used.

Cell Penetrating Peptides And Control Peptides

Peptides listed in Table 1 were synthesised by Mimotopes Pty Ltd (Australia), except TAT-L (SEQ ID NO: 21), which was synthesised by Pepscan Presto (The Netherlands), and R9/tPA/R9 (SEQ ID NO: 16), NCXBP3 (SEQ ID NO: 30) and R9/X7/R9 (SEQ ID NO: 16), which were synthesised by China Peptide Co., Ltd. Peptides listed in Table 2 were synthesised by China Peptides (China). The peptides were HPLC purified to greater than 88-96%. TAT-L (SEQ ID NO: 21), penetratin (SEQ ID NO: 22), R9 (SEQ ID NO: 6) and Pep-1 (SEQ ID NO: 23) were synthesised in the L-isoform and TAT-D (SEQ ID NO: 20) and Arg9-D (SEQ ID NO: 19) in the protease resistant D-retro-inverso form, synthesised from D-amino acids in reverse sequence (referred to as D-isoform hereafter) (Brugidou et al., 1995) (Table 1). A TAT-fused JNK inhibitory peptide (JNKI-1 D-TAT; SEQ ID NO: 25) in the D-isoform and a TAT-fused AP-1 inhibitory peptide (PYC36L-TAT; SEQ ID NO: 24) in the L-isoform were used as positive controls (Table 1; Borsello et al., 2003; Meade et al., 2010b). All peptides were prepared as 100× stocks (500 µM) in normal saline and assessed in a concentration range from 0.1-15 µM, dependent upon injury model. The TAT-L (SEQ ID NO: 21) peptide was only used in the glutamic acid excitotoxicity model.

TABLE 1

Amino acid sequences, molecular weights and charge of peptides

| Peptide | SEQ ID NO. | Sequence | No. amino acids/No. arginine residues: molecular weight (Da) | Net charge at pH 7 | Physical-chemical properites |
|---|---|---|---|---|---|
| R1: Arg-1 | 1 | H-R-OH | 1/1: 174 | 1 | Cationic |
| R3: Arg-3 | 2 | H-RRR-OH | 3/3: 487 | 3 | Cationic |
| R6: Arg-6 | 3 | H-RRRRRR-OH | 6/6: 955 | 6 | Cationic |
| R7: Arg-7 | 4 | H-RRRRRRR-OH | 7/7: 1,111 | 7 | Cationic |
| R8: Arg-8 | 5 | H-RRRRRRRR-OH | 8/8: 1,267 | 8 | Cationic |
| R9: Arg-9 | 6 | H-RRRRRRRRR-OH | 9/9: 1,424 | 9 | Cationic |
| R10: Arg-10 | 7 | H-RRRRRRRRRR-OH | 10/10: 1,580 | 10 | Cationic |
| R11: Arg-11 | 8 | H-RRRRRRRRRRR-OH | 11/11: 1,736 | 11 | Cationic |
| R12: Arg-12 | 9 | H-RRRRRRRRRRRR-OH | 12/12: 1,892 | 12 | Cationic |
| R13: Arg-13 | 10 | H-RRRRRRRRRRRRR-OH | 13/13: 2,048 | 13 | Cationic |
| R14: Arg-14 | 11 | H-RRRRRRRRRRRRRR-OH | 14/14: 2,204 | 14 | Cationic |
| R15: Arg-15 | 12 | H-RRRRRRRRRRRRRRR-OH | 15/15: 2,360 | 15 | Cationic |
| R18: Arg-18 | 13 | H-RRRRRRRRRRRRRRRRRR-OH | 18/18: 2,829 | 18 | Cationic |
| PTD-4[a] | 14 | H-YARAAARQARA-OH | 11/3: 1,204 | 3 | Cationic |
| E9/R9 (R9/E9) | 15 | H-EEEEEEEEE-RRRRRRRRR-OH | 18/9: 2,586 | 0 | Neutral |
| R9/tPA/R9 or R9/X7/R9 | 16 | H-RRRRRRRRR-PGRVVGG-RRRRRRRRR-OH | 25/19: 3,452 | 19 | Cationic |
| DAHK | 17 | H-DAHK-OH | 4/0: 469.5 | 0.1 | N/A |
| NR2B9c-TAT[b] | 18 | H-GRKKRRQRRR-KLSSIESDV-NH2 | 19/6: 2,355 | | Cationic |
| D-R9 | 19 | H-rrrrrrrrr-NH2 | 9/9: 1423.73 | 10 | Cationic |
| TAT-D | 20 | H-GrrrqrrkkrG-NH2 | 10/6: 1,453 | 9 | Cationic |
| TAT-L | 21 | Ac-GRKKRRQRRRG-NH2 | 10/6: 1,494 | 8 | Cationic |

TABLE 1-continued

Amino acid sequences, molecular weights and charge of peptides

| Peptide | SEQ ID NO. | Sequence | No. amino acids/No. arginine residues: molecular weight (Da) | Net charge at pH 7 | Physical-chemical properites |
|---|---|---|---|---|---|
| Penetratin | 22 | H-RQIKIWFQNRRMKWKK-NH2 | 16/3: 2,246 | 7 | Cationic |
| Pep-1 | 23 | H-KETWWETWWTEWSQPKKKRKV-NH2 | 21/1: 2,847 | 4 | Amphiphilic |
| PYC36L-TAT[c] | 24 | H-GRKKRRQRRR-GGLQGRRRQGYQSIKP-NH2 | 26/10: 3,180 | 13 | Cationic |
| JNK1-1D-TAT[d] | 25 | H-tdqsrpvqpflnlttprkprpp-rrrqrrkkrg-NH2 | 32/: 3,925 | 12 | Cationic |
| TAT-JNKI-1[d] | 26 | H-GRKKRRQRRR-PPRPKRPTTLNLFPQVPRSQDT-OH | 32/9: 3,924.6 | 11 | Cationic |
| kFGF-JNKI-1 | 27 | H-AAVALLPAVLLALLAP-PPRPKRPTTLNLFPQVPRSQDT-OH | 38/3: 4,043.9 | 3 | Hydrophobic |
| kFGF | 28 | H-AAVALLPAVLLALLAP-OH | 16/0: 1515.96 | 0 | Hydrophobic |
| XIP[e] | 29 | H-RRLLFYKYVYKRYRAGKQRG-OH | 20/5: 2621.14 | 8 | Cationic |
| NCXBP3[f] | 30 | H-RRERRRRSCAGCSRARGSCRSCRR-NH2 | 24/11: 2881.34 | 10.8 | Cationic |
| Cal/R9 | 31 | Ac-PLFAE-RRRRRRRRR-NH2 | 15/9: 2022.41 | 8 | Cationic |

At the N-terminus, H indicates free amine, and Ac indicates acetyl. At the C-terminus OH indicates free acid and NH2 indicates amide. AA = amino acids. Lower case single letter code indicates D-isoform of the amino acid. [a]Peptide describe in Ho et al (2001), [b]NR2B9c-TAT also shown as NA-1 (Aarts et al., 2002; Hill et al 2012), [c]peptide described in Meade et al. 2010ab and isolated by Phylogical Ltd, [d]peptide descirbed in Borsello et al. 2003, [e]XIP described by He et al., 1997, [f]peptide isolated by Jane Cross/Bruno Meloni from phylomer library (Phylogica Pty Ltd).

Glutamic Acid and Kainic Acid and NMDA Excitotoxicity Models and Peptide Incubation Peptides were added to culture wells (96-well plate format) 15 minutes prior to glutamic acid or kainic acid exposure by removing media and adding 50 µl of Neurobasal/2% B27 containing CPPs, control peptides or MK801/CNQX. To induce excitotoxicity, 50 µl of Neurobasal/2% B27 containing glutamic acid (200 PM) or kainic acid (400 µM) or NMDA (200 µM) was added to the culture wells (100 µM glutamic acid, 200 µM kainic acid and NMDA 100 µM final concentration). Cultures were incubated at 37° C. in the $CO_2$ incubator for 5 minutes for glutamic acid, 45 minutes for kainic acid and 10 minutes for NMDA exposure, after which time the media was replaced with 100 µl of 50% Neurobasal/2% N2 supplement (Invitrogen) and 50% balanced salt solution (BSS; see below). Cultures were incubated for a further 24 hours at 37° C. in the $CO_2$ incubator. The untreated controls with or without glutamic acid or kainic acid treatment received the same wash steps and media additions.

In one experiment, following the 15 minute CPP incubation (5 or 10 µM), the media in wells was removed and wells washed once in 300 µl of BSS before the addition of Neurobasal/2% B27 containing glutamic acid (100 µM/100 µl). Following this step, cultures were treated as described above. Untreated controls with or without glutamic acid exposure received the same wash steps and media additions. In addition, a post-glutamic acid exposure CPP treatment (5 µM) experiment was performed for the R9 (SEQ ID NO: 6) peptide and the JNKI-1 D-TAT (SEQ ID NO: 25) control peptide. In this experiment, neurons were exposed to glutamic acid (100 µM) in 100 µl Neurobasal/2% B27 for 5 minutes as described above, after which time the media was removed and replaced with 50 µl Neurobasal/2% N2 supplement, followed by peptide (10 µM/50 µl in BSS) addition at 0 and 15 minutes post-glutamic acid exposure.

For pre-glutamic acid exposure experiments, neurons were exposed to peptide(s) for a 10 minute period, immediately before or 1, 2, 3, 4 or 5 hours prior to glutamic acid exposure. This was performed by removing media and adding 50 µl of Neurobasal/2% B27 containing peptide. After the 10 minutes at 37° C. in the $CO_2$ incubator, media was removed and replaced with 100 µl of Neurobasal/2% B27 (for immediate glutamic acid exposure media contained glutamic acid; 100 µM). At the relevant peptide pre-treatment time, media was removed and replaced with 100 µl of Neurobasal/2% B27 containing glutamic acid (100 PM). Following 5-minute glutamic acid exposure, neuronal culture wells were treated as described above. For all experiments untreated controls with or without glutamic acid treatment underwent the same incubation steps and media additions.

Heparin Experiments

Heparin (for injection) was obtained from Pfizer (1000 IU/ml). Two different heparin experiments were performed: 1. Peptides were incubated with heparin (20 IU/ml) in Neurobasal/B27 for 5 minutes at room temperature, before addition to culture wells (50 µl) for 15 minutes at 37° C. in the $CO_2$ incubator. Following the incubation period, media in wells was removed and replaced with 100 µl of Neurobasal/2% B27 containing glutamic acid (100 µM), and subsequently treated as described above; 2. Media in wells was replaced with Neurobasal/2% B27 containing heparin (50 µl; 40 IU/ml) and incubated for 5 minutes at 37° C. in the $CO_2$ incubator. After the incubation period, peptides or glutamate receptor blockers (MK801/CNQX) in Neurobasal/2% B27 (50 µl) were added to the culture wells and cultures incubated for a further 10 minutes at 37° C. in the $CO_2$ incubator. Following the incubation period, media in wells was removed and replaced with 100 µl of Neurobasal/2% B27 containing glutamic acid (100 µM), and subsequently treated as described above. For all experiments, non-heparin treated peptide controls with glutamic acid treatment underwent the same incubation steps and media additions.

In Vitro Ischemia/OGD Model and Peptide Incubation

The in vitro ischemia model used for primary cortical neuronal cultures was performed as previously described (Meloni et al., 2011). Briefly, culture media was removed from wells (glass 96-well plate format) and washed with 315 µl of glucose free balanced salt solution (BSS; mM: 116 NaCl, 5.4 KCl, 1.8 $CaCl_2$, 0.8 $MgSO_4$, 1 $NaH_2PO_4$; pH 6.9) before the addition of 60 µl BSS containing cell penetrating or control peptides (see Table 1). A non-peptide positive control consisting of the glutamate receptor blockers (5 µM MK801/5 µM 6-cyano-7-nitroquinoxaline: MK801/CNQX) was also included. In vitro ischemia was initiated by placing wells in an anaerobic incubator (Don Whitely Scientific, England; atmosphere of 5% $CO_2$, 10% $H_2$ and 85% argon, 98% humidity) at 37° C. for 55 minutes. Upon removal from the anaerobic incubator, 60 µl of Neurobasal/2% N2 supplement was added to the wells and cultures incubated for a further 24 hours at 37° C. in the $CO_2$ incubator. Control cultures received the same BSS wash procedures and media additions as ischemic treated cultures before incubation at 37° C. in the $CO_2$ incubator.

For pre-OGD exposure experiments the procedure was the same as described in the glutamic acid model, except the 10 minute peptide pre-treatment was performed using 100 µl Neurobasal/2% B27. Control cultures underwent the same BSS wash procedures and media additions as OGD treated cultures.

The in vitro ischemia model was also used for bEND3 cells, SH-SY5Y cells, and astrocytes. For bEND3 cells anaerobic incubation was extended to 2-3 hours and upon removal from the anaerobic incubator, 60 µl of DMEM/2% FCS was added to wells. For SH-SY5Y cells the first BSS wash step (315 µl) was omitted and anaerobic incubation was extended to 2-5 hours. Upon removal from the anaerobic incubator, 60 µl of DMEM/2% FCS was added to wells. For astrocytes, anaerobic incubation was extended to 1:15 to 2:00 hours and upon removal from the anaerobic incubator, 60 µl of DMEM/2% FCS was added to wells.

In Vitro Neuronal, bEND3 and Astrocyte Toxicity Model and Peptide Incubation

For neuronal cultures peptides were added to culture wells (96-well plate format) by removing media and adding 100 µl of 50% Neurobasal/2% N2 supplement and 50% BSS containing CPPs, JNKI-1 D-TAT (SEQ ID NO: 25) or TAT-NR2B9c (SEQ ID NO: 18). Control cultures received of 50% Neurobasal/2% N2 supplement and 50% BSS media only. Cultures were incubation at 37° C. in the $CO_2$ incubator for 20 hours, after which time cell viability was assessed using the MTS assay. For bEND3 cultures, peptides were added to culture wells (96-well plate format) by removing media and adding 100 µl of DMEM/2% FCS containing peptide. Control cultures received 100 µl of DMEM/2% FCS only. Cultures were incubation at 37° C. in the $CO_2$ incubator for 0.5, 1 or 2 hours, after which time cell viability was assessed using the MTS assay. For astrocyte cultures peptides were added to culture wells (96-well plate format) by removing media and adding 100 µl of DMEM/2% FCS containing peptide. Control cultures received 100 µl of DMEM/2% FCS only. Cultures were incubation at 37° C. in the $CO_2$ incubator for 24 hours, after which time cell viability was assessed using the MTS assay.

Cell Viability Assessment and Statistical Analysis

Twenty-four hours after insult, neuronal cultures were examined by light microscopy for qualitative assessment of neuronal cell viability. Neuronal viability was quantitatively measured by 3-(4,5,dimethyliazol-2-yl)-5-(3-carboxymethoxy-phenyl)-2-(4-sulfophenyl)-2H-tetrazolium salt (MTS) assay (Promega, Australia). The MTS assay measures the cellular conversion of the tetrazolium salt to a water-soluble brown formazan salt, which is detected spectrophotometrically at 490 nm. MTS absorbance data were converted to reflect proportional cell viability relative to both the untreated and treated controls, with the untreated control taken as 100% viability, and presented as mean±SEM. For studies using astrocytes, bEND3, and SH-SY5Y cells, raw MTS data was used to generate graphs. Viability data was analysed by ANOVA, followed by post-hoc Fischer's PLSD test, with $P<0.05$ values considered statistically significant. Four- to six wells were used in all assays.

Rat Permanent Focal Cerebral Ischemia Model—Experimental Groups and Treatments

All treatments were randomized and administered in a blinded manner. Administration of peptide (D-R9: rrrrrrrrr-NH2: SEQ ID NO: 19; R12: SEQ ID NO: 9, R15: SEQ ID NO: 12, R18: SEQ ID NO: 13, protamine sulphate; Ptm1-4 mixture SEQ ID NOs: 32 to 35) or vehicle (saline: 0.9% NaCl) treatment solution was performed at 30 min post-MCAO. The peptide treatment comprised D-R9 (SEQ ID NO: 19) in saline (600 µl) to provide an intravenous loading dose of 1 µmol/kg or 1000 nmol/kg given over 5-6 min via the right jugular vein.

Rat Permanent Focal Cerebral Ischemia Model

This study was approved by the Animal Ethics Committee of the University of Western Australia. Male Sprague Dawley rats weighing 270 g to 350 g were kept under controlled housing conditions with 12 hour light-dark cycle with free access to food and water. Experimental animals were fasted overnight and subjected to permanent middle cerebral artery occlusion (MCAO) as follows.

Anaesthesia was induced with 4% isoflurane and a 2:1 mix of $N_2O$ and $O_2$ via mask. Anaesthesia was maintained at 1.7-2% isoflurane. Cerebral blood flow (CBF) was monitored continuously using laser Doppler flowmetry (Blood FlowMeter, AD Instruments, Sydney, Australia). The probe was located 1 mm caudal and 4 mm lateral (right) to the bregma. A cannula was inserted in the right femoral artery to continuously monitor blood pressure and to provide samples for blood glucose and blood gas readings. Blood glucose was measured using a glucometer (MediSense Products, Abbott Laboratories, Bedford, MA, USA) and blood gases were measured using a blood gas analyser (ABL5, Radiometer, Copenhagen, Denmark). Blood pressure was maintained at 80-100 mmHg. During surgery, rectal temperature was maintained at 37±0.5° C. and warming applied with a fan heater when necessary. For intravenous infusions, a length of PVC line primed with heparinised saline was tied in place in the right jugular vein, then externalised through a dorsal mid-scapular incision to a tether/swivel system (Instech Laboratories, Philadelphia, USA) designed to permit free movement.

The right common carotid artery (CCA) was exposed via a ventral neck incision. The external carotid artery (ECA) was isolated after cauterisation of the superior thyroid and occipital arteries. The isolated section of the ECA was ligated and cauterised to create a stump. The carotid body was removed and the pterygopalatine artery was ligated. A 4-0 nylon monofilament with a 0.39 mm diameter silicone tip (Doccol, Redlands, CA, USA) was inserted through the ECA stump into the CCA and advanced rostrally into the internal carotid artery (ICA) until the laser Doppler flowmetry recorded a >30% decrease from baseline of cerebral blood flow. The monofilament was secured in two places (at the base of the ECA stump and on the ICA) for the remainder of the experiment. Animals were given post-operative analgesia consisting of pethidine (3 mg/kg intramuscular) and bupivacaine (1.5 mg/kg subcutaneously) at head and leg incision sites.

Post-surgery animals were allowed to recover in a climate-controlled chamber and their core body temperature monitored and maintained at 37±0.5° C. by a cooling/heating fan when required for 3-4 hours.

Tissue Processing and Infarct Volume Measurement

Animals were sacrificed 24 hours post-MCAO with intraperitoneal injections of sodium pentobarbitone (900 mg/kg). After euthanasia, the brain was removed and placed in a sterile container of 0.9% NaCl and then placed in a −80° C. freezer for 7 minutes. The brain was then coronally sliced from the junction of the cerebellum and cerebrum to 12 mm rostral to this point in 2 mm thick slices. Slices were immediately stained with 1% 2,3,5 triphenyltetrazolium chloride (TTC, Sigma, St Louis, MO, USA) at 37° C. for 20 minutes, followed by fixation in 4% formalin at room temperature for at least 18-24 hours before infarct volume measurement. Slices were scanned and images were analysed by an operator blind to treatment status using ImageJ $3^{rd}$ edition (NIH, USA). The total infarct volume was determined by adding the areas of infarcted tissue on both sides of the 2 mm sections. These measured areas were multiplied by half slice thickness (1 mm), and corrected for cerebral oedema by multiplying the ratio of affected to normal hemisphere areas.

Statistical Analysis

For infarct volume measurements, the peptide treatment group was compared to the vehicle control group by student t-test [(R9-D (SEQ ID NO: 19) trial)] or ANOVA, followed by post-hoc Fischer's PLSD test [(R12 (SEQ ID NO: 9), R15 (SEQ ID NO: 12), R18 (SEQ ID NO: 13) and Ptm (Ptm1-4 mixture; SEQ ID NOs: 32 to 35) trial)].

Experimental Example 1

Neuroprotection Following Glutamic Acid Exposure

The CPPs TAT-D (SEQ ID NO: 20), R9 (SEQ ID NO: 6), and penetratin (SEQ ID NO: 22) provided significant neuroprotection in a dose response manner (FIG. 1a, Table 3). Visual assessment of cultures post-injury also confirmed the neuroprotective effect that ranged from ≈5% for untreated glutamic acid exposed cultures to 100% survival for R9 (SEQ ID NO: 6) treated cultures. R9 (SEQ ID NO: 6) was the most potent peptide with an IC50 value of 0.78 µM, followed by penetratin (SEQ ID NO: 22) (IC50: 3.4 µM) and TAT-D (SEQ ID NO: 20) (IC50: 13.9 µM). The Pep-1 (SEQ ID NO: 23) peptide was ineffective. The glutamate receptors blockers and control peptides (JNKI-1 D-TAT; SEQ ID NO: 25, PYC36L-TAT; SEQ ID NO: 24) were also highly effective in this model (FIG. 1a).

In addition, the TAT-D (SEQ ID NO: 20) peptide displayed a similar level of neuroprotection as the TAT-L (SEQ ID NO: 21) peptide (FIG. 1b). When CPPs were washed-out prior to glutamic acid exposure only R9 (SEQ ID NO: 6) (in this experiment) displayed high level neuroprotection (FIG. 1c).

The R9 (SEQ ID NO: 6) and R12 (SEQ ID NO: 9) peptides were also highly effective when added immediately after glutamic acid exposure, and R9 (SEQ ID NO: 6) mildly effective when added at 15 minutes post-insult. In contrast, the JNKI-1 D-TAT (SEQ ID NO: 25) and NR2B9c (SEQ ID NO: 18) (also referred to as TAT-NR2B9c) peptides did not significantly increase neuronal survival when added immediately after, or at 15 minutes post-glutamate exposure (FIG. 1d).

FIGS. 1e-j provide additional efficacy data in the glutamate model for peptides R1 (SEQ ID NO: 1), R3 (SEQ ID NO: 2), R6 (SEQ ID NO: 3), R9 (SEQ ID NO: 6), R12 (SEQ ID NO: 9), R15 (SEQ ID NO: 12), R18 (SEQ ID NO: 13), R9/E9 (SEQ ID NO: 15) (also referred to as E9/R9), R9/tPA/R9 (SEQ ID NO: 16) (also referred to as R9/X7/R9) as well as control peptides JNKI-1 D-TAT (SEQ ID NO: 25) and NR2B9c (SEQ ID NO: 18).

In dose response studies using R1 (SEQ ID NO: 1), R3 (SEQ ID NO: 2), R6 (SEQ ID NO: 3), R7 (SEQ ID NO: 4), R8 (SEQ ID NO: 5), R9 (SEQ ID NO: 6), R12 (SEQ ID NO: 9), R15 (SEQ ID NO: 12), R18 (SEQ ID NO: 13) in the glutamate model revealed that: i) R1 (SEQ ID NO: 1), R3 (SEQ ID NO: 2), R6 (SEQ ID NO: 3) and R7 (SEQ ID NO: 4) displayed no to little neuroprotection; ii) R8 (SEQ ID NO: 5) displayed neuroprotection at 5 µM, (iii) the order of potency for the other peptides was R15 (SEQ ID NO: 12) >R18 (SEQ ID NO: 13) >R12 (SEQ ID NO: 9) >R9 (SEQ ID NO: 6); and iv) neuroprotective efficacy for R15 (SEQ ID NO: 12) and R18 (SEQ ID NO: 13) was reduced at the higher concentration (5 µM); see Table 4, FIG. 1e, 1l, 1j, 6, 7, and 8.

In a dose response study using R9 (SEQ ID NO: 6), DAHK (SEQ ID NO: 17) (last four end N-terminal amino acids of protein albumin) PTD-4 (SEQ ID NO: 14) (modified TAT (SEQ ID NO: 21) peptide with 33× increased cell penetrating ability; (Ho et al., 2001), R9/E9 (Arg-9/Glu-9; neutral peptide; SEQ ID NO: 15) and R9/tPA/R9 (SEQ ID NO: 16) (tissue plasminogen activator enzyme peptide cleavage site flanked by R9; SEQ ID NO: 6) in the glutamate model revealed that: i) PTD-4 (SEQ ID NO: 14) and R9/E9 (SEQ ID NO: 15) displayed no to little neuroprotection; DAHK (SEQ ID NO: 17) had low level neuroprotection; and ii) R9/tPA/R9 (SEQ ID NO: 16) had a potency between R12 (SEQ ID NO: 9) and R18 (SEQ ID NO: 13). Also the TAT-NR2B9c peptide (SEQ ID NO: 18) (C-terminal NR2B NMDRA receptor subunit peptide; blocks NMDAR signaling with PSD-95 protein to block NO (nitrous oxide) production; Aarts et al. 2002) was ineffective. See Table 4 and FIGS. 1d, g, h.

Peptide R12 (SEQ ID NO: 9) was more effective than R9 (SEQ ID NO: 6) (based on neuroprotection at 0.625 µM concentration) and both were more effective compared to PCY-36-TAT (SEQ ID NO: 24), in the glutamic acid model, while NR2B9c (SEQ ID NO: 18) was ineffective (FIG. 1g). Peptide R12 (SEQ ID NO: 9) was more effective than R9 (SEQ ID NO: 6) (based on neuroprotection at 0.5 µM and 1 µM concentrations, while R1 (SEQ ID NO: 1), R3 (SEQ ID NO: 2), R6 (SEQ ID NO: 3) and NR2B9c (SEQ ID NO: 18) were ineffective (FIG. 1i). Peptide R9 (SEQ ID NO: 6) synthesized by two different companies also had similar efficacy in the glutamate model (FIG. 1j).

Figure 28:
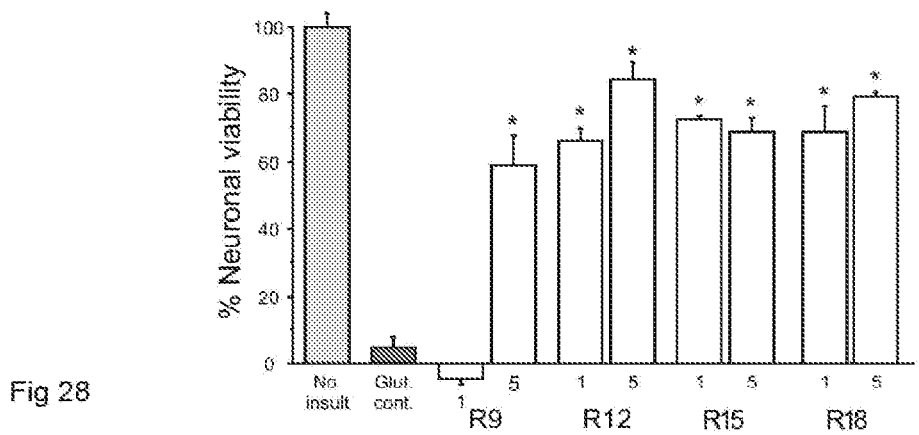
FIG. 28 shows neuroprotective efficacy of R9 (SEQ ID NO: 6), R12 (SEQ ID NO: 9), R15 (SEQ ID NO: 12) and R18 (SEQ ID NO: 13) in the glutamate excitotoxicity model when peptides present in neuronal cultures only during 5-min glutamic acid exposure. Neuronal viability measured 20-24 h following glutamic acid. Concentration of peptide in µM. MTS data were expressed as percentage neuronal viability with no insult control taken as 100% viability (mean±SD; n=4; *P<0.05).
Figure 29:
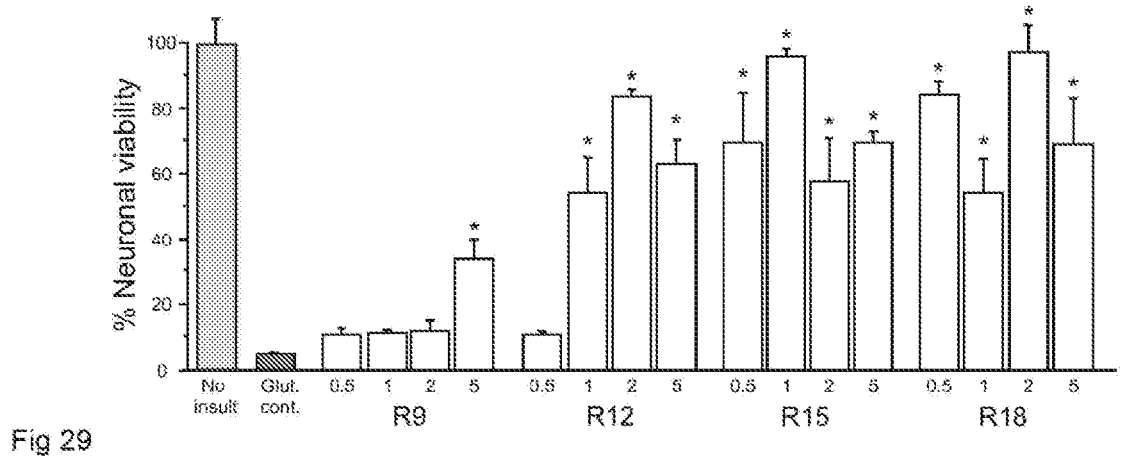
FIG. 29 shows neuroprotective efficacy of R9 (SEQ ID NO: 6), R12 (SEQ ID NO: 9), R15 (SEQ ID NO: 12) and R18 (SEQ ID NO: 13) in the glutamate model when peptides present in neuronal cultures for 10 min only prior to glutamic acid exposure. Neuronal viability measured 20-24 h following glutamic acid. Concentration of peptide in µM. MTS data were expressed as percentage neuronal viability with no insult control taken as 100% viability (mean±SD; n=4; *P<0.05).

Peptides R9 (SEQ ID NO: 6), R12 (SEQ ID NO: 9), R15 (SEQ ID NO: 12) and R18 (SEQ ID NO: 13) were effective when added to neuronal cultures during the 5 minute glutamic acid insult only (FIG. 28), or removed from cultures prior to the insult following a 10 minute pre-exposure (FIG. 29).

Figure 30:
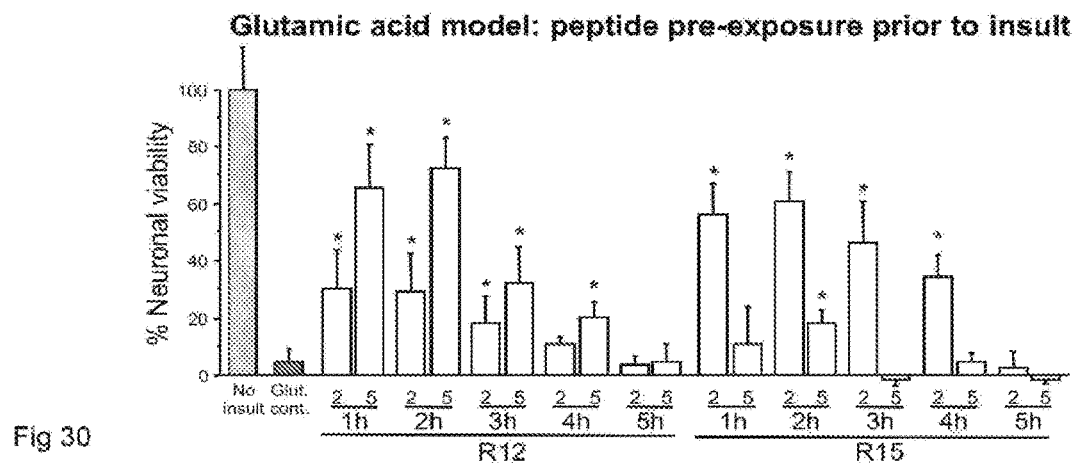
FIG. 30 shows neuroprotective efficacy of R12 (SEQ ID NO: 9) and R15 (SEQ ID NO: 12) in the glutamate model when peptides present in neuronal cultures for 10 min only at 1 to 5 h before glutamic acid exposure. Neuronal viability measured 20-24 h following glutamic acid. Concentration of peptide in µM. MTS data were expressed as percentage neuronal viability with no insult control taken as 100% viability (mean±SD; n=4; *P<0.05).

Peptides R12 (SEQ ID NO: 9) and R15 (SEQ ID NO: 12) were effective when added to neuronal cultures for 10 minutes, 1 to 4 hours prior to the glutamic acid insult (FIG. 30).

Figure 33:
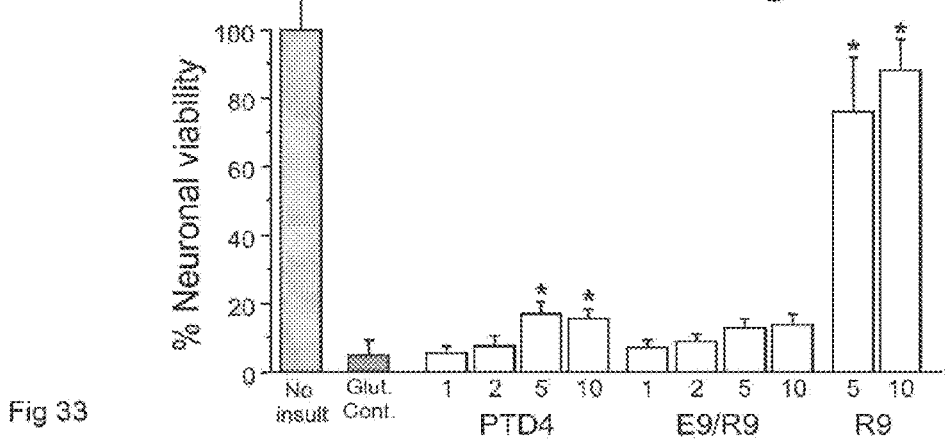
FIG. 33 shows neuroprotective efficacy of PTD-4 (SEQ ID NO: 14), E9/R9 (SEQ ID NO: 15) and R9 (SEQ ID NO: 6) in the glutamate excitotoxicity model when peptides present in neuronal cultures for 15 min before and during 5-min glutamic acid exposure. Neuronal viability measured 20-24 hours following glutamic acid. Concentration of peptide in μM. MTS data were expressed as percentage neuronal viability with no insult control taken as 100% viability (mean±SD; n=4; *P<0.05).
Figure 34:
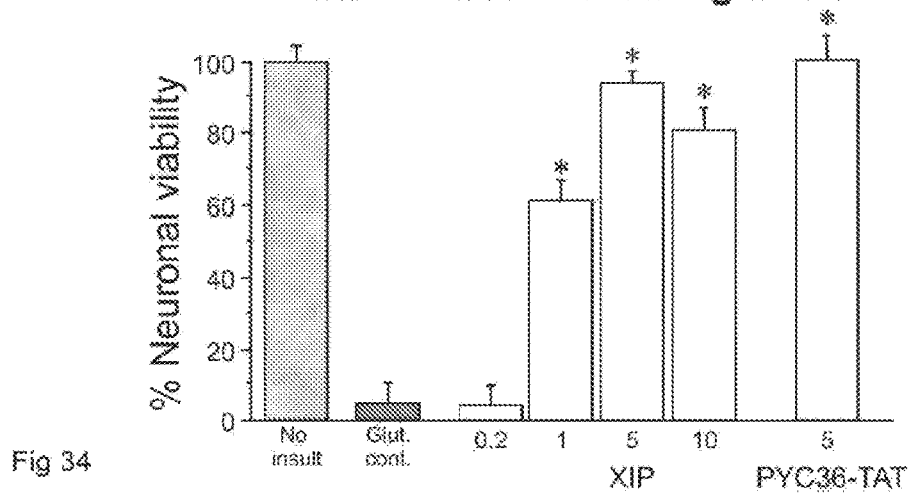
FIG. 34 shows neuroprotective efficacy of XIP (SEQ ID NO: 29) and PYC36-TAT (SEQ ID NO: 24) in the glutamate excitotoxicity model when peptides present in neuronal cultures for 15 min before and during 5-min glutamic acid exposure. Neuronal viability measured 20-24 hours following glutamic acid. Concentration of peptide in μM. MTS data were expressed as percentage neuronal viability with no insult control taken as 100% viability (mean±SD; n=4; *P<0.05).
Figure 35:
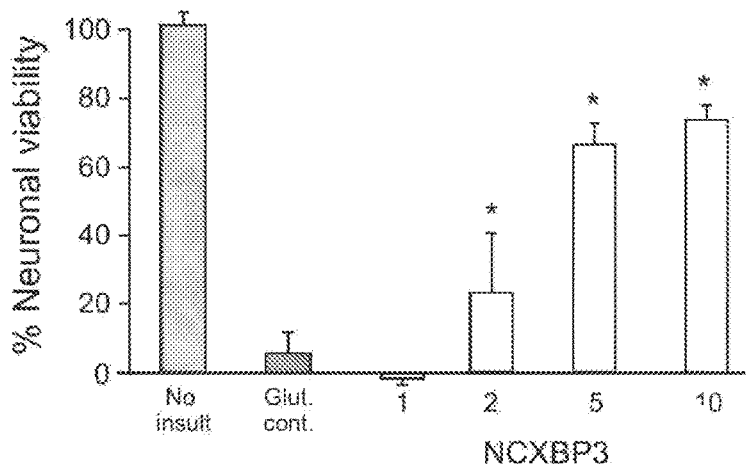
FIG. 35 shows neuroprotective efficacy of NCXBP3 (SEQ ID NO: 30) in the glutamate excitotoxicity model when peptide present in neuronal cultures for 15 min before and during 5-min glutamic acid exposure. Neuronal viability measured 20-24 hours following glutamic acid. Concentration of peptide in μM. MTS data were expressed as percentage neuronal viability with no insult control taken as 100% viability (mean±SD; n=4; *P<0.05).
Figure 36:
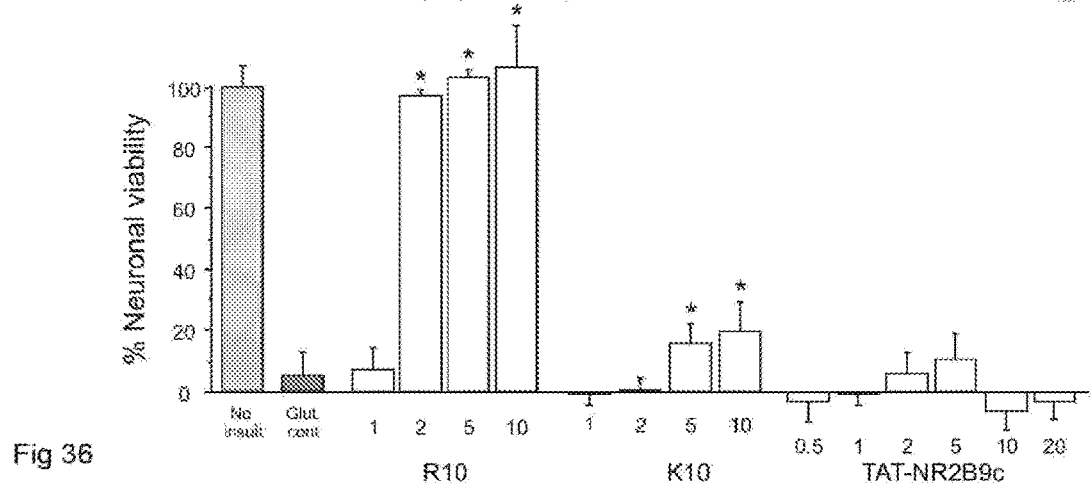
FIG. 36 shows neuroprotective efficacy of K10 (SEQ ID NO: 42), R10 (SEQ ID NO: 7) and TAT-NR2B9c (SEQ ID NO: 18) in the glutamate excitotoxicity model when peptides present in neuronal cultures for 15 min before and during 5-min glutamic acid exposure. Neuronal viability measured 20-24 hours following glutamic acid. Concentration of peptide in μM. MTS data were expressed as percentage neuronal viability with no insult control taken as 100% viability (mean±SD; n=4; *P<0.05).
Figure 37:
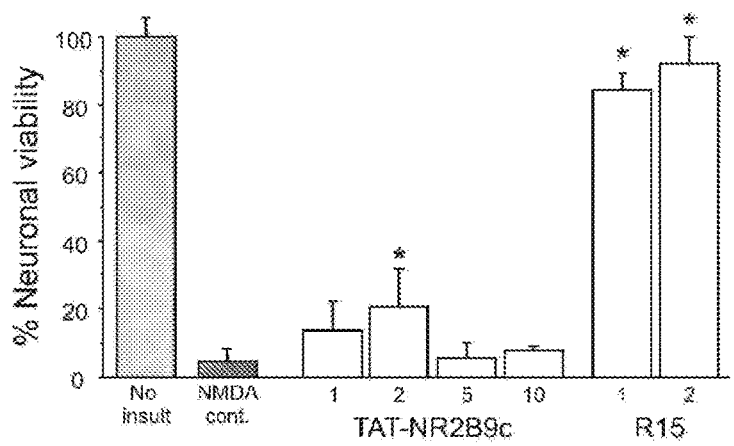
FIG. 37 shows neuroprotective efficacy of R15 (SEQ ID NO: 12) and TAT-NR2B9c (SEQ ID NO: 18) in the NMDA excitotoxicity model when peptides present in neuronal cultures for 15 min before and during 5-min NMDA exposure. Neuronal viability measured 20-24 hours following glutamic acid. Concentration of peptide in μM. MTS data were expressed as percentage neuronal viability with no insult control taken as 100% viability (mean±SD; n=4; *P<0.05).
Figure 38:
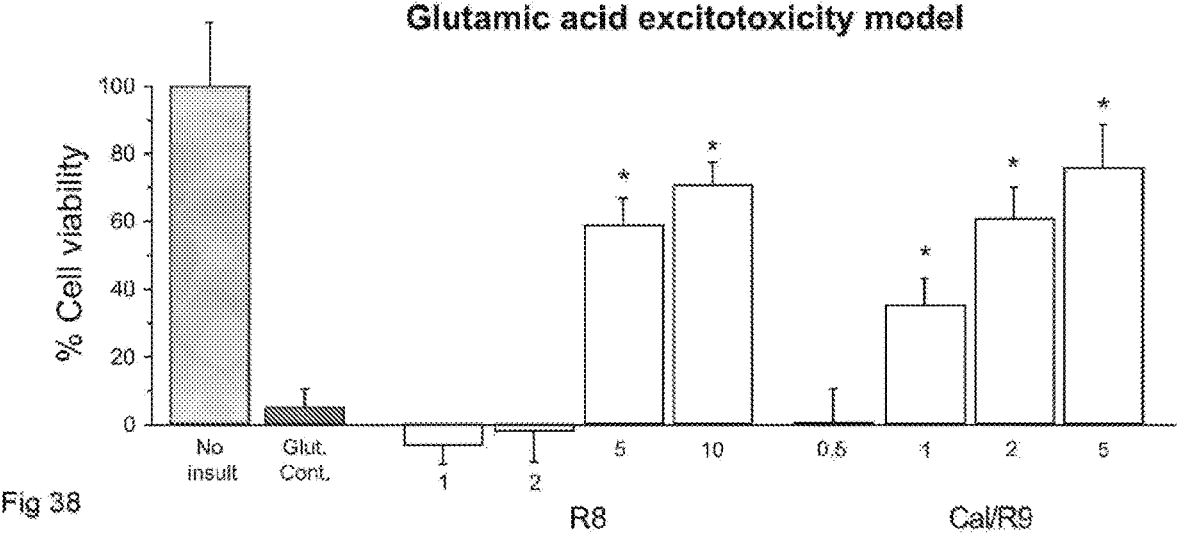
FIG. 38 shows neuroprotective efficacy of R8 (SEQ ID NO: 5) and Cal/R9 (SEQ ID NO: 31) in the glutamate excitotoxicity model when peptides present in neuronal cultures for 15 min before and during 5-min glutamic acid exposure. Neuronal viability measured 20-24 hours following glutamic acid. Concentration of peptide in μM. MTS data were expressed as percentage neuronal viability with no insult control taken as 100% viability (mean±SD; n=4; *P<0.05).
Figure 39:
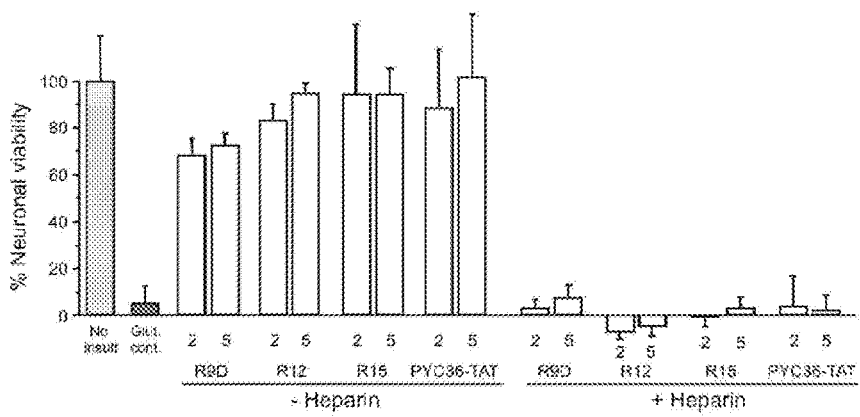
FIG. 39 shows neuroprotective efficacy of D-R9 (SEQ ID NO: 19), R12 (SEQ ID NO: 9), R15 (SEQ ID NO: 12) and PYC36-TAT (SEQ ID NO: 24) peptides incubated with ±heparin (20 IU/ml) for 5 min at room temperature before for being added to neuronal cultures for 10 min only prior to glutamic acid exposure. Neuronal viability measured 20-24 hours following glutamic acid. Concentration of peptide in μM. MTS data were expressed as percentage neuronal viability with no insult control taken as 100% viability (mean±SD; n=4; *P<0.05).
Figure 40:
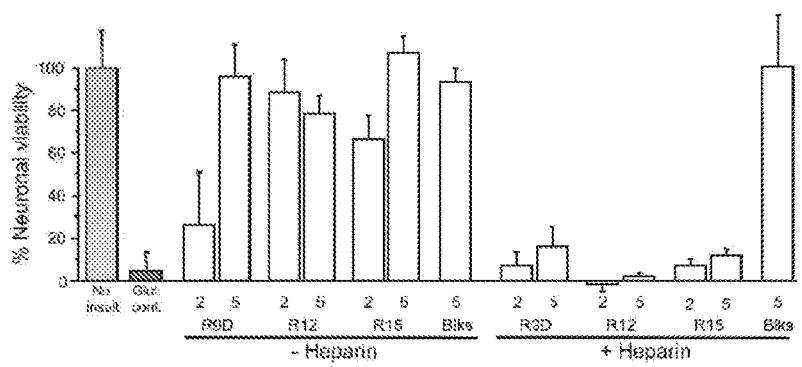
FIG. 40 shows neuroprotective efficacy D-R9 (SEQ ID NO: 19), R12 (SEQ ID NO: 9), and R15 (SEQ ID NO: 12) and glutamate receptor blockers (Blks: 5 μM MK801/5 μM CNQX) when neuronal cultures incubated±heparin (40 IU/ml) for 5 min at 37° C. before addition of peptides for 10 min only at 37° C., and then removed prior to glutamic acid exposure. Neuronal viability measured 20-24 hours following glutamic acid. Concentration of peptide in μM. MTS data were expressed as percentage neuronal viability with no insult control taken as 100% viability (mean±SD; n=4; *P<0.05).
Figure 41:
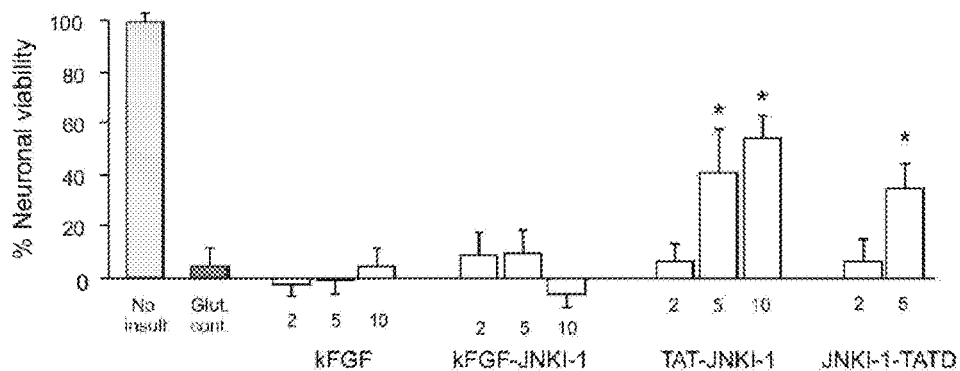
FIG. 41 shows neuroprotective efficacy of kFGF (SEQ ID NO: 28), kFGF-JNKI-1 (SEQ ID NO: 27), TAT-JNKI-1 (SEQ ID NO: 26) and JNKI-1TATD (SEQ ID NO: 25) in the glutamate excitotoxicity model when peptides present in neuronal cultures for 15 min before and during 5-min glutamic acid exposure. Neuronal viability measured 20-24 hours following glutamic acid. Concentration of peptide in μM. MTS data were expressed as percentage neuronal viability with no insult control taken as 100% viability (mean±SD; n=4; *P<0.05).
Figure 44:
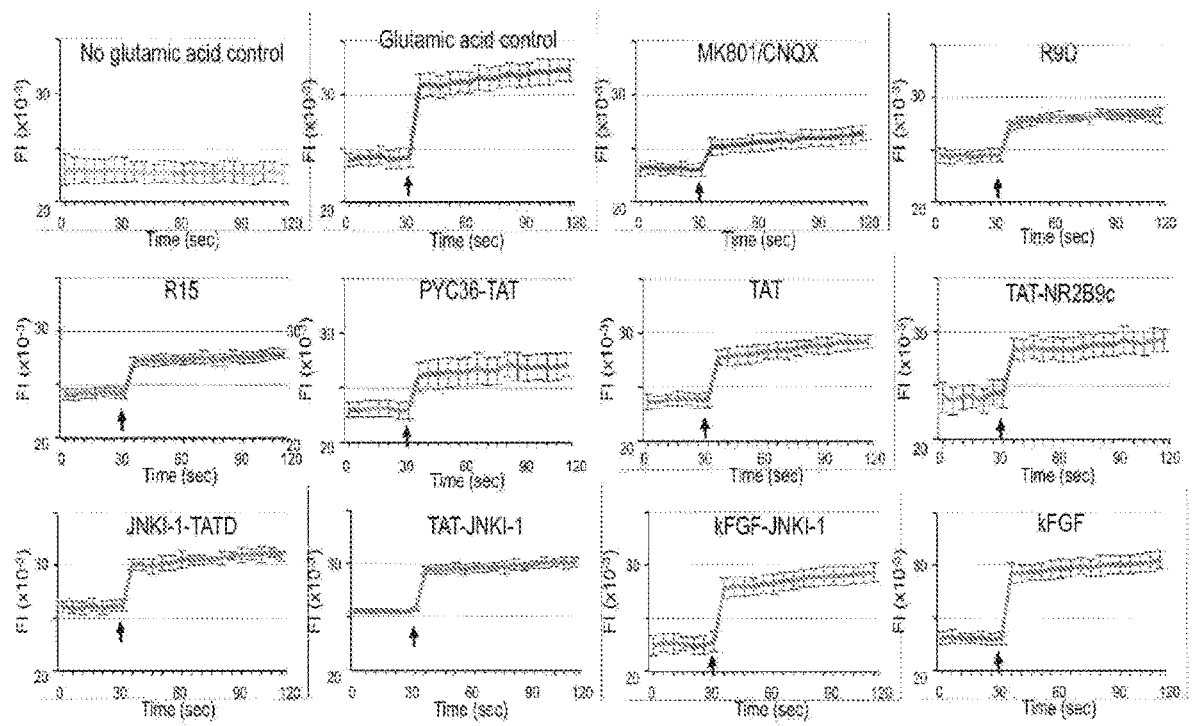
FIG. 44 shows intracellular calcium influx kinetics for glutamate receptor blockers (MK801/CNQX at 5 μM/5 μM), D-R9 (SEQ ID NO: 19), R15 (SEQ ID NO: 12), PYC36-TAT (SEQ ID NO: 24), TAT (SEQ ID NO: 21), TAT-NR2B9c (SEQ ID NO: 18), JNKI-1-TATD (SEQ ID NO: 25), TAT-JNKI-1 (SEQ ID NO: 26), kFGF-JNKI-1 (SEQ ID NO: 27) and kFGF (SEQ ID NO: 28) following glutamic acid exposure in neuronal cultures. Fura-2 AM was used for intracellular calcium assessment. Representative fluorescent Fura-2 AM tracers; fluorescence intensity (FI) of neuronal cultures 30 sec before and following addition (arrow) of glutamic acid (100 μM final concentration). Peptides or glutamate receptor blockers were added to neuronal cultures for 10 min and removed (time=0) before glutamic acid. Values are mean±SE; n=3. Peptide concentration was 5 μM.

Peptides PTD-4 (SEQ ID NO: 14) shows low level neuroprotection, and peptide E9/R9 (SEQ ID NO: 15) shows no protection in the glutamic acid model (FIG. 33), while arginine-rich peptides XIP (SEQ ID NO: 29) and NCXBP3 (SEQ ID NO: 30) show high levels of protection (FIG. 34, 35). Poly-lysine-10 peptide (K10; SEQ ID NO: 42) and TAT-NR2B9c (SEQ ID NO: 18) peptides show low level neuroprotection in glutamic acid (FIG. 36) and NMDA models (FIG. 37), respectively. R8 (SEQ ID NO: 5) and R9 (SEQ ID NO: 6) fused to calpain cleavage site (Cal/R9; SEQ ID NO: 31) show moderate to high level neuroprotection in glutamic acid (FIG. 38). FIGS. 39 and 40 show that the negatively charged molecule heparin blocks neuroprotective actions of D-R9 (SEQ ID NO: 19), R12 (SEQ ID NO: 9), R15 (SEQ ID NO: 12), and PYC36-TAT (SEQ ID NO: 24), but not glutamate receptors blockers (5 µM K801/5 µM CNQX) in the glutamic acid model. FIG. 41 shows that the JNKI-1 peptide (SEQ ID NO: 27) when fused to the (non-arginine) kFGF CPP (SEQ ID NO: 28), which does not rely on endocytosis for uptake, was not neuroprotective in the glutamic acid model; the kFGF (SEQ ID NO: 28) peptide was also ineffective. In contrast, TAT-JNKI-1 (SEQ ID NO: 26) and JNKI-1-TATD (SEQ ID NO: 25) were neuroprotective. FIG. 44 shows that peptides D-R9 (SEQ ID NO: 19), R12 (SEQ ID NO: 9), R15 (SEQ ID NO: 12), and PYC36-TAT (SEQ ID NO: 24), TAT (SEQ ID NO: 21), TAT-NR2B9c (SEQ ID NO: 18), TAT-JNKI-1 (SEQ ID NO: 26) and JNKI-1-TATD (SEQ ID NO: 25) and glutamate receptors blockers (5 µM K801/5 µM CNQX) to varying degrees reduced calcium influx in neuronal cultures after treatment with glutamic acid.

Experimental Example 2

Neuroprotection Following Kainic Acid Exposure

Following kainic acid exposure TAT-D (SEQ ID NO: 20), R9 (SEQ ID NO: 6) and penetratin (SEQ ID NO: 22) were neuroprotective, but less effective than in the glutamic acid model, and did not always display a typical dose response pattern (FIG. 2, Table 2). Pep-1 (SEQ ID NO: 23) was ineffective. R9 (SEQ ID NO: 6) was the most potent peptide, increasing neuronal survival from ≈20% to a maximum of ≈80%. The respective IC50 values for R9 (SEQ ID NO: 6), penetratin (SEQ ID NO: 22), and TAT-D (SEQ ID NO: 20) were 0.81, 2.0 and 6.2 µM. The glutamate receptors blockers, JNKI-1 D-TAT (SEQ ID NO: 25) and PYC36L-TAT (SEQ ID NO: 24) were also effective in this model (FIG. 2).

Experimental Example 3

Neuroprotection Following In Vitro Ischemia/Oxygen Glucose Deprivation (OGD)

Following in vitro ischemia all four CPPs displayed neuroprotective effects (FIG. 3, Table 2). Neuroprotection with Arg-9 (SEQ ID NO: 6) (IC50: 6.0 µM) and TAT-D (SEQ ID NO: 20) (IC50: 7.1 µM) was similar; efficacy followed a dose response pattern and increased neuronal survival from ≈10% to 40-50%. Neuroprotective efficacy was lost with increasing concentrations of penetratin (SEQ ID NO: 22) (≥5 µM), while Pep-1 (SEQ ID NO: 23) was only neuroprotective at lower concentrations (1-5 µM). Glutamate receptors blockers and PYC36L-TAT (SEQ ID NO: 24) were also effective in this model (FIG. 3a).

In addition, when added post-in vitro ischemia R9 (SEQ ID NO: 6), R12 (SEQ ID NO: 9), R15 (SEQ ID NO: 12) and R18 (SEQ ID NO: 13) displayed neuroprotective effects, however higher concentrations of R15 (SEQ ID NO: 12) and R18 (SEQ ID NO: 13) reduced efficacy (FIG. 3b).

Figure 3C:
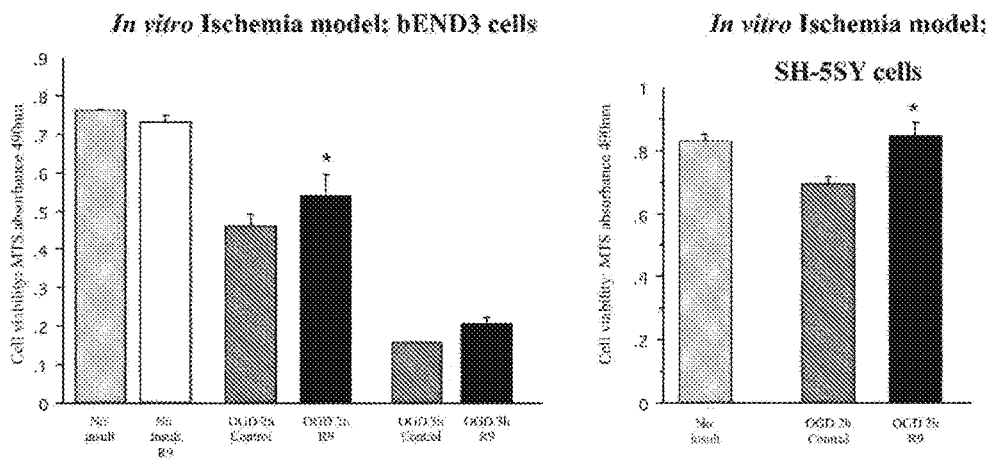
FIG. 3c shows further results of an in vitro ischemia model. R9 (SEQ ID NO: 6) peptide present during in vitro ischemia and at 50% dose after ischemia: Peptide dose for bEND3 cells was 10 μM during/5 μM post-in vitro ischemia. Peptide dose for SH-5YSY cells was 5 μM during/2.5 μM post-in vitro ischemia. Cell viability 24 hours following in vitro ischemia (MTS data mean±SEM; n=4; *P<0.05).
Figure 4:
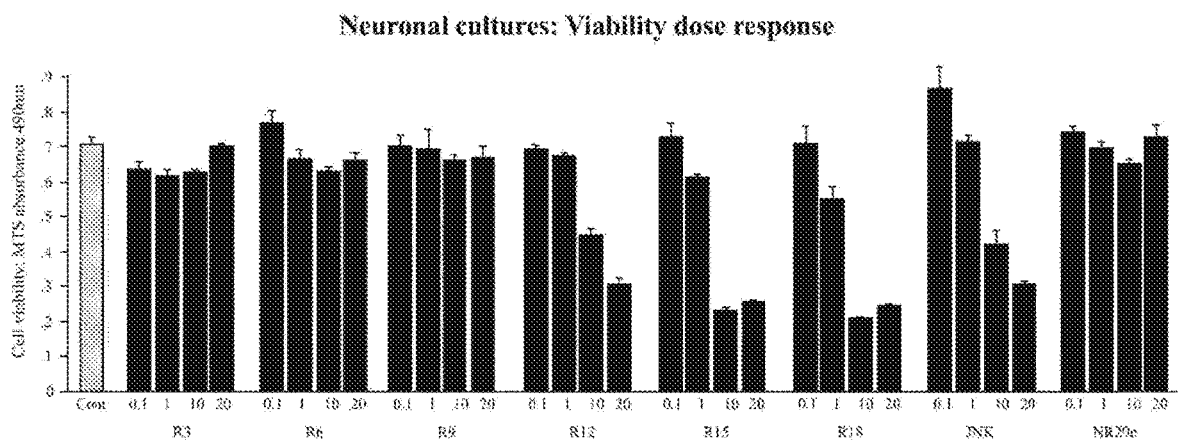
FIG. 4 shows neuronal viability following exposure of cultures to different peptide concentrations. Peptide concentration shown in μM. Neuronal viability 24 hours following exposure with R3 (SEQ ID NO: 2), R6 (SEQ ID NO: 3), R9 (SEQ ID NO: 6), R12 (SEQ ID NO: 9), R15 (SEQ ID NO: 12), R18 (SEQ ID NO: 13), JNK (JNKI-1D-TAT; SEQ ID NO: 25) and NR2B9c (SEQ ID NO: 18) peptides. Cell viability data expressed as MTS absorbance at 490 nm (mean±SEM; n=4).
Figure 42:
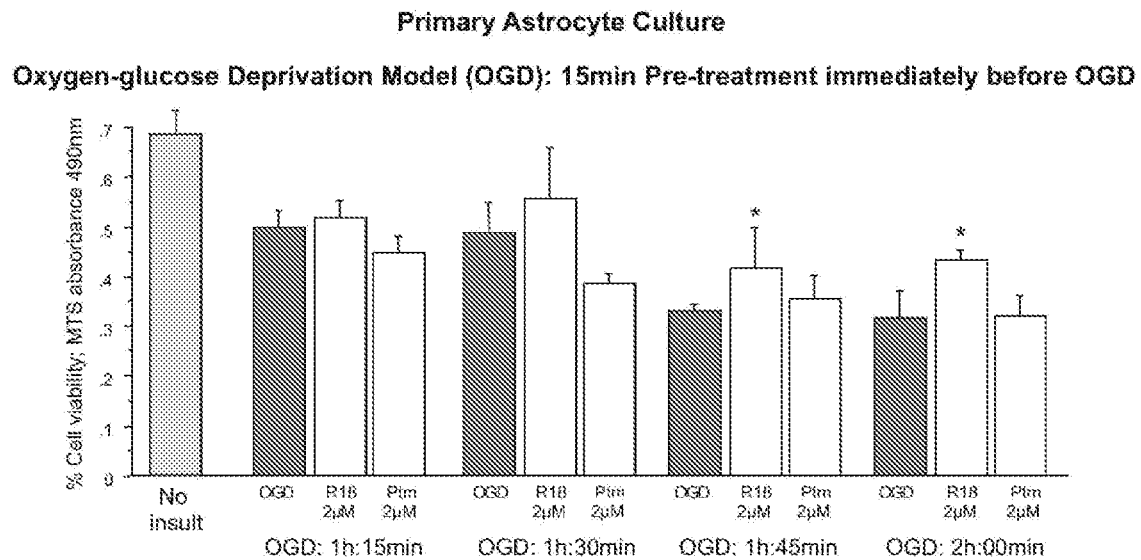
FIG. 42 shows the results of pre-exposure of protamine sulphate (Ptm1-4 mixture; SEQ ID NOs: 32 to 35) and R18 (SEQ ID NO: 13) peptides to primary rat astrocytes for 15 min prior to oxygen-glucose deprivation. Concentration of peptides 2 μM. Cell viability assessed 24 hours after OGD using MTS assay. MTS data were expressed as absorbance values at 490 mm (mean±SD; n=4-6; *P<0.05).

R9 (SEQ ID NO: 6) also reduced bEND3 and SH-5YSY cell death when exposed to in vitro ischemia (FIG. 3c). R18 (SEQ ID NO: 13) also reduced astrocyte cell death when exposed to in vitro ischemia (FIG. 42).

Figure 6:
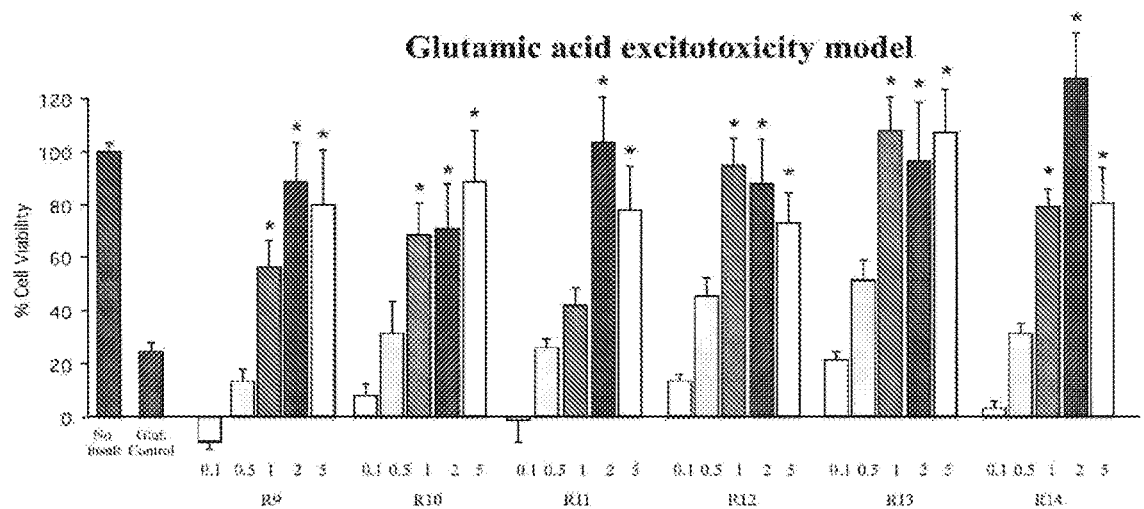
FIG. 6 shows a dose response study using R9 (SEQ ID NO: 6), R10 (SEQ ID NO: 7), R11 (SEQ ID NO: 8), R12 (SEQ ID NO: 9), R13 (SEQ ID NO: 10) and R14 (SEQ ID NO: 11) in the glutamate model. Mean±SEM: N=4; *P<0.05. (Peptide concentration in μM).

FIG. 6 shows a dose response study using R9 (SEQ ID NO: 6), R10 (SEQ ID NO: 7), R11 (SEQ ID NO: 8), R12 (SEQ ID NO: 9), R13 (SEQ ID NO: 10) and R14 (SEQ ID NO: 11) in the glutamate model, which revealed that all peptides displayed significant neuroprotection between 1 and 5 µM, except for R11 (SEQ ID NO: 8) which displayed significant neuroprotection at 2 and 5 µM. Mean±SEM: N=4; *P<0.05. (Peptide concentration in µM).

Figure 7:
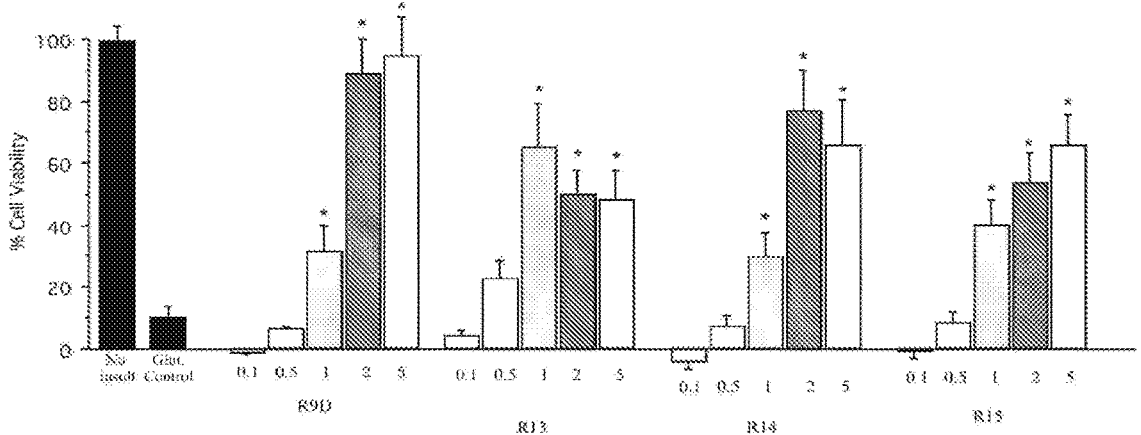
FIG. 7 shows a dose response study using D-R9 (SEQ ID NO: 19), R13 (SEQ ID NO: 10), R14 (SEQ ID NO: 11) and R15 (SEQ ID NO: 12) in the glutamate model. Mean±SEM: N=4; *P<0.05. (Peptide concentration in μM).

FIG. 7 shows a dose response study using D-R9 (SEQ ID NO: 19), R13 (SEQ ID NO: 10), R14 (SEQ ID NO: 11) and R15 (SEQ ID NO: 12) in the glutamate model, which revealed that all peptides displayed neuroprotection between 1 and 5 µM. Mean±SEM: N=4; *P<0.05. (Peptide concentration in µM).

Figure 8:
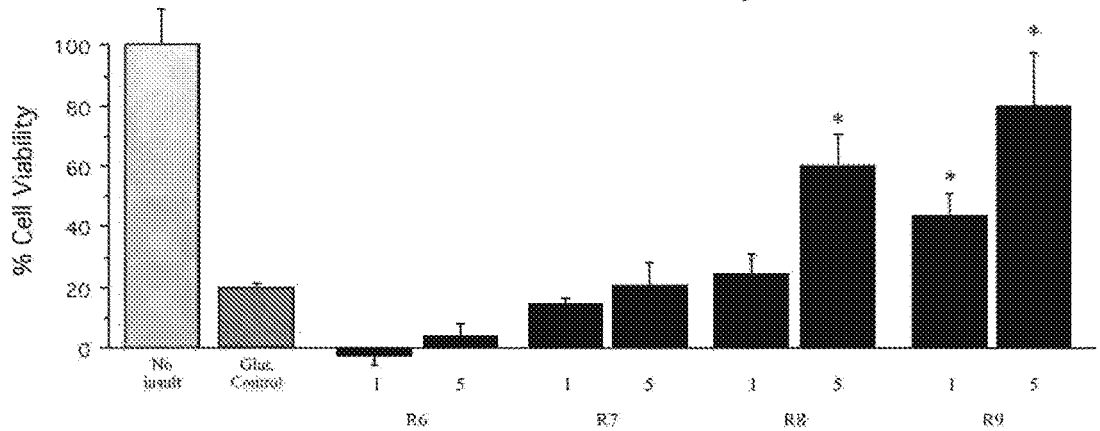
FIG. 8 shows a dose response study using R6 (SEQ ID NO: 3), R7 (SEQ ID NO: 4), R8 (SEQ ID NO: 5), and R9 (SEQ ID NO: 6) in the glutamate model. Mean±SEM: N=4; *P<0.05. (Peptide concentration in μM).
Figure 9:
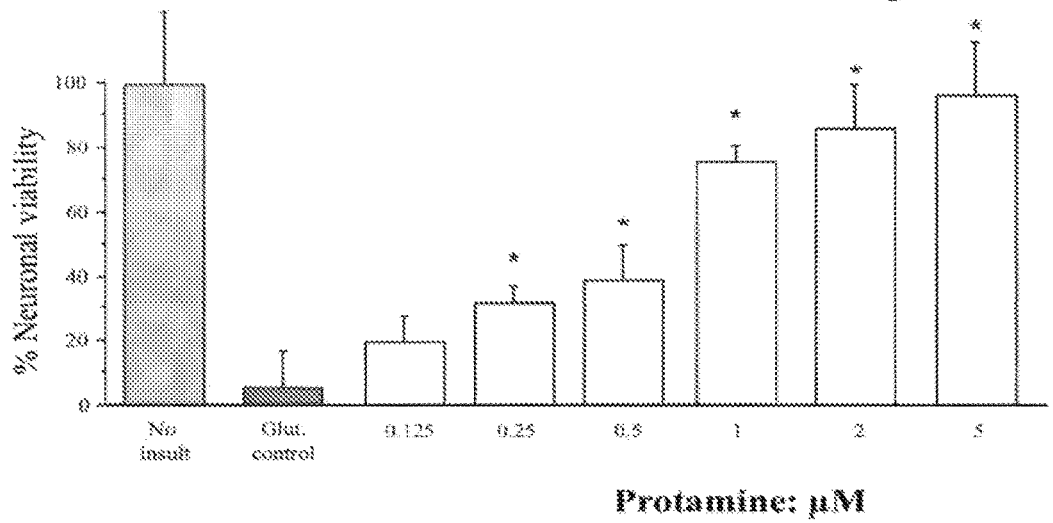
FIG. 9 shows the results of the glutamic acid excitotoxicity model; concentration of protamine (Ptm1-4 mixture; SEQ ID NOs: 32 to 35) in μM. Treatment of neuronal cultures with protamine (Ptm1-4 mixture; SEQ ID NOs: 32 to 35) was for 15 minutes prior to glutamic acid exposure (100 μM), which was for 5 minutes at 37° C. Neuronal viability 24 hours following glutamic acid exposure and treatment with different protamine (Ptm1-4 mixture; SEQ ID NOs: 32 to 35) concentrations or no treatment (Glut control). MTS data were expressed as percentage neuronal viability with no insult control taken as 100% viability (mean+SD; n=4-6; *P<0.05).
Figure 10:
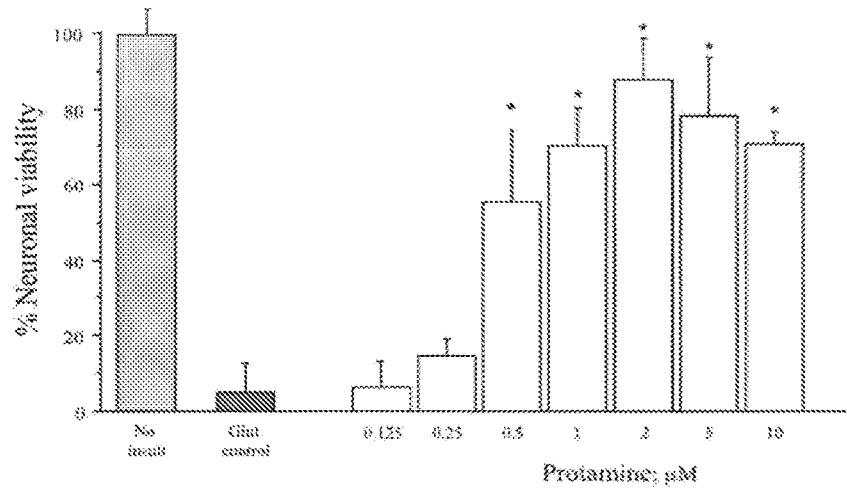
FIG. 10 shows the results of the glutamic acid excitotoxicity model; concentration of protamine (Ptm1-4 mixture; SEQ ID NOs: 32 to 35) in μM. Treatment of neuronal cultures with protamine (Ptm1-4 mixture; SEQ ID NOs: 32 to 35) was for 15 minutes prior to and during glutamic acid exposure (100 μM), which was for 5 minutes at 37° C. Neuronal viability 24 hours following glutamic acid exposure and treatment with different protamine (Ptm1-4 mixture; SEQ ID NOs: 32 to 35) concentrations or no treatment (Glut control). MTS data were expressed as percentage neuronal viability with no insult control taken as 100% viability (mean±SD; n=4-6; *P<0.05).
Figure 31:
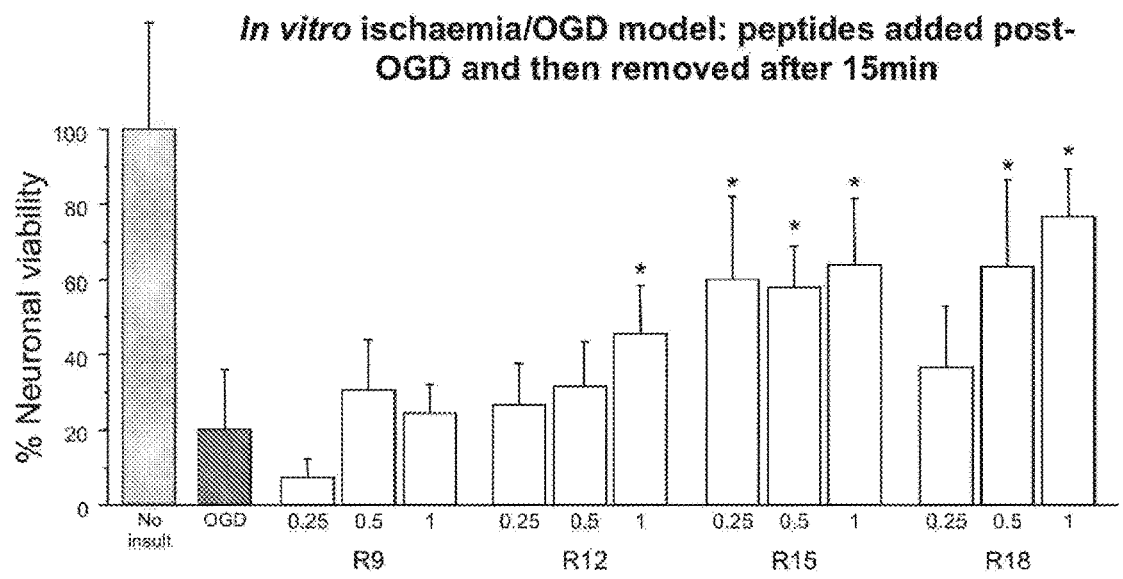
FIG. 31 shows neuroprotective efficacy of R9 (SEQ ID NO: 6), R12 (SEQ ID NO: 9), R15 (SEQ ID NO: 12) and R18 (SEQ ID NO: 13) in the oxygen-glucose deprivation (OGD) model when peptides added to neuronal cultures immediately after OGD and removed after 15 min. Neuronal viability measured 20-24 hours following OGD. Concentration of peptide in μM. MTS data were expressed as percentage neuronal viability with no insult control taken as 100% viability (mean±SD; n=4-6; *P<0.05).

As shown in FIG. 8, in a dose response study using R6 (SEQ ID NO: 3), R7 (SEQ ID NO: 4), R8 (SEQ ID NO: 5), and R9 (SEQ ID NO: 6) in the glutamate model, it was revealed that peptides R8 (SEQ ID NO: 5) and R9 (SEQ ID NO: 6) displayed significant neuroprotection at 5 µM and 1 µM and 5 µM concentrations, respectively, while R6 (SEQ ID NO: 3) and R7 (SEQ ID NO: 4) did not exhibit significant neuroprotection. Mean±SEM: N=4; *P<0.05. (Peptide concentration in µM). FIG. 31 shows a dose response study using R9 (SEQ ID NO: 6), R12 (SEQ ID NO: 9), RR9 (SEQ ID NO: 12) and R18 (SEQ ID NO: 13) when peptides were added for 15 minutes after 000. Neuroprotection is displayed for R12 (SEQ ID NO: 9), R15 (SEQ ID NO: 12) and R18 (SEQ ID NO: 13), but not R9 (SEQ ID NO: 6) at 1 µM and 5 µM.

Figure 32:
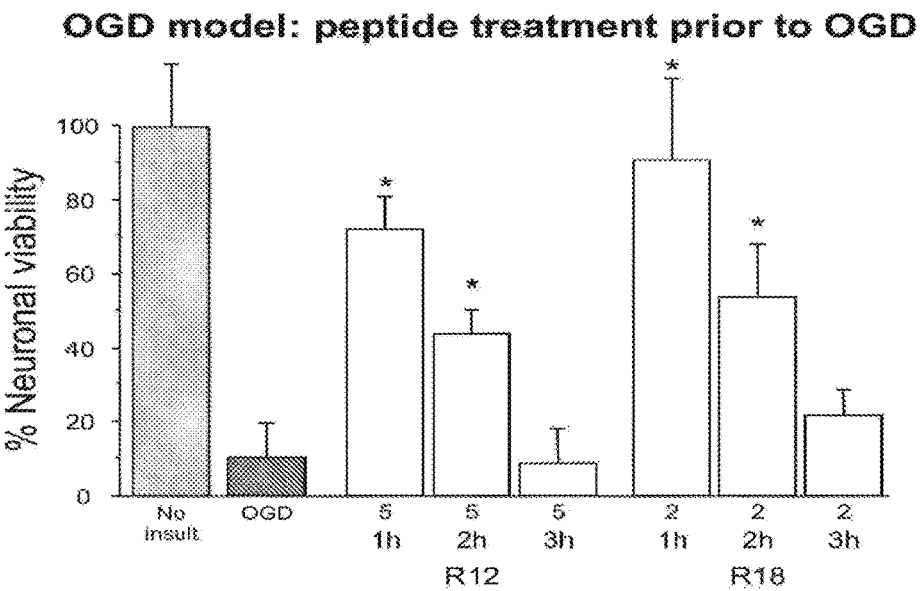
FIG. 32 shows neuroprotective efficacy of R9 (SEQ ID NO: 6), R12 (SEQ ID NO: 9), R15 (SEQ ID NO: 12) and R18 (SEQ ID NO: 13) in the oxygen-glucose deprivation when peptides present in neuronal cultures only for 10 min at 1 to 3 h before OGD. Neuronal viability measured 20-24 hours following OGD. Concentration of peptide in μM. MTS data were expressed as percentage neuronal viability with no insult control taken as 100% viability (mean±SD; n=4-6; *P<0.05).

Peptides R12 (SEQ ID NO: 9) and R18 (SEQ ID NO: 13) were effective when added to neuronal cultures for 10 minutes, 1 to 3 hours prior to OGD (FIG. 32).

TABLE 3

IC50 values of cell penetrating and control peptides for the three injury models

| Peptide | SEQ ID NO. | IC50: Glutamic acid model (µM) | IC50: Kainic acid model (µM) | IC50: In vitro ischemia model (µM) |
|---|---|---|---|---|
| Arg-9 (R9) | 6 | 0.78 | 0.81 | 6.0 |
| TAT-D | 20 | 13.9 | 8.2 | 7.1 |
| Penetratin | 22 | 3.4 | 2.0 | N/A |
| Pep-1 | 23 | N/A | N/A | >15 |
| PYC36L-TAT# | 24 | 1.5 | — | — |
| JNKI-1D-TAT# | 25 | 2.1 | 6.5 | — |

* Based on dose response graphs shown in FIG. 1a, FIG. 2 and FIG. 3a.
IC50 values for JNKI-1D-TAT and PYC36L-TAT peptides from Meade et al. (2010a, b).
N/A = not applicable because peptides were either ineffective or increased cell death at higher doses.
— = data not available.

TABLE 4

IC50 values of polyarginine peptides for glutamic acid models*

| Peptide | SEQ ID NO. | IC50: Glutamic acid model (µM) | 95% confidence intervals (µM) |
|---|---|---|---|
| Arg-1 (R1) | 1 | >5 µM | N/A |
| Arg-3 (R3) | 2 | >5 µM | N/A |
| Arg-6 (R6) | 3 | >5 µM | N/A |
| Arg-9 (R9) | 6 | 0.83 | 0.16-4.1 |
| Arg-12 (R12) | 9 | 0.44 | 0.16-1.2 |
| Arg-15 (R15) | 12 | 0.19 | 0.06-0.6 |
| Arg-18 (R18) | 13 | 0.24 | 0.08-0.75 |
| R9/tPA/R9 | 16 | 0.29 | 0.06-1.4 |

*Based on dose response graph shown in FIG. 1e.
N/A = not applicable because peptides had no or little effect at highest concentration tested (5 µM).

Experimental Example 4

Animal Trial

Figure 5:
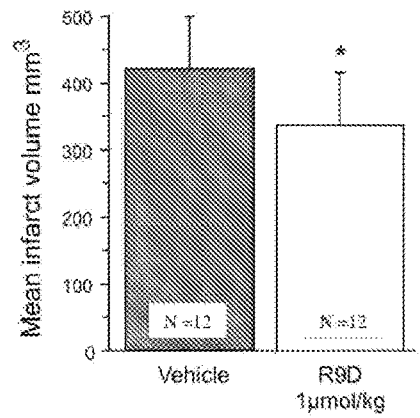
FIG. 5 shows the results of the initial animal model pilot trial, which shows the efficacy of D-R9 (SEQ ID NO: 19) peptide in rat permanent middle cerebral artery occlusion (MCAO) stroke model. D-R9 (SEQ ID NO: 19) peptide was administered intravenously 30 min post-MCAO. Infarct volume (brain injury) was measured 24 h post-MCAO (mean±SD).
Figure 27:
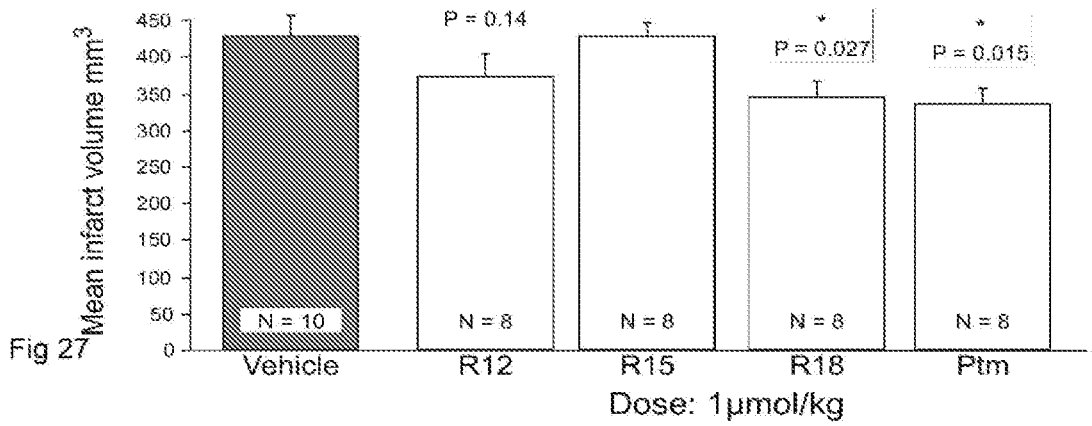
FIG. 27 shows neuroprotective effects of the R12 (SEQ ID NO: 9), R15 (SEQ ID NO: 12), R18 (SEQ ID NO: 13) and protamine (Ptm1-4 mixture; SEQ ID NOs: 32 to 35) peptides in permanent middle cerebral artery occlusion (MCAO) stroke model when administered intravenously 30 min after occlusion. Peptide dose was 1 µmol/kg (600 µl: IV) and infarct assessment was at 24 h after MCAO (mean±SE; n=8-10; *P<0.05). Animal treatments were randomized and all procedures were performed blinded to treatment.

In an initial animal trial that was conducted, it was shown that Arg-9 (R9; SEQ ID NO: 6), R18 (SEQ ID NO: 13) and protamine (Ptm) (Ptm1-4 mixture SEQ ID NOs: 32 to 35) possessed neuroprotective activity in vivo. These trials showed the efficacy of D-R9 (SEQ ID NO: 19) peptide in rat permanent middle cerebral artery occlusion (MCAO) stroke model. D-R9 (SEQ ID NO: 19) peptide was administered intravenously 30 min post-MCAO. Infarct volume (brain injury) was measured 24 h post-MCAO (mean±SEM). This is shown in FIGS. 5 and 27 where it can be seen that (Ns=8-12 animals for each group) treatment with D-R9 (SEQ ID NO: 19), R18 (SEQ ID NO: 13) and protamine (Ptm) (Ptm1-4 mixture SEQ ID NOs: 32 to 35) showed a statistically significant neuroprotective effect by reducing infarct volume (brain damage) by approximately 20% after a MCAO stroke.

General Observations and Discussion

The Applicant assessed TAT (SEQ ID NO: 21) as known neuroprotective example and three other CPPs (penetratin; SEQ ID NO: 22, R9; SEQ ID NO: 6, and Pep-1; SEQ ID NO: 23) for their neuroprotective properties in cortical neuronal cultures following exposure to glutamic acid, kainic acid, or in vitro ischemia (oxygen-glucose deprivation).

In addition, poly-arginine peptides (R9; SEQ ID NO: 6, R12; SEQ ID NO: 9, R15; SEQ ID NO: 12, R18; SEQ ID NO: 13) and/or arginine-rich protamine peptide (SEQ ID NOs: 32 to 36) were also assessed in astrocyte, brain endothelial cell line (bEND3), and/or a neuroblastoma cell line (SH-SY5Y) cultures using the in vitro ischemia model.

R9 (SEQ ID NO: 6), penetratin (SEQ ID NO: 22) and TAT-D (SEQ ID NO: 20) displayed consistent and high level neuroprotective activity in both the glutamic acid (IC50: 0.78, 3.4, 13.9 µM) and kainic acid (IC50: 0.81, 2.0, 6.2 µM) injury models, while Pep-1 (SEQ ID NO: 23) was ineffective.

The TAT-D (SEQ ID NO: 20) isoform displayed similar efficacy to the TAT-L (SEQ ID NO: 21) isoform in the glutamic acid model. R9 (SEQ ID NO: 6) displayed efficacy when washed-out prior to glutamic acid exposure. However, R9 (SEQ ID NO: 6) was significantly more effective than peptides that had previously been shown to be neuroprotective, i.e. TAT-D (SEQ ID NO: 20), TAT-L (SEQ ID NO: 21), PYC36L-TAT (SEQ ID NO: 24), and JNKI-1 D-TAT (SEQ ID NO: 25).

Neuroprotection following in vitro ischemia was more variable, with all peptides providing some level of neuroprotection [(IC50; R9 (SEQ ID NO: 6): 6.0 µM, TAT-D (SEQ ID NO: 20): 7.1 µM, penetratin (SEQ ID NO: 22)/Pep-1 (SEQ ID NO: 23): >10 µM)]. The positive control peptides JNKI-1 D-TAT (SEQ ID NO: 25) (JNK inhibitory peptide) and/or PYC36L-TAT (SEQ ID NO: 24) (AP-1 inhibitory peptide) were neuroprotective in all models.

In a post-glutamic acid treatment experiment, R9 (SEQ ID NO: 6) was highly effective when added immediately after, and mildly effective when added 15 minutes post-insult, while the JNKI-1 D-TAT (SEQ ID NO: 25) control peptide was ineffective when added post-insult.

In an initial animal trial that was conducted, it was shown that R9 (SEQ ID NO: 6), R12 (SEQ ID NO: 9), R18 (SEQ ID NO: 13), and protamine (Ptm1-4 mixture SEQ ID NOs: 32 to 35) possessed neuroprotective activity in vivo.

In a dose response study using R1 (SEQ ID NO: 1), R3 (SEQ ID NO: 2), R6 (SEQ ID NO: 3), R9 (SEQ ID NO: 6), R12 (SEQ ID NO: 9), R15 (SEQ ID NO: 12) and R18 (SEQ ID NO: 13) in the glutamate model revealed that: i) R1 (SEQ ID NO: 1), R3 (SEQ ID NO: 2), R6 (SEQ ID NO: 3), and R7 (SEQ ID NO: 4) displayed no to little neuroprotection; ii) the order of potency for the other peptides was R15 (SEQ ID NO: 12) >R18 (SEQ ID NO: 13) >R12 (SEQ ID NO: 9) >R9 (SEQ ID NO: 6); and iii) neuroprotective efficacy for R15 (SEQ ID NO: 12) and R18 (SEQ ID NO: 13) was reduced at the higher concentration tested (5 µM).

In a dose response study using R9 (SEQ ID NO: 6), DAHK (SEQ ID NO: 17) (last four end N-terminal amino acids of protein albumin), PTD-4 (SEQ ID NO: 14) (modified TAT (SEQ ID NO: 21) peptide with X33 increased cell penetrating ability; Ho et al., 2001), R9E9 (SEQ ID NO: 15) (R9/Glu-9; neutral peptide) and R9/tPA/R9 (SEQ ID NO: 16) (tissue plasminogen activator enzyme peptide cleavage site flanked by R9 (SEQ ID NO: 6)) in the glutamate model revealed that: i) PTD-4 (SEQ ID NO: 14) and R9/E9 (SEQ ID NO: 15) displayed no to little neuroprotection; DAHK (SEQ ID NO: 17) had low level neuroprotection; and ii) R9/tPA/R9 (SEQ ID NO: 16) had a potency between R12 (SEQ ID NO: 9) and R18 (SEQ ID NO: 13). Also the TAT-NR2B9c (SEQ ID NO: 18) peptide (C-terminal NR2B NMDRA receptor subunit peptide blocks NMDAR signaling with PSD-95 protein to block NO production; Aarts et al., 2002). Poly-arginine (SEQ ID NOs: 6, 13) and arginine-rich (protamine; Ptm mixture SEQ ID NOs: 32 to 35; Ptm4; SEQ ID NO: 35) peptides could also reduce astrocyte bEND3 and SH-SY5Y cell death following in vitro ischemia.

These findings demonstrate that the peptides of the invention have the ability to inhibit neurodamaging events/pathways associated with excitotoxic and ischemic injuries. Poly-arginine peptides with ≥9 arginine amino acid residues are particularly neuroprotective.

The cytoprotective properties of the peptides of the invention suggests they are ideal carrier molecules to deliver neuroprotective drugs to the CNS following injury and/or to serve as potential neuroprotectants in their own right.

The peptides of the invention thus exhibit neuroprotective properties in different in vitro injury models that have been shown to be translatable into in vivo models. This is further bolstered by the neuroprotective effect shown in the initial animal trials that were conducted. The superior neuroprotective action of R9 (SEQ ID NO: 6) was surprising; based on IC50 values R9 (SEQ ID NO: 6) was 17 and 7 fold more potent than TAT-D (SEQ ID NO: 20) in glutamic acid and kainic acid models respectively, and was the only peptide effective even when washed-out prior to glutamate acid exposure. This finding suggests the increased arginine residues and/or the slightly higher net charge (10 vs 9 at pH 7) of R9 (SEQ ID NO: 6) are important factors for neuroprotection following excitotoxicity. Furthermore, while the exact reason for the loss of efficacy of TAT (SEQ ID NO: 21) and penetratin, but not R9 (SEQ ID NO: 6) following wash-out prior to glutamic acid exposure is unclear, it may relate to the speed of R9 (SEQ ID NO: 6) intracellular up-take, rather than an extracellular mechanism. This is supported by the finding that R9 (SEQ ID NO: 6) was effective when added after glutamic acid exposure, while the JNKI-1 D-TAT (SEQ ID NO: 25) peptide was ineffective.

Furthermore, when arginine and poly-arginine peptide(s) R1 (SEQ ID NO: 1), R3 (SEQ ID NO: 2), R6 (SEQ ID NO: 3), R9 (SEQ ID NO: 6), R12 (SEQ ID NO: 9), R15 (SEQ ID NO: 12) and R18 (SEQ ID NO: 13) were assessed in the glutamic acid injury model only peptides R9 (SEQ ID NO: 6), R12 (SEQ ID NO: 9), R15 (SEQ ID NO: 12) and R18 (SEQ ID NO: 13) showed significant neuroprotection at the doses tested; R15 (SEQ ID NO: 12) appeared to be the most potent peptide. A hybrid R9 (SEQ ID NO: 6) peptide (R9/tPA/R9; (SEQ ID NO: 16) containing the tPA cleavage linker site was also highly effective in the glutamic acid model. R9 (SEQ ID NO: 6) was also more effective than R12 (SEQ ID NO: 9) when added post-glutamic acid exposure. Interestingly, PTD-4 (SEQ ID NO: 14) (modified TAT (SEQ ID NO: 21) peptide with 33× improved transduction efficacy when compared to regular TAT; Ho et al., 2001), the R9/E9 (SEQ ID NO: 15) hybrid and the NR2B9c (SEQ ID NO: 18) (a TAT fused peptide that blocks NMDA/glutamate receptor-induced NO production) and DAHK (SEQ ID NO: 17) (last four end N-terminal amino acids of protein albumin) were largely ineffective following glutamic acid exposure.

Peptides R9 (SEQ ID NO: 6), R12 (SEQ ID NO: 9), R15 (SEQ ID NO: 12) and R18 (SEQ ID NO: 13) were also effective in the in vitro ischemia model when added after anaerobic incubation (i.e. during reperfusion phase of injury). R9 (SEQ ID NO: 6) was also able to protect brain endothelial cells (bEND3 cells) and neuroblastoma cells (SH-5YSY cells) following in vitro ischemia.

As mentioned hereinbefore, a result in the study was the demonstration that penetratin (SEQ ID NO: 22) and Pep-1 (SEQ ID NO: 23) also exhibited neuroprotective properties. The penetratin (SEQ ID NO: 22) and Pep-1 (SEQ ID NO: 23) peptides bear no amino-acid sequence relatedness to each other, or the TAT/R9 (SEQ ID NO: 6) peptides. Interestingly penetratin (SEQ ID NO: 22) was highly neuroprotective in the excitotoxic models (IC50s: 3.4 and 2 μM), but less effective in the in vitro ischemia model, with increasing concentrations reducing efficacy. The Pep-1 (SEQ ID NO: 23) peptide was generally ineffective in the excitotoxic models and in some experiments appeared to increase neuronal death (data not shown), but was neuroprotective following in vitro ischemia at lower concentrations. Interestingly, when penetratin (SEQ ID NO: 22) was washed-out from neuronal cultures prior to glutamic acid exposure, visual observations revealed that the peptide did display some early neuroprotective effects (data not shown). Hence, both penetratin (SEQ ID NO: 22) and Pep-1 (SEQ ID NO: 23) behaved differently to each other and the TAT/R9 (SEQ ID NO: 6) peptides in the injury models.

The differential neuroprotective responses for the four CPPs in the excitotoxic and ischemic injury models is likely to be related to the peptides' physical-chemical properties, and more specifically their endocytic-inducing properties. Furthermore, it is likely that the neuroprotective action of the CPPs is mediated at the cell membrane (e.g. receptors, ion channels). Xu et al. (2008), have suggested that TAT (SEQ ID NO: 20) may alter the cell membrane and thereby affect the function of cell surface receptors, such as the NMDA receptor, resulting in reduced calcium influx.

It is contemplated, however, that the peptide or peptides of the invention can act to block NMDA receptor functioning and/or block, downregulate, or decelerate the influx of calcium. An alternative mechanism is that the CPPs interact and stabilise the outer mitochondrial membrane and thereby help to preserve mitochondrial function. Potential benefits are maintenance of ATP synthesis, reduced reactive oxygen species production, and improved calcium handling. To this end, the Applicant has observed that Arg-9 (SEQ ID NO: 6) can increase MTS absorbance levels above baseline levels in normal neurons and following injury (e.g. FIG. 1A, 15 μM). Since reduction of MTS to its formazan product primarily occurs in mitochondria, the ability of Arg-9 (SEQ ID NO: 6) to increase formazan levels is supportive that the peptide is improving mitochondrial function. Another potential mechanism especially in relation to R9 (SEQ ID NO: 6) and TAT (SEQ ID NO: 21), is that these arginine-rich peptides are inhibiting the calcium-dependent pro-protein convertase enzyme furin (Kacprzak et al. 2004), and thereby blocking activation of potentially damaging proteins.

The invention demonstrates that cationic amino acid rich CPP, particularly arginine-rich CPPs or carrier-peptides (e.g. R12; SEQ ID NO: 9, R15; SEQ ID NO: 12), protamine; (SEQ ID NOs: 32 to 36), display a high level of neuroprotection, as opposed to CPPs in general. This raises the possibility that the mechanism of action of a neuroprotective peptide fused to a CPP is largely, if not exclusively the result of an enhanced neuroprotective effect of the carrier-peptide. Furthermore, the mechanism by which arginine-rich CPPs exert their neuroprotective action may be linked to endocytosis, a predominant carrier-peptide cellular uptake route, rather than by an interaction with a specific cytoplasmic target. In contrast, a neuroprotective peptide fused to a carrier-peptide entering a cell by endocytosis must first escape the endosome, which is known to be a highly inefficient process (AI-Taei et al., 2006; EI-Sayed et al., 2009; Appelbaum et al., 2012; Qian et al., 2014), before it can interact with its cytoplasmic target, hereby rendering it highly unlikely that the peptide can act through interaction with its intended target.

With respect to CPP intracellular entry, the predominant mechanism is considered to be by endocytosis (macropinocytosis) (Palm-Apergi et al., 2012). Although less relevant to the present invention, a recent report has demonstrated that cargo properties may also promote a direct cell entry mechanism by certain CPPs (Hirose et al., 2012). However, what is potentially highly relevant is how specific cargos, peptide or otherwise, may affect CPPs by enhancing their neuroprotective action, improving translocation efficiency and/or as demonstrated by Cardozo et al., (2007) increasing their toxicity. This is especially important when the cargo itself is neuroprotective, because as mentioned above, this makes discerning the neuroprotective effect between the CPP and the cargo very difficult. For example, in a previous studies (Meade et al., 2010a), the addition of three amino acid residues (Pro, Lys, Ile) from the PYC36 (SEQ ID NO: 24) peptide to the TAT-D (SEQ ID NO: 20) peptide (AM8D-TAT; SEQ ID NO: 43) resulted in IC50 values decreasing from >15 μM for TAT-D (SEQ ID NO: 20) to 1.1 μM for AM8D-TAT (SEQ ID NO: 43) in the glutamic acid model.

A positive effect with the TAT (SEQ ID NO: 21) peptide control has not always been observed. There are a number of possible explanations and to address this question: it is first necessary to differentiate studies using the TAT (SEQ ID NO: 21) peptide only (i.e. GRKKRRQRRRG), versus studies using TAT (SEQ ID NO: 21) fused to a reporter protein (e.g. GFP, β-gal) or peptide (e.g. HA and/or 6×HIS tag, scrambled peptide) as a control. With respect to the studies that have used the TAT (SEQ ID NO: 21) peptide by itself as a control, it is possible TAT (SEQ ID NO: 21) was ineffective at the dose used and/or the injury model was too severe to uncover a neuroprotective effect. For example, Boresello et al., (2003) did not detect a neuroprotective effect with the TAT (SEQ ID NO: 21) peptide following a 12, 24 or 48 hour exposure of cortical neuronal cultures to 100 μM NMDA. In contrast the L-JNKI-1 (SEQ ID NO: 26) peptide was effective at 12 and 24 hours, while the protease resistant D-JNKI-1 (SEQ ID NO: 25) peptide was effective at all time-points. Given the superior efficacy of the JNKI-1 (SEQ ID NOs: 25 and 26) peptides compared to the TAT (SEQ ID NO: 21) peptide, it is possible that at the concentration tested, TAT (SEQ ID NO: 21) was not neuroprotective or that any neuroprotective effects were overridden due to NMDA insult severity. In a study by Ashpole and Hudmon (2011) a modest protective effect with the TAT (SEQ ID NO: 21) peptide was observed in cortical neuronal cultures following glutamic acid exposure. Furthermore, the authors concluded that since the TAT (SEQ ID NO: 21) peptide provided little protection, the neuroprotection observed for their CAMKII inhibitory peptide was not due to the "import sequence" (i.e. TAT; SEQ ID NO: 21). However, it cannot be ruled out that the CAMKII inhibitory peptide increased the potency of the TAT (SEQ ID NO: 21) peptide. Lastly, it is possible that the TAT (SEQ ID NO: 21) peptide is only neuroprotective in specific injury models and cell types.

In studies using TAT (SEQ ID NO: 21) fused to a reporter protein or control peptide, in addition to the points raised above, it is also likely that the control protein/peptide may act to dampen or nullify the TAT (SEQ ID NO: 21) peptide's neuroprotective properties. Based on the many studies that have used TAT-fused proteins/peptides as controls and showed no neuroprotective effects, this would appear to be the case (e.g. Kilic et al., 2003; Doeppner et al., 2009). It needs to be borne in mind, however, that the mere fact that a protein is a CPP does not necessarily mean that it will be neuroprotective, which is borne out by the fact that PTD-4 (SEQ ID NO: 14) peptide (a modified TAT (SEQ ID NO: 21) peptide with 33× better transduction efficiency than TAT itself; Ho et al., 2001) has little to no neuroprotective properties.

TABLE 5

Amino acid sequences of different protamine (salmon) peptides; amino acid residues/arginine residues and molecular weights.

| SEQ ID NO.: | Name of Sequence | Type | Other information | Sequence | aa's/arg residues | MW (da) |
|---|---|---|---|---|---|---|
| — | Protamine sulphate mixture; Ptm | Polypeptide mixture | Injectable/IV form | Protamine 1-Protamine 4[1] | 32/21 | ≈4,500 |
| 32 | Protamine 1; Ptm1 | Polypeptide | Peak 1 HPLC[a] | PRRRRSSSRPIRRRRRPRASRRRRGG RRRR | 32/21 | 4,236 |
| 33 | Protamine 2; Ptm2 | Polypeptide | Peak 2 HPLC[a] | PRRRRSSRPVRRRRRPRVSRRRRRGGR RRR | 31/21 | 4,163 |
| 34 | Protamine 3; Ptm3 | Polypeptide | Peak 3 HPLC[a] | PRRRRSSSRPVRRRRRPRVSRRRRRGGR RRR | 31/20 | 4,094 |
| 35 | Protamine 4; Ptm4 | Polypeptide | Peak 4 HPLC[a] | PRRRRASRRIRRRRRPRVSRRRRRGGRR RR | 30/21 | 4,064 |
| 36 | Protamine 5; Ptm5 | Polypepoide | SwissProt[c] | PRRRRSSSRPVRRRRRPRVSRRRRRGG RRRR | 32/21 | 4,250 |
| 37 | Low molecular weight protamine (LMWP) | Polypepoide | Derived from protamine[b] | VSRRRRRRGGRRRR | 14/10 | 1,880 |
| 38 | Protamine 5 nucleotide sequence | Ptm 5, DNA coding sequence | SwissProt[c] | 5'ATGCCCAGAAGACGCAGATCCTCCAG CCGACCTGTCCGCAGGCGCCGCCGCCCT AGGGTGTCCCGACGTCGTCGCAGGAGAG GAGGCCGCAGGAGGCGT-3' | N/A | N/A |

(Protamini peptide sequences (salmon) present in protamine sulphate for clinical use or SwissProt data base. [a = Peaks 1-4 identified following HPLC of protamine sulphate[1]; b = Sequence in SwissProt (Swissprot: P14402). (1) Hoffmann JA1, Chance R E, Johnson M G. 1990. Purification and analysis of the major components of chum salmon protamine contained in insulin formulations using high-performance liquid chromatography. Protein Expr Purif. 1(2): 127-33. (2) Chang L C, Lee H F, Yang Z, Yang V C. 2001. Low molecular weight protamine (LMWP) as nontoxic heparin/low molecular weight heparin antidote (I): preparation and characterization. PharmSci. 3(3): E17).

Experimental Example 1

Neuroprotection Following Glutamic Acid Exposure

Figure 11:
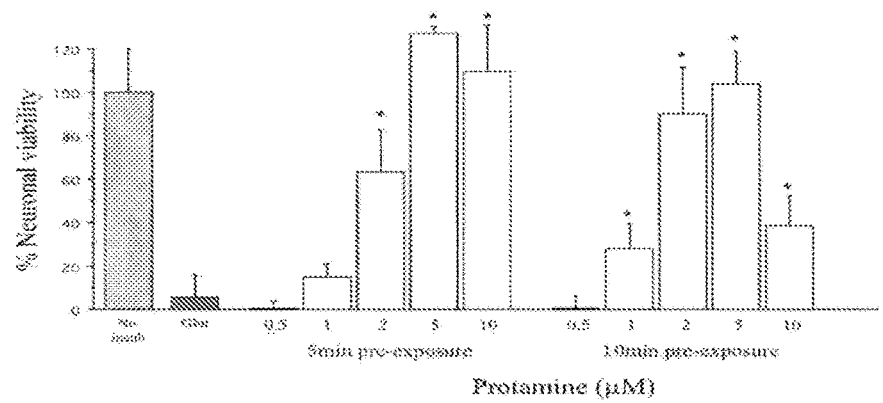
FIG. 11 shows the results of the glutamic acid excitotoxicity model; concentration of protamine (Ptm1-4 mixture; SEQ ID NOs: 32 to 35) in μM. Treatment of neuronal cultures with protamine (Ptm1-4 mixture; SEQ ID NOs: 32 to 35) was for 5 or 10 minutes prior to glutamic acid exposure (100 μM), (5 minutes at 37° C.) only. Neuronal viability 24 hours following glutamic acid exposure and treatment with different protamine (Ptm1-4 mixture; SEQ ID NOs: 32 to 35) concentrations or no treatment (Glut). MTS data were expressed as percentage neuronal viability with no insult control taken as 100% viability (mean±SD; n=4-6; *P<0.05).
Figure 12:
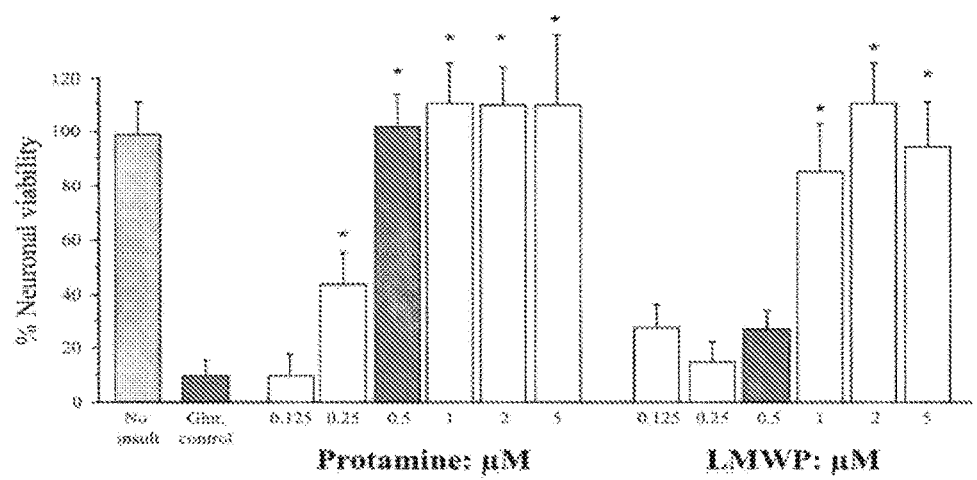
FIG. 12 shows the results of the glutamic acid excitotoxicity model; concentration of protamine (Ptm1-4 mixture; SEQ ID NOs: 32 to 35) and low molecular weight protamine (LMWP; SEQ ID NO: 37) in μM. Treatment of neuronal cultures with protamine (Ptm1-4; SEQ ID NOs: 32 to 35) or LMWP (SEQ ID NO: 37) was for 15 minutes prior to and during glutamic acid exposure (100 μM), which was for 5 minutes at 37° C. Neuronal viability 24 hours following glutamic acid exposure and treatment with different protamine (Ptm1-4 mixture; SEQ ID NOs: 32 to 35) or LMWP (SEQ ID NO: 37) concentrations or no treatment (Glut control). MTS data were expressed as percentage neuronal viability with no insult control taken as 100% viability (mean±SD; n=4-6; *P<0.05).
Figure 13:
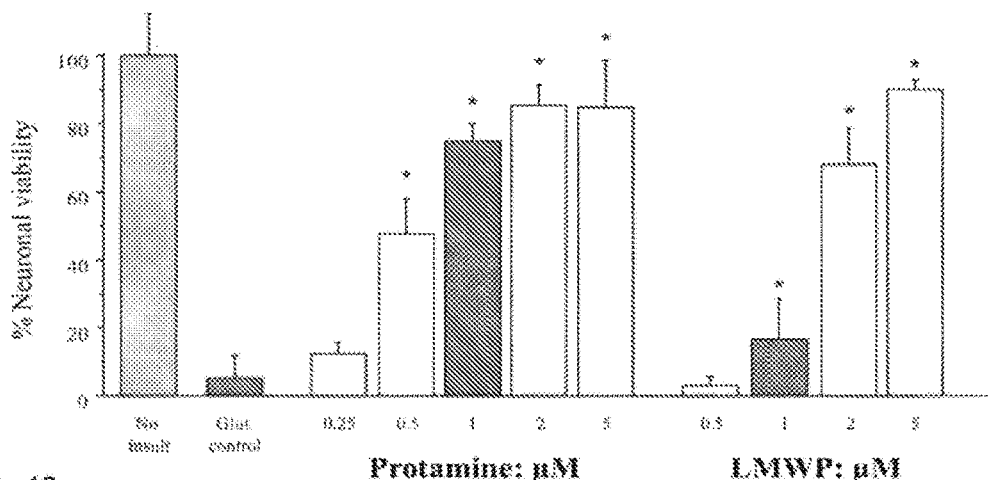
FIG. 13 shows the results of the glutamic acid excitotoxicity model; concentration of protamine (Ptm1-4 mixture; SEQ ID NOs: 32 to 35) and low molecular weight protamine (LMWP; SEQ ID NO: 37) in μM. Treatment of neuronal cultures with protamine (Ptm1-4 mixture; SEQ ID NOs: 32 to 35) or LMWP (SEQ ID NO: 37) was for 15 minutes prior to and during glutamic acid exposure (100 μM), which was for 5 minutes at 37° C. Neuronal viability 24 hours following glutamic acid exposure and treatment with different protamine (Ptm1-4 mixture; SEQ ID NOs: 32 to 35) or LMWP (SEQ ID NO: 37) concentrations or no treatment (Glut control). MTS data were expressed as percentage neuronal viability with no insult control taken as 100% viability (mean±SD; n=4-6; *P<0.05).
Figure 15:
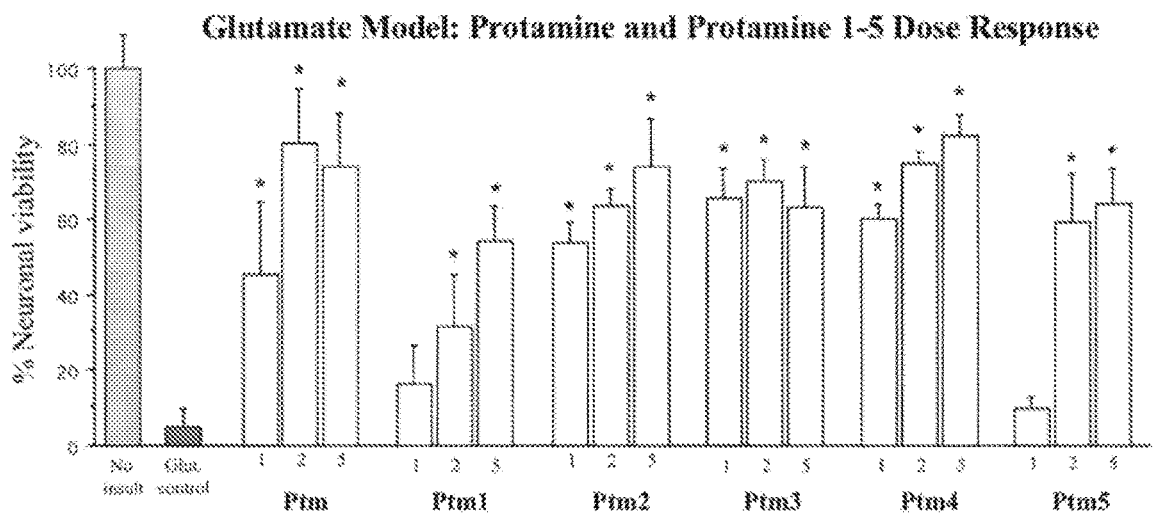
FIG. 15 shows the results of the glutamic acid excitotoxicity model; concentration of protamine (Ptm1-4 mixture; SEQ ID NOs: 32 to 35) and protamine peptides 1 to 5 ("Ptm 1 to 5"; SEQ ID NOs: 32 to 36) in μM. Treatment of neuronal cultures with protamine (Ptm1-4 mixture; SEQ ID NOs: 32 to 35) and protamine peptides ("Ptm 1 to 5"; SEQ ID NOs: 32 to 36) was for 15 minutes prior to glutamic acid exposure (100 μM), which was for 5 minutes at 37° C. Neuronal viability 24 hours following glutamic acid exposure and treatment with different protamine (Ptm1-4 mixture; SEQ ID NOs: 32 to 35) and protamine peptides ("Ptm 1 to 5"; SEQ ID NOs: 32 to 36) concentrations or no treatment (Glut control). MTS data were expressed as percentage neuronal viability with no insult control taken as 100% viability (mean±SD; n=4-6; *P<0.05).

Protamine sulphate (protamine; Ptm1-4 mixture SEQ ID NOs: 32 to 35) provided significant neuroprotection in a dose response manner (FIGS. 9, 10, 12, 13, 15). Visual assessment of cultures post-injury also confirmed the neuroprotective effect that ranged from ≈5% for untreated glutamic acid exposed cultures to 85-100% survival for protamine treated cultures. In addition, a 5 or 10 minute protamine (Ptm1-4 mixture SEQ ID NOs: 32 to 35) pre-exposure was also highly neuroprotective resulting 100% neuronal survival (FIG. 11). In dose response experiments, low molecular weight protamine (LMWP) (SEQ ID NO: 37), protamine 1 (Ptm1) (SEQ ID NO: 32), protamine 2 (Ptm2) (SEQ ID NO: 33), protamine 3 (Ptm3) (SEQ ID NO: 34), protamine 4 (Ptm4) (SEQ ID NO: 35), protamine 5 (Ptm5) (SEQ ID NO: 36), peptide were also neuroprotective (FIGS. 12, 13, 15).

Figure 14:
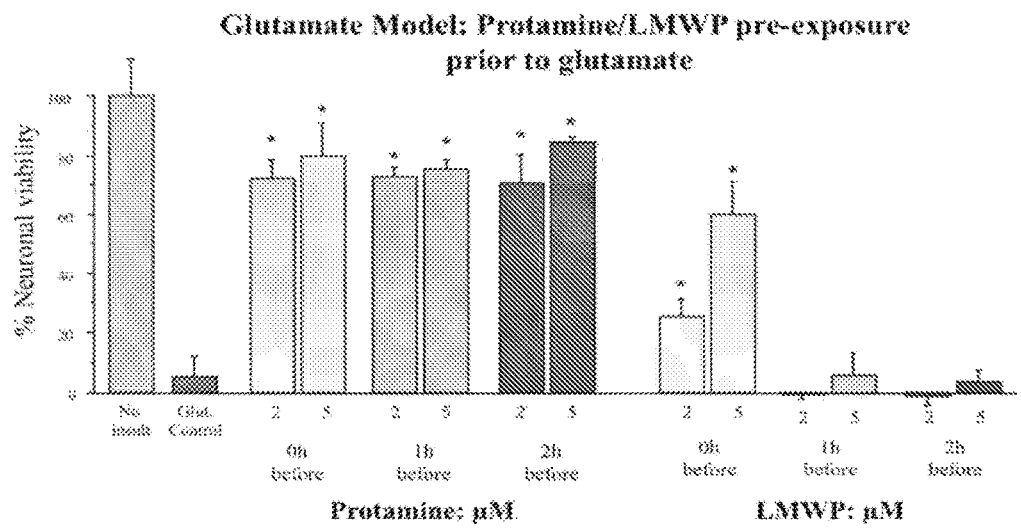
FIG. 14 shows the results of the glutamic acid excitotoxicity model; concentration of protamine (Ptm1-4 mixture; SEQ ID NOs: 32 to 35) and LMWP (SEQ ID NO: 37) in μM. Treatment of neuronal cultures with protamine (Ptm1-4 mixture; SEQ ID NOs: 32 to 35) was for 10 minutes immediately before, or 1 or 2 hours before glutamic acid exposure (100 μM; 5 minutes at 37° C.) only. Neuronal viability 24 hours following glutamic acid exposure and treatment with different protamine (Ptm1-4 mixture; SEQ ID NOs: 32 to 35) or LMWP (SEQ ID NO: 37) concentrations or no treatment (Glut Control). MTS data were expressed as percentage neuronal viability with no insult control taken as 100% viability (mean±SD; n=4-6; *P<0.05).

In protamine (Ptm1-4 mixture SEQ ID NOs: 32 to 35) and LMWP (SEQ ID NO: 37) pre-exposure experiments, protamine (Ptm1-4 mixture SEQ ID NOs: 32 to 35) was neuroprotective when neurons where exposed to protamine (Ptm1-4 mixture SEQ ID NOs: 32 to 35) immediately before and 1 or 2 hours prior to glutamic acid insult, while LMWP (SEQ ID NO: 37) was only neuroprotective when exposure was immediately before glutamic acid insult (FIG. 14).

Experimental Example 2

Neuroprotection Following Oxygen-Glucose Deprivation (OGD)

Figure 16:
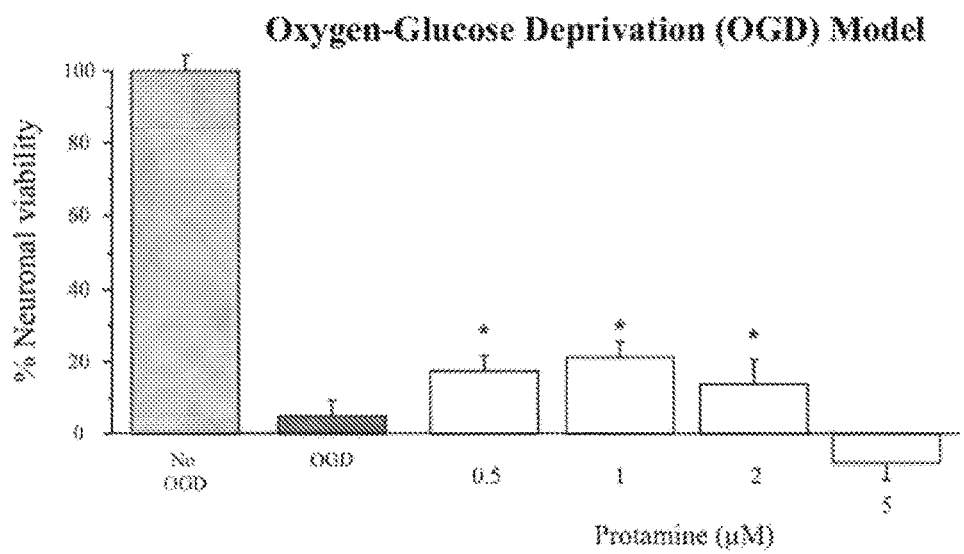
FIG. 16 shows the results of the oxygen-glucose deprivation (OGD) model; concentration of protamine (Ptm1-4 mixture; SEQ ID NOs: 32 to 35) in μM. Treatment of neuronal cultures with protamine (Ptm1-4 mixture; SEQ ID NOs: 32 to 35) was immediately after 50 minutes of OGD and until experiment end (24 h). Neuronal viability 24 hours following OGD and treatment with different protamine (Ptm1-4 mixture; SEQ ID NOs: 32 to 35) concentrations or no treatment (OGD). MTS data were expressed as percentage neuronal viability with no OGD control taken as 100% viability (mean SD; n=4-6; *P<0.05).
Figure 17:
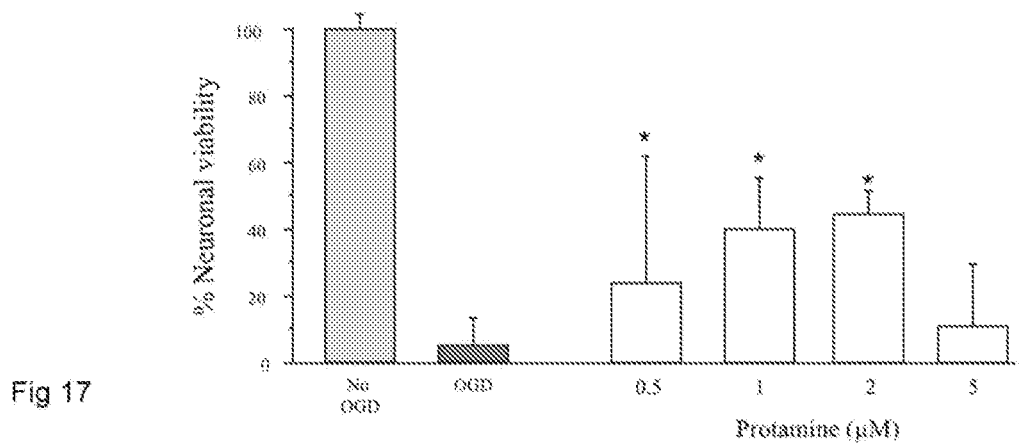
FIG. 17 shows the results of the oxygen-glucose deprivation (OGD) model; concentration of protamine (Ptm1-4 mixture; SEQ ID NOs: 32 to 35) in μM. Treatment of neuronal cultures with protamine (Ptm1-4 mixture; SEQ ID NOs: 32 to 35) was immediately after 50 minutes of OGD and until experiment end (24 h). Neuronal viability 24 hours following OGD and treatment with different protamine (Ptm1-4 mixture; SEQ ID NOs: 32 to 35) concentrations or no treatment (OGD). MTS data were expressed as percentage neuronal viability with no OGD control taken as 100% viability (mean±SD; n=4-6; *P<0.05).
Figure 18:
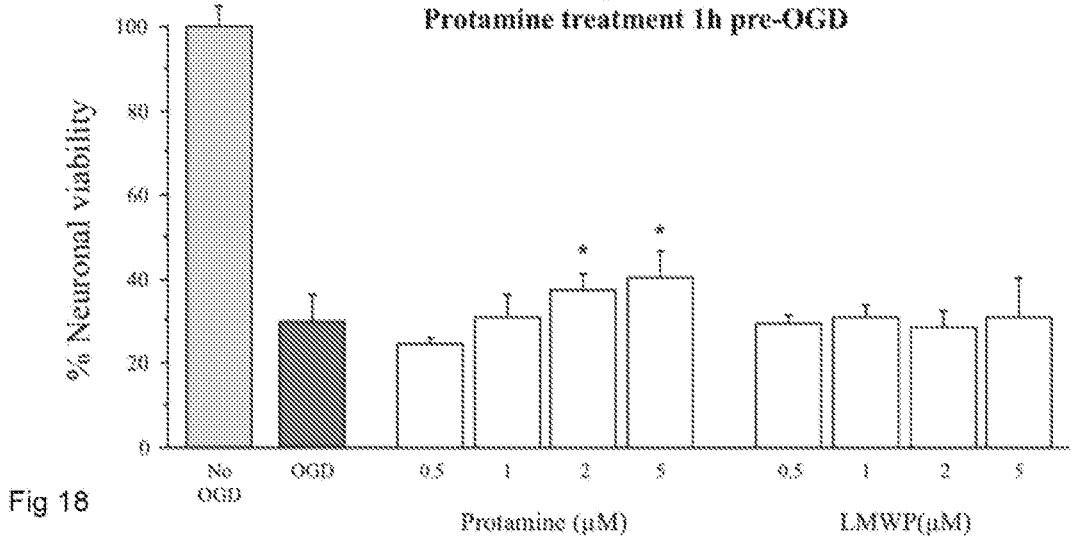
FIG. 18 shows the results of the oxygen-glucose deprivation (OGD) model; concentration of protamine (Ptm1-4 mixture; SEQ ID NOs: 32 to 35) and LMWP (SEQ ID NO: 37) in μM. Treatment of neuronal cultures with protamine (Ptm1-4 mixture; SEQ ID NOs: 32 to 35) or LMWP (SEQ ID NO: 37) was for 10 minutes, 1 hour before 50 minutes of OGD. Neuronal viability 24 hours following OGD and pre-treatment with different protamine (Ptm1-4 mixture; SEQ ID NOs: 32 to 35 or LMWP: SEQ ID NO: 37) concentrations or no treatment (OGD). MTS data were expressed as percentage neuronal viability with no OGD control taken as 100% viability (mean±SD; n=4-6; *P<0.05).
Figure 19:
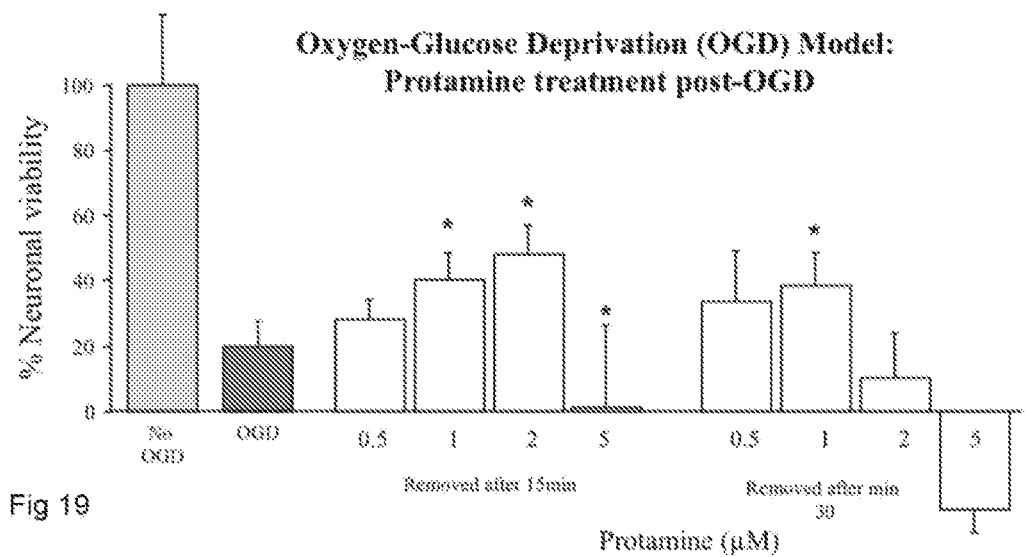
FIG. 19 shows the results of the oxygen-glucose deprivation (OGD) model; concentration of protamine (Ptm1-4 mixture; SEQ ID NOs: 32 to 35) in µM. Treatment of neuronal cultures with protamine (Ptm1-4 mixture; SEQ ID NOs: 32 to 35) was for 15 or 30 minutes, after 50 minutes of OGD. Neuronal viability 24 hours following OGD and post-treatment with different protamine (Ptm1-4 mixture; SEQ ID NOs: 32 to 35) concentrations or no treatment (OGD). MTS data were expressed as percentage neuronal viability with no OGD control taken as 100% viability (mean±SD; n=4-6; *P<0.05).
Figure 20:
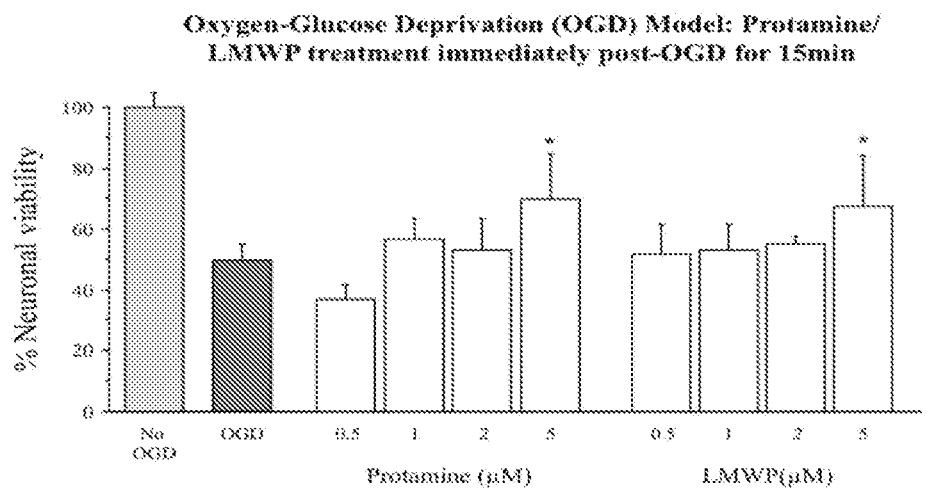
FIG. 20 shows the results of the oxygen-glucose deprivation (OGD) model; concentration of protamine (Ptm1-4 mixture; SEQ ID NOs: 32 to 35) and LMWP (SEQ ID NO: 37) in µM. Treatment of neuronal cultures with protamine (Ptm1-4 mixture; SEQ ID NOs: 32 to 35) or LMWP (SEQ ID NO: 37) was for 15 minutes, after 50 minutes of OGD. Neuronal viability 24 hours following OGD and post-treatment with different protamine (Ptm1-4 mixture; SEQ ID NOs: 32 to 35) or LMWP (SEQ ID NO: 37) concentrations or no treatment (OGD). MTS data were expressed as percentage neuronal viability with no OGD control taken as 100% viability (mean±SD; n=4-6; *P<0.05).
Figure 21:
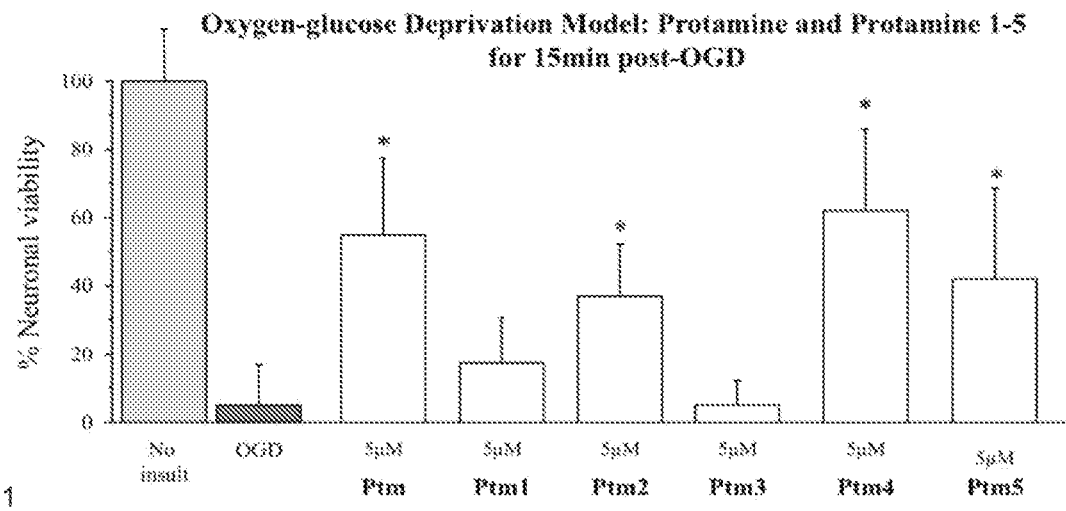
FIG. 21 shows the results of the oxygen-glucose deprivation (OGD) model; concentration of protamine (Ptm1-4 mixture; SEQ ID NOs: 32 to 35) and protamine peptides ("Ptm 1 to 5"; SEQ ID NOs: 32 to 36) in µM (5 µM). Treatment of neuronal cultures with protamine (Ptm1-4 mixture; SEQ ID NOs: 32 to 35 or "Ptm 1 to 5"; SEQ ID NOs: 32 to 36) was for 15 minutes, after 45 minutes of OGD. Neuronal viability 24 hours following OGD and post-treatment with different protamine (Ptm1-4 mixture; SEQ ID NOs: 32 to 35) and protamine peptides ("Ptm 1 to 5"; SEQ ID NOs: 32 to 36) concentrations or no treatment (OGD). MTS data were expressed as percentage neuronal viability with no OGD control taken as 100% viability (mean±SD; n=5; *P<0.05).
Figure 22:
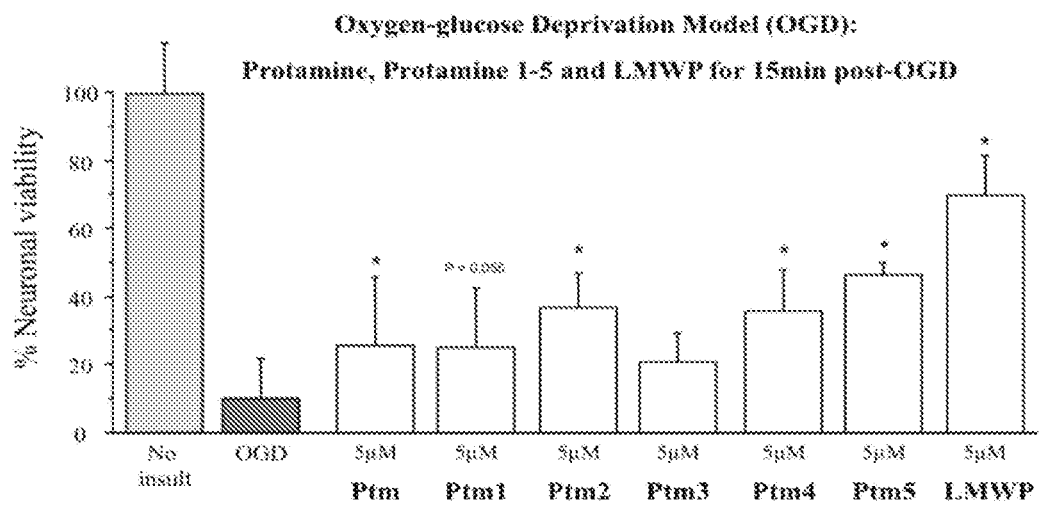
FIG. 22 shows the results of the oxygen-glucose deprivation (OGD) model; concentration of protamine (Ptm1-4 mixture; SEQ ID NOs: 32 to 35), protamine peptides ("Ptm 1 to 5"; SEQ ID NOs: 32 to 36) and low molecular weight protamine (LMWP; SEQ ID NO: 37) peptides in µM (5 µM). Treatment of neuronal cultures with protamine (Ptm1-4 mixture; SEQ ID NOs: 32 to 35 or "Ptm 1 to 5"; SEQ ID NOs: 32 to 36 or LMWP; SEQ ID NO: 37) was for 15 minutes, after 45 minutes of OGD. Neuronal viability 24 hours following OGD and post-treatment with different protamine protamine (Ptm1-4 mixture; SEQ ID NOs: 32 to 35) and protamine peptides ("Ptm 1 to 5"; SEQ ID NOs: 32 to 36 or LMWP; SEQ ID NO: 37) concentrations or no treatment (OGD). MTS data were expressed as percentage neuronal viability with no OGD control taken as 100% viability (mean±SD; n=4-6; *P<0.05).

In the OGD model protamine (Ptm1-4 mixture SEQ ID NOs: 32 to 35) was neuroprotective when neurons were treated with peptide 1 hour before insult (FIG. 18) or post-insult (FIG. 16, 17). In addition, when added for 15 or 30 minutes, post-OGD protamine (Ptm1-4 mixture SEQ ID NOs: 32 to 35) was also neuroprotective (FIGS. 19, 20, 21, 22). LMWP (SEQ ID NO: 37) was not neuroprotective when neurons were pre-exposed to the peptide 1 hour before OGD, but it was neuroprotective when added for 15 minutes post-OGD. In addition when protamine peptides (Ptm1-Ptm5) (SEQ ID NOs: 32 to 36) and LMWP (SEQ ID NO: 37) were added for 15 minutes post-OGD, peptides Ptm2 (SEQ ID NO: 33), Ptm4 (SEQ ID NO: 35), Ptm5 (SEQ ID NO: 36) and LMWP (SEQ ID NO: 37) were neuroprotective (FIG. 22).

Experimental Example 3

Protection of bEND3 Cells Following Oxygen-Glucose Deprivation (OGD)

Figure 23:
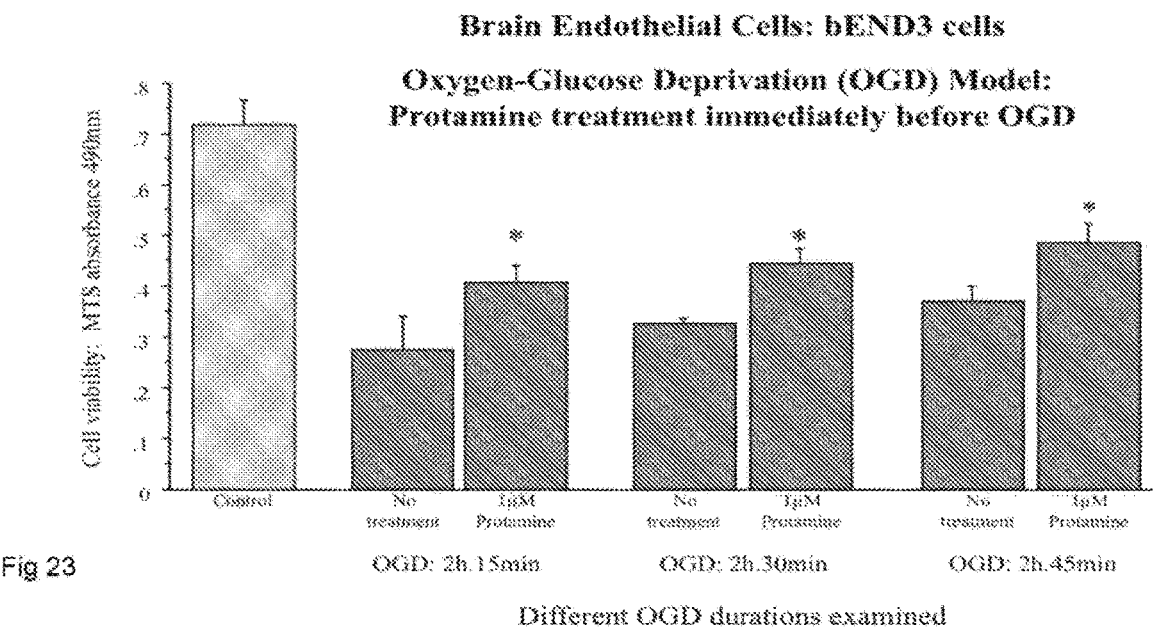
FIG. 23 shows the results of the oxygen-glucose deprivation (OGD) model using brain endothelial cells (bEND 3 cells); concentration of protamine (Ptm1-4 mixture; SEQ ID NOs: 32 to 35) in µM. Treatment of bEND3 cultures with protamine (Ptm1-4 mixture; SEQ ID NOs: 32 to 35) was from 15 minutes immediately before 3 different OGD durations (2 h 15 min, 2 h 30 min and 2 h 45 min) and until experiment end (24 h). Cell viability was measured 24 hours following OGD. MTS data were expressed as percentage neuronal viability with no OGD control taken as 100% viability (mean±SD; n=4-6; *P<0.05).
Figure 24:
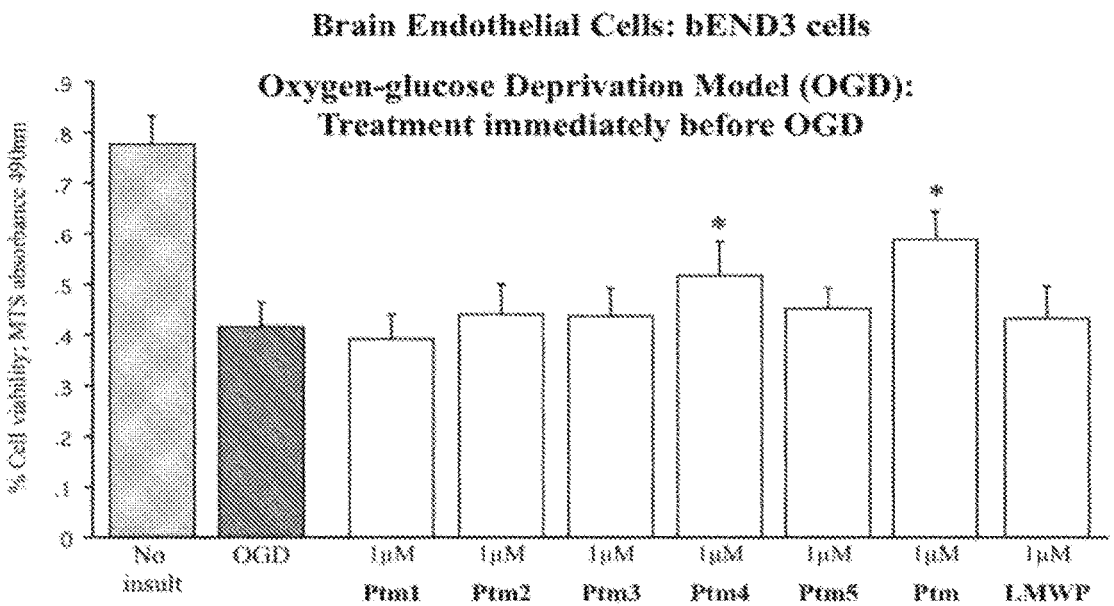
FIG. 24 shows the results of exposure of protamine peptides (Ptm1-4 mixture; SEQ ID NOs: 32 to 35 or "Ptm 1 to 5"; SEQ ID NOs: 32 to 36 or LMWP; SEQ ID NO: 37) to brain endothelial cells (bEND3 cells); concentration of protamine 1 µM. Protamine peptides 1-5 ("Ptm1 to Ptm5"; SEQ ID NOs: 32 to 36), protamine sulphate (Ptm1-4 mixture; SEQ ID NOs: 32 to 35), and low molecular weight protamine (LMWP; SEQ ID NO: 37) added to bEND3 cell cultures for 15 min immediately before OGD (2 h 30 min duration). Cell viability assessed 24 hours after OGD using MTS assay. MTS data were expressed as absorbance values at 490 mm (mean±SD; n=4-6; *P<0.05).
Figure 25:
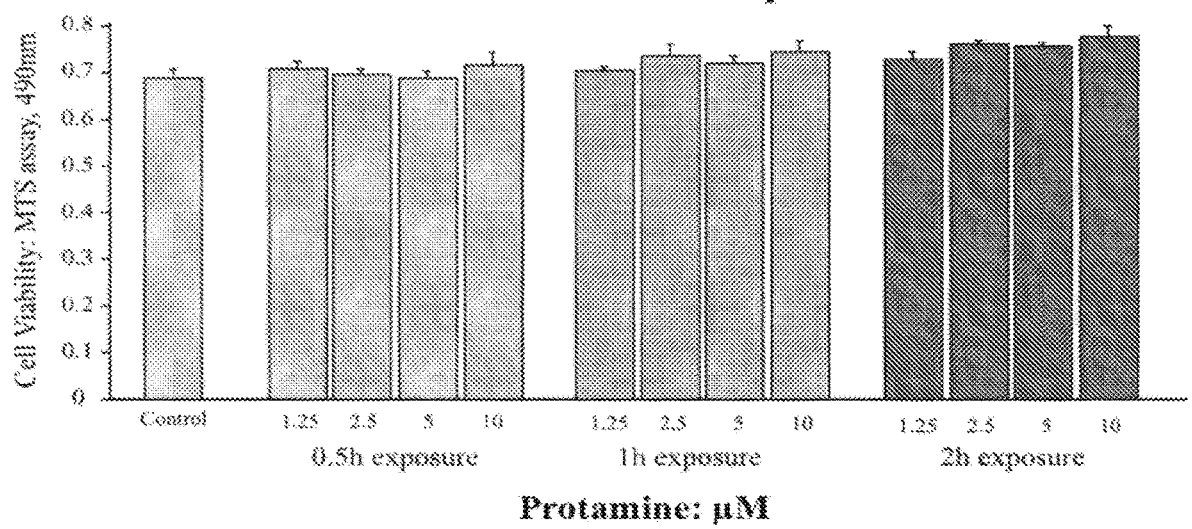
FIG. 25 shows the results of exposure of protamine (Ptm1-4 mixture; SEQ ID NOs: 32 to 35) to brain endothelial cells (bEND3 cells); concentration of protamine in µM. Treatment of bEND3 cultures with protamine (Ptm1-4 mixture; SEQ ID NOs: 32 to 35) was for 0.5, 1 or 2 hours. Cell viability 2 hours following protamine (Ptm1-4 mixture; SEQ ID NOs: 32 to 35) exposure or no treatment (Control). MTS data were expressed as absorbance values at 490 mm (mean±SD; n=4-6; *P<0.05).
Figure 26:
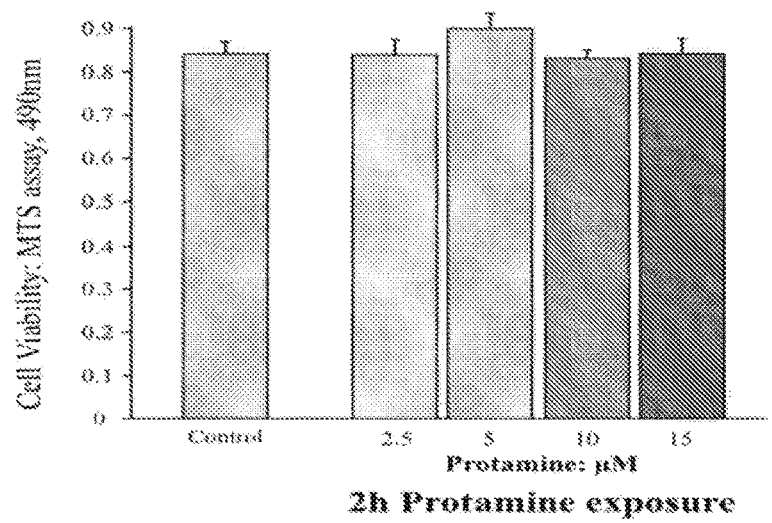
FIG. 26 shows the results of exposure of protamine (Ptm1-4 mixture; SEQ ID NOs: 32 to 35) to brain endothelial cells (bEND3 cells); concentration of protamine in µM. Treatment of bEND3 cultures with protamine (Ptm1-4 mixture; SEQ ID NOs: 32 to 35) was for 2 hours. Cell viability 2 hours following protamine (Ptm1-4 mixture; SEQ ID NOs: 32 to 35) exposure or no treatment (Control). MTS data were expressed as absorbance values at 490 mm (mean±SD; n=4-6; *P<0.05).
Figure 43:
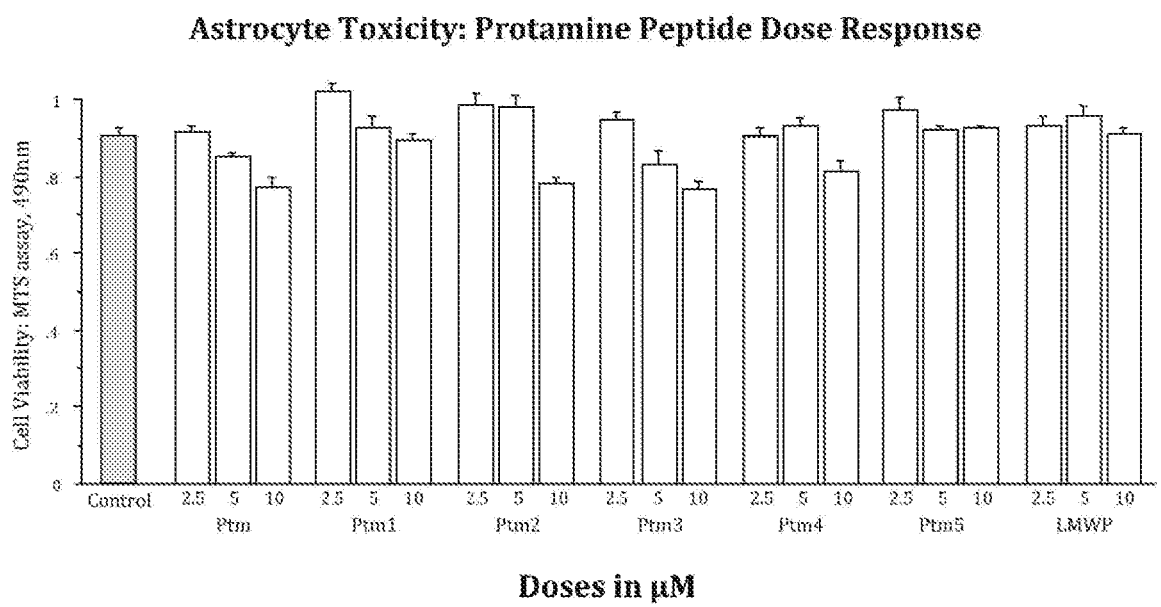
FIG. 43 shows the results of exposure of protamine peptides 1-5 (Ptm1-Ptm5; SEQ ID NOs: 32 to 36), protamine sulphate (Ptm1-4 mixture; SEQ ID NOs: 32 to 35), and low molecular weight protamine (LMWP; SEQ ID NO: 37) to primary rat astrocytes; concentration of protamine in μM. Treatment of astryocyte cultures with protamine was for 24 hours. Cell viability 24 hours following protamine exposure or no treatment (Control). MTS data were expressed as absorbance values at 490 mm (n=4).

In the OGD model, protamine (Ptm1-4 mixture SEQ ID NOs: 32 to 35) and protamine 4 (ptm4) (SEQ ID NO: 35) was protective for blood brain barrier (bEND3) endothelial cells when treated with peptide 15 minutes before OGD (FIG. 23, 24). In addition, exposure of bEND3 to protamine (Ptm1-4 mixture; SEQ ID NOs: 32 to 35) at concentrations ranging from 1.25 to 15 µM for between 0.5 to 2 hours did not cause any significant toxicity based on MTS assay (FIG. 25, 26). FIG. 43 shows that Ptm1-Ptm5 (SEQ ID NOs: 32 to 36), and low molecular weight protamine (LMWP; SEQ ID NO: 37) at concentration from 2.5 to 10 µM did not cause significant astrocyte cell death following 24 hour exposure.

General Observations and Discussion

The Applicant assessed the arginine-rich protamine sulphate (protamine; Ptm1-4 mixture; SEQ ID NOs: 32 to 35), protamine peptides 1-5 (Ptm1-Ptm5, SEQ ID NOs: 32 to 36, respectively), and low molecular weight protamine (LMWP, SEQ ID NO: 37) for their neuroprotective properties in cortical neuronal cultures following exposure to glutamic acid or in vitro ischemia (oxygen-glucose deprivation—OGD). Both injury models are commonly used to mimic the effects of ischemic stroke.

The Applicant also assessed the use of protamine peptides (SEQ ID NOs: 32 to 37) in protecting blood brain barrier (bEND3) endothelial cells from OGD.

Protamine (Ptm1-4 mixture SEQ ID NOs: 32 to 35) displayed consistent and high-level neuroprotective activity in both the glutamic acid and OGD injury models, while protamine (Ptm1-4 mixture SEQ ID NOs: 32 to 35) also provided protection in the bEND3 cells. LMWP (SEQ ID NO: 37) was slightly less effective (based on dose concentrations to achieve equivalent neuroprotection as protamine; Ptm1-4 mixture SEQ ID NOs: 32 to 35) in the neuronal glutamic acid and OGD injury models. This is most likely due to the LMWP (SEQ ID NO: 37) peptide containing fewer arginine residues. Protamine peptides 1-5 (Ptm 1-Ptm5; SEQ ID NOs: 32 to 36) were also highly neuroprotective in the in the glutamic acid model, while Ptm2 (SEQ ID NO: 33), Ptm4 (SEQ ID NO: 35) and Ptm5 (SEQ ID NO: 36) were neuroprotective in the OGD model.

In a OGD study using bEND3 cells, a 15-minute pre-exposure with protamine (Ptm1-4 mixture SEQ ID NOs: 32 to 35) significantly increased cell viability and thus protection, after different duration of OGD (2 h:15 min, 2 h:30 min or 2 h:45 min). In addition, a 15-minute pre-exposure with Ptm4 (SEQ ID NO: 35) also significantly increased cell viability and thus protection, in the OGD model.

In a bEND3 toxicity study using protamine (Ptm1-4 mixture SEQ ID NOs: 32 to 35) at varying concentrations, it was revealed that protamine (Ptm1-4 mixture SEQ ID NOs: 32 to 35) is not toxic even at concentrations as high as 15 µM.

These findings demonstrate that protamine peptides (SEQ ID NOs: 32 to 36) of the invention have the ability to inhibit neurodamaging events/pathways associated with excitotoxic and ischemic injuries. Also, due to the effects of protamine (Ptm1-4 mixture; SEQ ID NOs: 32 to 35) in the pre-exposure trials, one new key finding was that protamine (Ptm1-4 mixture; SEQ ID NOs: 32 to 35) treatment of neurons 1 to 2 hours before glutamic acid or OGD exposure can induce a neuroprotective response, by reducing cell death. This is significant because there are a number of cerebrovascular (e.g. carotid endarterectomy) and cardiovascular (e.g. coronary artery bypass graft) surgical procedures where there is a risk a patient can suffer cerebral ischemia or a stroke resulting in brain injury. Therefore, protamine peptides (SEQ ID NOs: 32 to 36) may be able to be given 1-2 hours before such a procedure to protect the brain against any such cerebral ischaemic event.

The cytoprotective properties of the peptides of the invention suggest they are ideal neuroprotective drugs for the treatment of CNS injuries. In addition, as they are also likely to have cell penetrating properties [protamine (Ptm1-4 mixture; SEQ ID NOs: 32 to 35) is FDA approved for gene therapy delivery (DNA, viral vectors; Sorgi et al., 1997) and LMWP (SEQ ID NO: 37) is used as a cell penetrating peptide; Park et al., 2005] they are ideal carrier molecules to deliver neuroprotective drugs to the CNS following injury.

The neuroprotective effects of the peptides of the invention are likely to be related to the peptides' physical-chemical properties. Furthermore, it may well be that the neuroprotective action of arginine-rich protamine peptides (SEQ ID NOs: 32 to 37) is mediated at the cell membrane (e.g. receptors, ion channels). Studies have suggested that arginine-rich peptides including TAT (SEQ ID NO: 21) (Xu et al., 2008), R6 (SEQ ID NO: 3) (Ferrer-Montiel et al., 1988) and R9-CBD3 (SEQ ID NO: 44) (Feldman and Khanna 2013) and TAT-CBD3 (SEQ ID NO: 45) (Brustovetsky et al., 2014) may affect the function of cell surface receptors and ion channels, such as the NMDA receptor, resulting in reduced calcium influx. It is contemplated, however, that the peptide or peptides of the invention can act to block NMDA receptor functioning and/or block, down-regulate, or decelerate the influx of calcium. An alternative mechanism is that the protamine peptides (SEQ ID NOs: 32 to 37) interact and stabilise the outer mitochondrial membrane and thereby help to preserve mitochondrial function. Potential benefits are maintenance of ATP synthesis, reduced reactive oxygen species production, and improved calcium handling. To this end, the Applicant has observed that protamine (Ptm1-4 mixture; SEQ ID NOs: 32 to 35) can increase MTS absorbance levels above baseline levels in normal neurons and following injury (e.g. FIG. 11, 12; 5 μM). Since reduction of MTS to its formazan product primarily occurs in mitochondria, the ability of protamine (Ptm1-4 mixture; SEQ ID NOs: 32 to 35) to increase formazan levels is supportive that the peptide is improving mitochondrial function. Another potential mechanism is that these arginine-rich peptides are inhibiting the calcium-dependent pro-protein convertase enzyme furin (Kacprzak et al., 2004), and thereby blocking activation of potentially damaging proteins.

Figure 45:
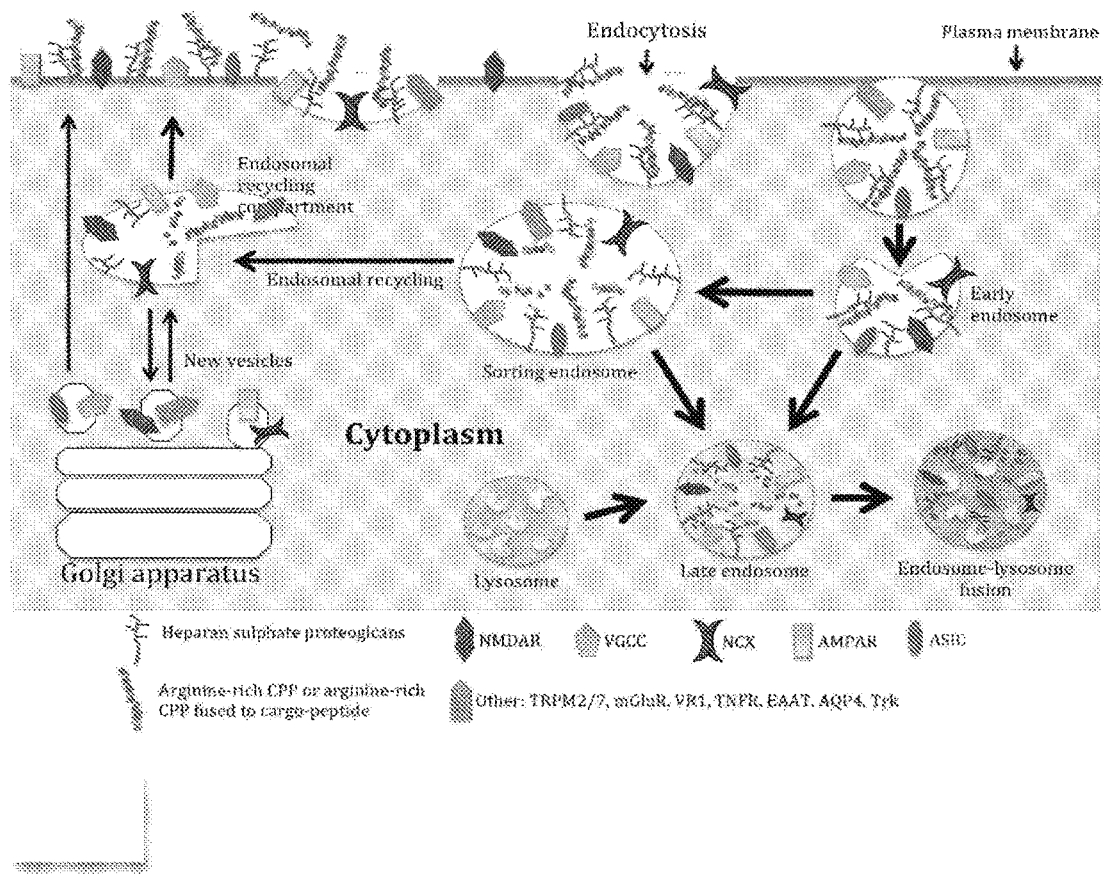
FIG. 45. Diagrammatic representation of proposed model of arginine-rich CPPs inducing endocytic internalization of neuronal cell surface structures. Note: model applies to neuronal synaptic and extra-synaptic plasma membranes and potentially the plasma membrane of astrocytes, pericytes, brain endothelial cells, oligodentrocytes and microglia. NMDAR: N-methyl-D-aspartate receptors; AMPAR: α-amino-3-hydroxy-5-methyl-4-isoxazolepropionic acid receptors; NCX: sodium calcium exchanger; VGCC: voltage-gated calcium channels (e.g. CaV2.2, CaV3.3); ASIC: acid-sensing ion channels; TRPM2/7: transient receptor potential cation channels 2 and 7: mGluR: metabotropic glutamate receptors; VR1: vanilloid receptor 1 or transient receptor potential cation channel subfamily V member 1; TNFR: tumor necrosis factor receptors; EAAT: excitatory amino-acid transporters; AQP4: Aquaporin 4; Trk: tropomyosin-receptor-kinase receptors.

With respect to protamine peptide intracellular entry, the predominant mechanism for arginine-rich peptides is considered to be by endocytosis (macropinocytosis) (Palm-Apergi et al., 2012). It is therefore likely, that during peptide endocytosis across the plasma membrane, it results in endosomal internalisation of cell surface structures (see FIG. 45). In the setting of neuronal excitotoxicity and ischemia, the down-regulation of ion channels would be beneficial as it reduces the normally neuro-damaging influx of calcium and other ions.

The Applicant is of the opinion that they have identified a new class or group of peptides that can serve as CPPs as well as neuroprotective peptides. The Applicant has found that poly-arginine or arginine-rich peptides, particularly those selected from protamine (SEQ ID NOs: 32 to 36) or low molecular weight protamine (SEQ ID NO: 37) (and mixtures and derivatives thereof, especially in the form of commercially available protamine sulphate; Ptm1-4 mixture; SEQ ID NOs: 32 to 35) posses novel neuroprotective or neuro-active properties. There is evidence that the peptides disclosed herein as part of the invention possess the same range of neuroprotective or neuro-active properties when used in vivo (Vaslin et al., 2009) and find use in treating neural injuries.

The Applicant has thus found that arginine-rich peptides and CPPs unrelated to TAT (SEQ ID NO: 21) posses novel neuroprotective properties, in particular poly-arginine sequences and sequences of between 10 and 32 amino acids in length which possess more than 10 arginine residues (such as protamine; SEQ ID NOs: 32 to 36, LMWP; SEQ ID NO: 37, and derivatives thereof). There is evidence that CPPs of the invention possess the same range of neuroprotective properties when used in vivo (Vaslin et al., 2009) and find use in treating neural injuries.

REFERENCES

Aarts M, Liu Y, Liu L, Besshoh S, Arundine M, Gurd J W, Wang Y T, Salter M W, Tymianski M (2002) Treatment of ischemic brain damage by perturbing NMDA receptor-PSD-95 protein interactions. Science 298:846-850.

ARAMIS (2011) Project number: 8909.1. http://www.aramis.admin.ch.

Arthur P G, Matich G P, Pang W W, Yu D Y, Bogoyevitch M A (2007) Necrotic death of neurons following an excitotoxic insult is prevented by a peptide inhibitor of c-jun N-terminal kinase. J Neurochem 102:65-76.

Borsello T, Clarke P G, Hirt L, Vercelli A, Repici M, Schorderet D F, Bogousslavsky J, Bonny C (2003) A peptide inhibitor of c-Jun N-terminal kinase protects against excitotoxicity and cerebral ischemia. Nat Med 9:1180-1186.

Brugidou J, Legrand C, Méry J, Rabié A (1995) The retro-inverso form of a homeobox-derived short peptide is rapidly internalised by cultured neurones: a new basis for an efficient intracellular delivery system. Biochem Biophys Res Commun 214:685-693.

Colombo A, Repici M, Pesaresi M, Santambrogio S, Forloni G, Borsello T (2007) The TAT-JNK inhibitor peptide interferes with beta amyloid protein stability. Cell Death Differ 14:1845-1848.

Craig A J, Meloni B P, Watt P M, Knuckey N W (2011) Attenuation of neuronal death by peptide inhibitors of AP-1 activation in acute and delayed in vitro ischaemia (oxygen/glucose deprivation) models. Int J Pept Res Ther 17: 1-6.

Doeppner T R, Nagel F, Dietz G P H, Weise J, Tönges L, Schwarting S, Bähr M (2009) TAT-HSP70-mediated neuroprotection and increased survival of neuronal precursor cells after focal cerebral ischemia in mice. J Cereb Blood Flow Metab 29:1187-1196.

Dolgin E (2012) To serve and neuroprotect. Nat Med 18:1003-1006.

Frankel A D, Pabo C O (1988) Cellular uptake of the tat protein from human immunodeficiency virus. Cell 55:1189-1193.

Green M, Loewenstein P M (1988) Autonomous functional domains of chemically synthesized human immunodeficiency virus tat trans-activator protein. Cell 55:1179-1188.

Hirose H, Takeuchi T, Osakada H, Pujals S, Katayama S, Nakase I, Kobayashi S, Haraguchi T, Futaki S (2012) Transient focal membrane deformation induced by arginine-rich peptides leads to their direct penetration into cells. Mol Ther 20:984-993.

Ho A, Schwarze S R, Mermelstein S J, Waksman G, Dowdy S F (2001) Synthetic protein transduction domains: enhanced transduction potential in vitro and in vivo. Cancer Res 61:474-477.

Kacprzak M M, Peinado J R, Than M E, Appel J, Henrich S, Lipkind G, Houghten R A, Bode W, Lindberg I (2004) Inhibition of furin by polyarginine-containing peptides: nanomolar inhibition by nona-D-arginine. J Biol Chem 279:36788-36794.

Kilic Ü, Kilic E, Dietz G P H, Bähr M (2003) Intravenous TAT-GDNF is protective after focal cerebral ischemia in mice. Stroke 34:1304-1310.

Lai Y, Du L, Dunsmore K E, Jenkins L W, Wong H R, Clark R S (2005) Selectively increasing inducible heat shock protein 70 via TAT-protein transduction protects neurons from nitrosative stress and excitotoxicity. J Neurochem 94:360-366.

Liu X, M, Pei D S, Guan Q H, Sun Y F, Wang X T, Zhang Q X, Zhang G Y (2006) Neuroprotection of Tat-GluR6-9c against neuronal death induced by kainate in rat hippocampus via nuclear and non-nuclear pathways. J Biol Chem 281:17432-17445.

Meade A J, Meloni B P, Mastaglia F L, Knuckey N W (2009) The application of cell penetrating peptides for the delivery of neuroprotective peptides/proteins in experimental cerebral ischemia studies. J Exp Stroke Transl Med 2:22-40.

Meade A J, Meloni B P, Mastaglia F L, Watt P M, Knuckey N W (2010a) AP-1 inhibitory peptides attenuate in vitro cortical neuronal cell death induced by kainic acid. Brain Res 1360:8-16.

Meade A J, Meloni B P, Cross J, Bakker A J, Fear M W, Mastaglia F L, Watt P M, Knuckey N W (2010b) AP-1 inhibitory peptides are neuroprotective following acute glutamate excitotoxicity in primary cortical neuronal cultures. J Neurochem 112:258-270.

Meloni B P, Majda B T, Knuckey N W (2001) Establishment of neuronal in vitro models of ischemia in 96-well microtiter strip-plates that result in acute, progressive and delayed neuronal death. Neuroscience 108:17-26.

Meloni B P, Meade A J, Kitikomolsuk D, Knuckey N W (2011) Characterisation of neuronal cell death in acute and delayed in vitro ischemia (oxygen/glucose deprivation) models. J Neurosci Methods 195:67-74.

Milletti F (2012) Cell-penetrating peptides: classes, origin, and current landscape. Drug Discov Today 17:850-860.

Moschos S A, Jones S W, Perry M M, Williams A E, Erjefalt J S, Turner J J, Barnes P J, Sproat B S, Gait M J, Lindsay M A (2007) Lung delivery studies using siRNA conjugated to TAT(48-60) and penetratin reveal peptide induced reduction in gene expression and induction of innate immunity. Bioconjug Chem 18:1450-1459.

Nagel F, Falkenburger B H, Tönges L, Kowsky S, Pöppelmeyer C, Schulz J B, Bähr M, Dietz G P (2008) Tat-Hsp70 protects dopaminergic neurons in midbrain cultures and in the substantia nigra in models of Parkinson's disease. J Neurochem 105:853-864.

Nath A, Psooy K, Martin C, Knudsen B, Magnuson D S, Haughey N, Geiger J D (1996) Identification of a human immunodeficiency virus type 1 Tat epitope that is neuroexcitatory and neurotoxic. J Virol 70:1475-1480.

Palm-Apergi C, Lönn P, Dowdy S F (2012) Do cell-penetrating peptides actually "penetrate" cellular membranes?Mol Ther 20:695-697.

Vaslin A, Rummel C, Clarke P G (2009) Unconjugated TAT carrier peptide protects against excitotoxicity. Neurotox Res 15:123-126.

Xu W, Zhou M, Baudry M (2008) Neuroprotection by cell permeable TAT-mGluR1 peptide in ischemia: synergy between carrier and cargo sequences. Neuroscientist 14:409-414.

Zhang S, Taghibiglou C, Girling K, Dong Z, Lin S Z, Lee W, Shyu W C, Wang Y T (2013) Critical role of increased PTEN nuclear translocation in excitotoxic and ischemic neuronal injuries. J Neurosci 33:7997-8008.

The invention claimed is:

1. A method of treating a surgery patient at risk of suffering cerebral ischemia or stroke, the method comprising intravenously administering to the surgery patient, 0.25 hours to 4 hours prior to the surgery, a pharmaceutical composition comprising an effective amount of a poly-arginine peptide having 12 to 18 arginine residues, wherein the pharmaceutical composition does not contain an active pharmaceutical ingredient that is not a poly-arginine peptide.

2. A method for promoting the survival of neurons and/or inhibiting neuron death from stroke in a patient scheduled for a surgery, wherein the surgery carries a risk of the patient suffering from stroke, the method comprising intravenously administering to said patient a pharmaceutical composition comprising an effective amount of a poly-arginine peptide having 12 to 18 arginine residues, wherein the pharmaceutical composition does not contain an active pharmaceutical ingredient that is not a poly-arginine peptide, and wherein the method comprises administering the pharmaceutical composition 0.25 hours to 4 hours prior to the surgery.

3. The method according to claim 2, wherein the patient is a cerebrovascular surgery patient.

4. A method according to claim 2, wherein the patient is a carotid endarterectomy patient.

5. The method according to claim 2, wherein the patient is a cardiovascular surgery patient.

6. The method according to claim 5, wherein the cardiovascular surgery patient is a coronary artery bypass graft patient.

7. The method according to claim 2, wherein the method comprises administering the pharmaceutical composition to the patient 0.5 to 3 hours prior to the surgery.

8. The method according to claim 2, wherein the method comprises administering the pharmaceutical composition to the patient 1 to 2 hours prior to the surgery.

9. The method according to claim 2, wherein the arginine residues of the poly-arginine peptide consist of D-arginine residues.

10. The method according to claim 2, wherein the arginine residues of the poly-arginine peptide consist of L-arginine residues.

11. The method according to claim 2, wherein the poly-arginine peptide is a mixture of L-arginine residues and D-arginine residues.

12. The method of claim 2, wherein the poly-arginine peptide consists of 18 arginine residues.

* * * * *